(12) United States Patent
Hu

(10) Patent No.: US 11,931,410 B1
(45) Date of Patent: Mar. 19, 2024

(54) SARS-COV-2 MRNA VACCINE AND PREPARATION METHOD AND USE THEREOF

(71) Applicant: Shenzhen Rhegen Biotechnology Co., Ltd., Shenzhen (CN)

(72) Inventor: Yong Hu, Shenzhen (CN)

(73) Assignee: SHENZHEN RHEGEN BIOTECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/260,497

(22) PCT Filed: Apr. 29, 2022

(86) PCT No.: PCT/CN2022/090196
§ 371 (c)(1),
(2) Date: Aug. 8, 2023

(87) PCT Pub. No.: WO2023/142283
PCT Pub. Date: Aug. 3, 2023

(30) Foreign Application Priority Data

Jan. 27, 2022 (CN) .......................... 202210101841.6

(51) Int. Cl.
*A61K 39/215* (2006.01)
*C12N 7/00* (2006.01)
*A61K 39/00* (2006.01)

(52) U.S. Cl.
CPC .............. *A61K 39/215* (2013.01); *C12N 7/00* (2013.01); *A61K 2039/53* (2013.01); *A61K 2039/55555* (2013.01); *C12N 2770/20034* (2013.01)

(58) Field of Classification Search
None
See application file for complete search history.

(56) References Cited

U.S. PATENT DOCUMENTS

| 10,906,944 B2 | 2/2021 | He et al. |
| 2021/0347828 A1 | 11/2021 | Dehart et al. |
| 2023/0141371 A1 | 5/2023 | Gaynor et al. |

FOREIGN PATENT DOCUMENTS

| CN | 110714015 A | 1/2020 |
| CN | 112076315 A | 12/2020 |
| CN | 112480217 A | 3/2021 |
| CN | 113234170 A | 8/2021 |
| CN | 113321739 A | 8/2021 |
| CN | 113325177 A | 8/2021 |
| CN | 113527522 A | 10/2021 |
| CN | 113980140 A | 1/2022 |
| WO | 2021159040 A2 | 8/2021 |
| WO | 2021159040 A9 | 8/2021 |
| WO | 2021159130 A2 | 8/2021 |
| WO | 2021249012 A1 | 12/2021 |

OTHER PUBLICATIONS

Chinese Patent Application Serial No. 202280001268.X, Notice of Decision of Granting Patent Right for Invention, dated Jan. 5, 2023 with listing of allowed claims.
Search Report dated Sep. 7, 2022 for counterpart Chinese patent application No. 202280001268.X, 10 pages.
Cook, P.W et al., QTD09388, "surface glycoprotein, partial [Severe acute respiratory syndrome coronavirus 2]," GenBank, Jul. 27, 2021.
Howard, D et al., UBE84889, "surface glycoprotein, partial [Severe acute respiratory syndrome coronavirus 2]," GenBank, Sep. 22, 2021.
Howard, D et al., UBE63225, "surface glycoprotein, partial [Severe acute respiratory syndrome coronavirus 2], "GenBank, Sep. 9, 2021.
Pokharel, A et al., QZD25173, "surface glycoprotein, partial [Severe acute respiratory syndrome coronavirus 2]," GenBank, Aug. 20, 2021.
Marnnar, D et al., 7SXS_A, "Chain A, Spike glycoprotein," GenBank, May 1, 2022.
Li, J.W. et al., 7WK2_A, Chain A, Spike,: GenBank, Jan. 26, 2022.
First Office Action dated Sep. 7, 2022 for counterpart Chinese patent application No. 202280001268.X, 21 pages.
Hui Zhao et al., "Long-term stability and protection efficacy of the RBD-targeting COVID-19 mRNA vaccine in nonhuman primates," Signal transduction and targeted therapy, vol. 6 No. 438.
Gao fan et al., "Research Progress and Consideration in the Novel Coronavirus Vaccine in China," Chinese Pharmaceutical Affairs, vol. 34, No. 4.
Yan lingjia et al., "Research Progress in COVID-19 Vaccines," Anti Infect Pharm, 2021, vol. 12, No. 18,1715-1723.
The Supplementary search report dated Nov. 29, 2022 for counterpart Chinese patent application No. 202280001268.X.

*Primary Examiner* — Shanon A. Foley
(74) *Attorney, Agent, or Firm* — Hoffman Warnick LLC

(57) ABSTRACT

Provided is a SARS-CoV-2 mRNA vaccine, and the preparation method and use thereof. The present invention provides an mRNA molecule capable of encoding a target polypeptide, wherein the target polypeptide comprises an NTD-RBD natural domain in the Spike (S) protein of SARS-CoV-2, and wherein the NTD-RBD natural domain comprises an NTD fragment and an RBD fragment, the NTD fragment and the RBD fragment being linked together via a natural amino acid sequence derived from the S protein as a linker. The present invention provides an mRNA encoding a NTD-RBD natural domain in the Spike protein of SARS-CoV-2, which achieves an immune effect against SARS-CoV-2 mutant strains and is widely applicable.

20 Claims, 5 Drawing Sheets
Specification includes a Sequence Listing.

SARS-COV-2 MRNA VACCINE AND PREPARATION METHOD AND USE THEREOF

TECHNICAL FIELD

The present invention relates to an mRNA vaccine and the preparation method and use thereof, more particularly, to an mRNA vaccine against SARS-CoV-2, including the prime strain and/or mutant strains, and the preparation method and use thereof.

BACKGROUND mRNA vaccine technology is useful as a fast and flexible technology platform to effectively deal with the threats of various emerging viruses. Therefore, mRNA vaccines are considered to be one of the most potential vaccines against SARS-CoV-2 (severe acute respiratory syndrome coronavirus-2). With the development and maturity of chemically modified mRNA and nano-lipid carrier technology, the advantages of mRNA in the research and development of various virus vaccines have become increasingly prominent.

Due to the specificity of the immune response, the sequence of target antigenic epitopes (including B cell epitopes and T cell epitopes) directly determines the type of immune response. Given that both B cell immunity and T cell immunity are indispensable in the clearance of the SARS-CoV-2 virus, the selection of a suitable immunogenic fragment is a key step in the design of new coronavirus vaccines. When designing target antigens for SARS-CoV-2 mutant strains, it is necessary to consider that some epitopes may induce non-neutralizing antibodies, which cannot play an effective protective function, but may rather cause an ADE effect and aggravate the degree of virus infection. Under these circumstances, therefore, further investigation needs to be conducted as regards whether the full-length S protein can continue to be used as a vaccine antigen. Upon studying of the serum of patients with COVID-19, it was found that the NTD and RBD fragments of the S protein contain multiple effective epitopes for B cells and T cells, and can induce potent protective antiviral immunity, which further proves the importance of epitope analysis when designing SARS-CoV-2 vaccines.

WO2021159040A9 discloses an mRNA vaccine encoding the NTD and RBD regions of the SARS-CoV-2 S protein. In designing the amino acid sequences, a glycine-serine linker was used to link the NTD and RBD regions.

On the other hand, new SARS-CoV-2 variants have been discovered, with a significant change in the prevalent strains around the world, and the immune escape thereof to various extents have brought challenges to the research and development of existing and future SARS-CoV-2 vaccines.

SUMMARY OF INVENTION

An object of the present invention is to provide an mRNA vaccine against SARS-CoV-2.

Another object of the present invention is to provide a preparation method of the mRNA vaccine against SARS-CoV-2.

Yet another object of the present invention is to provide a DNA template for the mRNA vaccine against SARS-CoV-2.

Still another object of the present invention is to provide the use of the mRNA vaccine against SARS-CoV-2.

In an aspect, the present invention provides an mRNA molecule capable of encoding a target polypeptide, wherein the target polypeptide comprises the NTD-RBD natural domain in the Spike (S) protein of SARS-CoV-2, and wherein the NTD-RBD natural domain comprises an NTD fragment and an RBD fragment, and a natural amino acid sequence derived from the S protein is used as a linker linking the NTD fragment and the RBD fragment.

According to a particular embodiment of the invention, the mRNA molecule provided by the present invention further encodes a signal peptide at the N terminal of the NTD-RBD natural domain.

According to a particular embodiment of the invention, the amino acid sequence encoded by the mRNA molecule provided by the present invention comprises from the N terminal to the C terminal, in this order, a signal peptide, an NTD fragment, a linker, and an RBD fragment.

According to a particular embodiment of the invention, the signal peptide includes but not limited to: a sequence consisting of amino acids at position 1 to position 12 of SEQ ID NO: 1 (MFVFLVLLPLVS).

According to a particular embodiment of the invention, in the NTD-RBD natural domain encoded by the mRNA molecule provided by the present invention, the linker has an amino acid sequence of SEQ ID NO: 50.

According to a particular embodiment of the invention, in the NTD-RBD natural domain encoded by the mRNA molecule provided by the present invention, the NTD fragment has an amino acid sequence selected from:
 (a) the amino acid sequence consisting of position 1 to position 289 of SEQ ID NO: 49;
 (b) a sequence derived by substitution, addition and/or deletion of one or more amino acids from and having the same function as the amino acid sequence of (a).

According to a particular embodiment of the invention, in the NTD-RBD natural domain encoded by the mRNA molecule provided by the present invention, the RBD fragment has an amino acid sequence selected from:
 (c) the amino acid sequence consisting of position 304 to position 526 of SEQ ID NO: 49;
 (d) a sequence derived by substitution, addition and/or deletion of one or more amino acids from and having the same function as the amino acid sequence of (c).

In the present invention, said "same function" means it has the same immunogenicity.

According to a particular embodiment of the invention, the NTD-RBD natural domain encoded by the mRNA molecule provided by the present invention has an amino acid sequence as follows:
 an amino acid sequence represented by any one of SEQ ID NO: 44 to SEQ ID NO: 49; or
 a derivative amino acid sequence having an identity of 92.78% or more with respect to any one of SEQ ID NO: 44 to SEQ ID NO: 49.

According to a particular embodiment of the invention, the NTD-RBD natural domain encoded by the mRNA molecule provided by the present invention has an amino acid sequence of one of SEQ ID NO: 49, SEQ ID NO: 48, SEQ ID NO: 47, SEQ ID NO: 46, SEQ ID NO: 45, and SEQ ID NO: 44.

According to a particular embodiment of the invention, the amino acid sequence encoded by the mRNA molecule provided by the present invention is SEQ ID NO: 21, SEQ ID NO: 17, SEQ ID NO: 13, SEQ ID NO: 9, SEQ ID NO: 5, or SEQ ID NO: 1.

According to a particular embodiment of the invention, the protein-encoding region of the mRNA molecule provided by the present invention includes a sequence consisting of nucleotides at positions 37 to 1623 of SEQ ID NO: 25, a sequence consisting of nucleotides at positions 37 to 1623 of SEQ ID NO: 26, a sequence consisting of nucleotides at positions 37 to 1623 of SEQ ID NO: 27, a sequence consisting of nucleotides at positions 37 to 1614 of SEQ ID NO: 28, a sequence consisting of nucleotides at positions 37 to 1614 of SEQ ID NO: 29, a sequence consisting of nucleotides at positions 37 to 1614 of SEQ ID NO: 30, a sequence consisting of nucleotides at positions 37 to 1617 of SEQ ID NO: 31, a sequence consisting of nucleotides at positions 37 to 1617 of SEQ ID NO: 32, a sequence consisting of nucleotides at positions 37 to 1617 of SEQ ID NO: 33, a sequence consisting of nucleotides at positions 37 to 1623 of SEQ ID NO: 34, a sequence consisting of nucleotides at positions 37 to 1623 of SEQ ID NO: 35, a sequence consisting of nucleotides at positions 37 to 1623 of SEQ ID NO: 36, a sequence consisting of nucleotides at positions 37 to 1623 of SEQ ID NO: 37, a sequence consisting of nucleotides at positions 37 to 1623 of SEQ ID NO: 38, a sequence consisting of nucleotides at positions 37 to 1623 of SEQ ID NO: 39, a sequence consisting of nucleotides at positions 37 to 1614 of SEQ ID NO: 40, a sequence consisting of nucleotides at positions 37 to 1614 of SEQ ID NO: 41, or a sequence consisting of nucleotides at positions 37 to 1614 of SEQ ID NO: 42.

According to a particular embodiment of the invention, the protein-encoding region of the mRNA molecule provided by the present invention has a sequence represented by SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

According to a particular embodiment of the invention, the mRNA molecule provided by the present invention is subjected to 1-methylpseuduridine modification.

According to a particular embodiment of the invention, the mRNA molecule provided by the present invention further comprises a 5'-UTR sequence and/or a 3'-UTR sequence.

In particular, a Kozak sequence may be or may be not included in the 5'-UTR sequence.

In some preferred embodiments of the invention, the 5'-UTR has a sequence represented by SEQ ID NO: 51.

In some preferred embodiments of the invention, the 3'-UTR sequence has a sequence represented by SEQ ID NO: 52.

According to a particular embodiment of the invention, the mRNA molecule provided by the present invention is further subjected to 3' tailing modification and/or at least one 5' capping modification.

Particularly, the 3' tailing modification includes a poly-A tail, the poly-A tail being a polyadenosinic acid with a linker inserted or not inserted therein.

Particularly, the cap structure in the at least one 5' capping modification is selected from Cap0, Cap1, ARCA, inosine, N1-methyl-guanosine, 2'-flurorine-guanosine, 7-deaza-guanosine, 8-oxy-guanosine, 2-amino-guanosine, LNA-guanosine, or 2-azido-guanosine.

According to a particular embodiment of the invention, the mRNA molecule provided by the present invention is an isolated mRNA.

According to a particular embodiment of the invention, the mRNA molecule provided by the present invention is purified. The purification includes but not limited to chromatography, lithium chloride or ethanol precipitation, centrifuge column, chlorine extraction, ethanol precipitation or gel purification.

In another aspect, the present invention provides a DNA molecule encoding any of above-mentioned mRNA molecules according to the invention.

In yet another aspect, the present invention provides a recombinant plasmid comprising the above-mentioned DNA molecule according to the invention.

In still another aspect, the present invention provides a lipid nanoparticle supported with any of above-mentioned mRNA molecules according to the invention.

In another aspect, the present invention provides a pharmaceutical composition comprising any of above-mentioned mRNA molecules according to the invention and a pharmaceutically acceptable excipient. The excipient may be selected from solvent, aqueous solvent, non-aqueous solvent, dispersing medium, diluting agent, dispersing agent, suspension adjuvant, surfactant, isotonicity agent, thickener or emulsifier, preservative, lipid, lipidoid liposome, lipid nanoparticle, core-shell nanoparticle, polymer, lipoplexe peptide, protein, cell, hyaluronidase and the mixture thereof.

In yet another aspect, the present invention provides the use of the mRNA molecule, the DNA molecule, the recombinant plasmid, the lipid nanoparticle, or the pharmaceutical composition according to the invention in the manufacture of a SARS-CoV-2 mRNA vaccine.

In still another aspect, the present invention provides a SARS-CoV-2 mRNA vaccine comprising the mRNA molecule according to the invention. In some particular embodiments of the invention, the vaccine is in a dosage form of lipid nanoparticles.

According to a particular embodiment of the invention, in the SARS-CoV-2 mRNA vaccine according to the invention, the lipid nanoparticles have a particle size of 50 to 200 nm, preferably 50 to 150 nm.

According to a particular embodiment of the invention, in the SARS-CoV-2 mRNA vaccine according to the invention, the lipid nanoparticle comprises the mRNA and a lipid, and wherein the lipid includes:
  a) one or more of a positively charged lipid and/or ionizable lipid;
  b) a neutral auxiliary lipid;
  c) cholesterol;
  d) a PEGylated lipid.

According to a particular embodiment of the invention, in the SARS-CoV-2 mRNA vaccine according to the invention, the molar ratio of the nitrogen in the positively charged lipid and/or ionizable lipid to phosphorus in the mRNA is 5:1 to 20:1.

According to a particular embodiment of the invention, for the SARS-CoV-2 mRNA vaccine according to the invention, in the lipid nanoparticle, with respect to a total moles of the lipid of 100%, each lipid component is in a proportion by mole of:
  the positively charged lipid and/or ionizable lipid, 46 to 50%;
  the neutral auxiliary lipid, 5 to 10%;
  cholesterol, 38.5 to 48%;
  the PEGylated lipid, 0 to 3%.

According to a particular embodiment of the invention, for the SARS-CoV-2 mRNA vaccine according to the invention, in the lipid nanoparticle, the ionizable lipid includes but not limited to: one or more of (dilinoleyl)methyl 4-(N,N-dimethylamino)butanoate (Dlin-MC3-DMA), SM-102, and ((4-hydroxybutyl)azanediyl)bis(hexane-6,1-diyl)bis(2-hexyldecanoate) (ALC-0315); the positively charged lipid includes but not limited to: one or more of DOTMA and DOTAP; the neutral auxiliary lipid includes but not limited to: one or more of DSPC, DOPE, and DSPE; the PEGylated lipid includes but not limited to: one or more of methoxy-poly(ethylene glycol) ditetradecylacetamide (ALC-0159) and DMG-PEG.

According to a particular embodiment of the invention, the SARS-CoV-2 mRNA vaccine according to the invention is in a lyophilized form or a frozen form.

In still another aspect, the present invention further provides a preparation method of a SARS-CoV-2 mRNA vaccine comprising a process of preparing the mRNA molecule. More particularly, the method comprises the steps of:

the DNA fragment encoding an NTD-RBD natural domain peptide fragment is synthesized, cloned to a plasmid as a template, and transcribed to prepare the target mRNA molecule;

preferably, the target mRNA molecule is any of the above-mentioned mRNA molecules according to the invention.

According to a particular embodiment of the invention, the present invention provides a preparation method of the mRNA molecule, wherein the process of synthesizing the DNA fragment encoding an NTD-RBD natural domain peptide fragment may be done by oneself or by commission. The DNA fragment is cloned to a plasmid as a template, and the target mRNA molecule may be prepared by reaction as follows:

a. three-step approach: an mRNA without capping and tailing is obtained upon in vitro transcription; a polyA structure (with a linker inserted or not inserted therein) is attached to the mRNA tail under the action of RNA polymerase and ATP, while a capping structure is attached to the 5' terminal of the uncapped mRNA under the catalysis of a capping enzyme, so as to obtain a capped and tailed mRNA molecule;

b. two-step approach: a tailed mRNA without capping is obtained upon in vitro transcription; a capping structure is attached to the 5' terminal of the uncapped mRNA under the catalysis of a capping enzyme, so as to obtain a capped and tailed mRNA molecule;

c. one-step approach: in vitro transcription and capping are carried out to obtain a capped and tailed mRNA molecule.

According to a particular embodiment of the invention, the preparation method of a SARS-CoV-2 mRNA vaccine according to the invention further comprises:

the prepared mRNA molecule is dissolved into an aqueous phase consisting of a citric acid buffer solution, and mixed with a lipid dissolved in an ethanol phase by using an impact jet flow method or a microfluidic method or the like, to prepare lipid nanoparticles having the mRNA supported thereon. Here, the lipid components may include, as mentioned above, ionizable phospholipids, neutral auxiliary phospholipids, cholesterol, PEGylated phospholipids and the like.

According to a particular embodiment of the invention, the preparation method of a SARS-CoV-2 mRNA vaccine according to the invention further comprises a process of making the prepared lipid nanoparticles into a frozen formulation or a lyophilized formulation.

According to a particular embodiment of the invention, in the preparation method of a SARS-CoV-2 mRNA vaccine according to the invention, the process of making the lipid nanoparticles into a lyophilized formulation comprises:

a) a buffer solution containing the lipid nanoparticles and a cryoprotectant is prepared;

b) the temperature is lowered for pre-freezing;

c) the temperature is raised under a vacuum condition, so as to dry the system to a moisture content of 3% or less, so as to prepare a dried formulation of the lipid nanoparticles.

According to a particular embodiment of the invention, in the preparation method of a SARS-CoV-2 mRNA vaccine according to the invention, the cryoprotectant includes but not limited to one or more of the following cryoprotectant 1 to cryoprotectant 3:

cryoprotectant 1: sucrose;
cryoprotectant 2: sucrose and non-ionic surfactant;
cryoprotectant 2: sucrose and trehalose.

According to a particular embodiment of the invention, in the preparation method of a SARS-CoV-2 mRNA vaccine according to the invention, in the prepared buffer solution containing the lipid nanoparticles and the cryoprotectant, sucrose is at a concentration (m/v) of 10 to 20%, i.e., 10 to 20 g/100 mL, preferably 12 to 18%; trehalose is at a concentration (m/v) of 0 to 20%, preferably 0 to 5%, more preferably 0.5 to 3%; the non-ionic surfactant is at a concentration (m/v) of 0 to 2%. According to some particular embodiments of the invention, the non-ionic surfactant includes but not limited to poloxamer, for example, may be Pluronic F-68. The concentration (m/v) of the poloxamer in the prepared buffer solution containing the lipid nanoparticles and the cryoprotectant is preferably 0 to 1%.

In the present invention, SEQ ID NO: 1, SEQ ID NO: 5, SEQ ID NO: 9, SEQ ID NO: 13, SEQ ID NO: 17, SEQ ID NO: 21 are the amino acid sequences of the NTD-RBD antigen of the SARS-CoV-2 prime strain, the Alpha strain, the Beta strain, the Gamma strain, the Delta strain, and the Omicron strain, respectively.

SEQ ID NO: 2, SEQ ID NO: 3, SEQ ID NO: 4 are the sequences of DNA fragments of the SARS-CoV-2 prime strain codon-optimized for the human, mouse, rat, respectively; SEQ ID NO: 25, SEQ ID NO: 26, SEQ ID NO: 27 are the sequences of the corresponding mRNA encoding regions.

SEQ ID NO: 6, SEQ ID NO: 7, SEQ ID NO: 8 are the sequences of DNA fragments of the SARS-CoV-2 Alpha strain codon-optimized for the human, mouse, rat, respectively; SEQ ID NO: 28, SEQ ID NO: 29, SEQ ID NO: 30 are the sequences of the corresponding mRNA encoding regions.

SEQ ID NO: 10, SEQ ID NO: 11, SEQ ID NO: 12 are the sequences of DNA fragments of the SARS-CoV-2 Beta strain codon-optimized for the human, mouse, rat, respectively; SEQ ID NO: 31, SEQ ID NO: 32, SEQ ID NO: 33 are the sequences of the corresponding mRNA encoding regions.

SEQ ID NO: 14, SEQ ID NO: 15, SEQ ID NO: 16 are the design of DNA fragments of the SARS-CoV-2 Gamma strain codon-optimized for the human, mouse, rat, respectively; SEQ ID NO: 34, SEQ ID NO: 35, SEQ ID NO: 36 are the sequences of the corresponding mRNA encoding regions.

SEQ ID NO: 18, SEQ ID NO: 19, SEQ ID NO: 20 are the design of DNA fragments of the SARS-CoV-2 Delta strain codon-optimized for the human, mouse, rat, respectively; SEQ ID NO: 37, SEQ ID NO: 38, SEQ ID NO: 39 are the sequences of the corresponding mRNA encoding regions.

SEQ ID NO: 22, SEQ ID NO: 23, SEQ ID NO: 24 are the design of the SARS-CoV-2 Omicron strain codon-optimized for the human, mouse, rat, respectively; SEQ ID NO: 40, SEQ ID NO: 41, SEQ ID NO: 42 are the sequences of the corresponding mRNA encoding regions.

SEQ ID NO: 43 is the mRNA sequence of the RBD antigen of the SARS-CoV-2 Delta strain.

SEQ ID NO: 44, SEQ ID NO: 45, SEQ ID NO: 46, SEQ ID NO: 47, SEQ ID NO: 48, SEQ ID NO: 49 are the amino acid sequences of the NTD-RBD natural domains of the prime strain, the Alpha strain, the Beta strain, the Gamma strain, the Delta strain, and the Omicron strain, respectively.

SEQ ID NO: 50 is the amino acid sequence of the linker in the NTD-RBD natural domain.

In the present invention, unless specifically indicated or clearly determined according to the context, the SARS-CoV-2 as mentioned includes the prime strain and/or mutant strains.

In some particular embodiments of the invention, an antigen epitope analysis is first conducted in the invention, and an mRNA vaccine formulation with NTD-RBD as the antigen target, LNP as the delivery carrier, and immunization by intramuscular injection is established. Meanwhile, by synthesizing the mRNA encoding the virus antigen fragment through UTR and codon optimization and by in vitro transcription methods, efficient expression of human cells are finally realized, with protection against all major mutant strains currently prevalent. The mRNA vaccine has a short overall production period, simply procedures and low production cost, may be stored for a long time and easily transported, without requiring a cold chain. It is impossible for traditional vaccination to quickly respond to public health events caused by many new viruses, whereas mRNA vaccines are more readily applicable, with flexible design of the sequence to cope with various pathogens, and play a critical role in fast research and development of quickly transcribed vaccines against acute infectious diseases.

The mRNA vaccine against the NTD-RBD antigen as designed in the present invention may elicit a more potent neutralizing antibody effect, given that the amount of vaccination is the same.

DETAILED DESCRIPTION OF INVENTION

Figure 1:
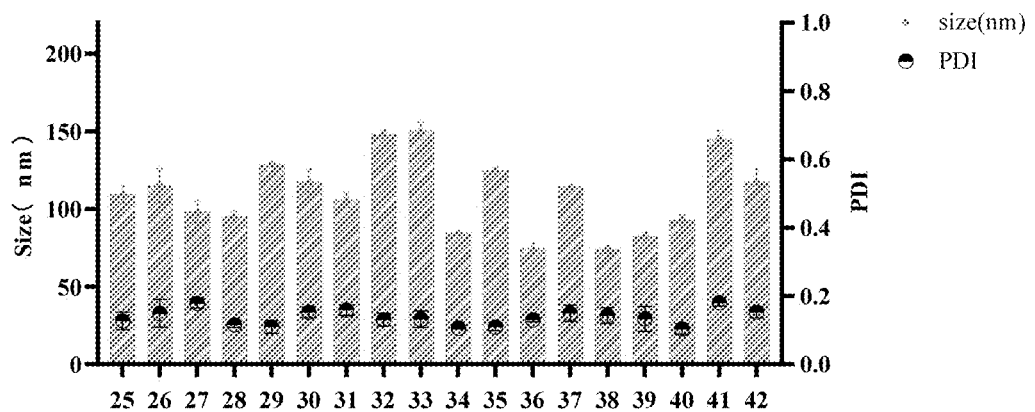
FIG. 1 shows the particle size and PDI test results of an mRNA-LNP prepared in a particular example according to the invention.

The present invention may be further described by means of the following examples, but the scope of the present invention is not limited to the following examples. Those skilled in the art will understand that various changes and modifications can be made in the present invention without departing from the spirit and scope of the invention.

The materials used in the tests and test methods are generally and/or specifically described in the invention. Although many of the materials and operation procedures used for the purposes of the present invention are known in the art, description as detailed as possible is herein provided in this invention. The operation procedures that are not described in details are performed according to the conventional procedures of the art in the related field or those recommended in the instructions provided by the manufacturer.

Example 1: mRNA Vaccine and Preparation Method Thereof

This example provides an mRNA vaccine, with the preparation method thereof mainly performed according to the following procedures.

1. A corresponding DNA fragment was synthesized according to the mRNA to be synthesized, and the DNA fragment was then cloned into an expression plasmid to obtain a recombinant plasmid. The recombinant plasmid was transfected into a host cell to obtain a recombinant cell, and the plasmid was extracted from the proliferated recombinant cells.

The constructed plasmid was subjected to enzyme digestion and linearization, with an enzyme digestion reaction system as follows (take the enzyme digestion of 2 µg recombinant plasmid as an example):

| | |
|---|---|
| 10 × Digestion Buffer I | 2 µl |
| BspQI (10 U/µl) (purchased from Vazyme) | 1 µl |
| Plasmid DNA | 2 µg |
| RNase-free Water | up to 20 µl |

The above enzyme digestion system was placed at 50° C. for 1 h. After the reaction was completed, 1 µl each of the system before and after the enzyme digestion was taken for DNA agarose gel electrophoresis (1.5% agarose gel, 5V/min, 40 min). Comparison of the electrophoresis results showed whether the recombinant plasmid was enzymatically digested completely.

Eligibility criteria: a single band was present in electrophoresis assay; with respect to the supercoiled plasmid before enzyme digestion, the band was positioned above the supercoiled plasmid; the size met the expected demand.

Assay results: a single band was present; the size was as expected and the band was positioned above the supercoiled plasmid.

2. DNA Template Ultrafiltration

The DNA template obtained above was concentrated using a Millipore 30 Kd ultrafiltration tube.

3. DNA Template FPLC Purification

To the above DNA concentrate obtained by ultrafiltration, an equal volume of a phenol/chloroform/isoamyl alcohol mixture (phenol/chloroform/isoamyl alcohol volume ratio=25/24/1) was added and sufficiently shaken before centrifugation at 12000 g for 15 min.

The precipitate was removed, and the supernatant was transferred to a new centrifuge tube, into which 3M NaAc (pH 5.2) at a volume of 1/10 of that of the supernatant was added and evenly mixed, and anhydrous ethanol of a twice volume was then added and evenly mixed. The mixture was placed at −20° C. for 30 min.

Centrifugation was carried out at 4° C., 12000 g for 10 min, and the supernatant was discarded.

The precipitate was washed with 70% ethanol, centrifuged at 12,000 g for 5 min, and the supernatant was and air-dried on an ultra-clean bench for 5 min.

The purified DNA template was dissolved in an appropriate amount of RNase-free water.

The concentration of purified template, as well as the ratios of 260/280 and 260/230, were determined by Nano-Drop. Samples were taken for DNA agarose gel electrophoresis assay (1.5% agarose, 5V/min, 40 min).

Eligibility Criteria: 260/280 between 1.8 and 2.1, 260/230 between 1.6 and 2.2.

Assay results: a concentration at 500 ng/μl, 260/280=1.90, 260/230=1.7.

4. Template Ultrafiltration after FPLC Purification

The DNA template purified by FPLC was concentrated by using a Millipore 30 Kd ultrafiltration tube, and eluted and dissolved with RNase-free water. The concentration of template after ultrafiltration and the ratios of 260/280 and 260/230 were determined by NanoDrop. Finally, it was diluted with RNase-free water to 150 ng/μl.

Assay results: a concentration at 150 ng/μl, 260/280=1.95, 260/230=1.85.

5. In Vitro Synthesis of mRNA

In vitro synthesis of the mRNA was performed in a thermostatic reactor.

The synthesis was carried out according to following synthesis system (reagents added in this order):

With a reaction volume of 1600 μl (i.e., the reaction volume of a single tube, placed in a 2 ml RNase-free tube; multiple tubes were reacted at the same time): RNA-free water 440 μl, 7.5 mM ATP 160 μl, 7.5 mM N1-methyl-pseudouridine 160 μl, 7.5 mM CTP 160 μl, 7.5 mM GTP 160 μl, 7.5 mM M7G(2′OMeA)pG 160 μl, 150 ng/μl DNA template 40 μl, 10× Buffer 160 μl and Enzyme Mix 160 μl.

The in vitro RNA synthesis procedure was carried out at 37° C. for 10 h.

After in vitro transcription and capping, the target mRNA molecules were obtained.

In each of the specific experimental examples of the present invention, in addition to the coding sequence, the target mRNA molecule further comprises 5′UTR (AGGGAGAUAAGAGAGAAAAGAAGAGUAAGAAGAAAUAUAAGAGCCGCCACC, SEQ ID NO: 51) and 3′UTR (GCUGCCUUCUGCGGGGCUUGCCUUCUGGCCAUGCCCUUCUUCUC UCCCUUGCACCUGUACCUCUUGGUCUUUGAAUAAAGCCUGAGUAGGAAG, SEQ ID NO: 52), with m7G+-5′-ppp-5′-Am2′-3′-p-(cap1) as the 5′CAP and a 3′ poly-A tail (SEQ ID NO: 53).

6. DNA Template Removal by DNase I Digestion

120 μl of DNase I was added to each Tube after the in vitro mRNA synthesis.

Mixing by inversion was done 10 times before centrifuging at 1000 rpm for 10 s.

The solution was again placed in a thermostatic reactor at 37° C. for 1 h.

After the reaction was completed, the reaction solutions were combined into an RNase-free 50 ml tube, and residual DNA fragments were assayed. Results of three tests were 0.013 ng, 0.016 ng, 0.017 ng per 100 μg of mRNA.

7. Precipitation and Recovery of mRNA

To each 50 ml Tube from the previous step, an equal volume of ammonium acetate solution was added.

The solution was mixed by inversion 10 times.

The mixture was placed at −20° C. for 2 h for precipitation.

Centrifugation was carried out at 17000 g, 4° C. for 30 min.

The supernatant was removed, and the pellet was rinsed with 70% ethanol.

Centrifugation was carried out at 17000 g, 4° C. for 10 min.

The 70% ethanol was removed, drying was conducted by evaporation on an ultra-clean bench, and 20 ml of RNase-free water was added to each tube.

After standing for 10 minutes, mixing was done by gentle blowing with a pipette tip.

The concentration of the recovered mRNA was 5 μg/μl by NanoDrop assay, with an A260/A280 of 1.90, and an A260/A230 of 2.0.

1 μl was taken and diluted 10 times, and RNA ScreenTape assay and agarose gel electrophoresis were conducted to determine the integrity of the fragment thereof.

Assay results: a matching band size and full fragment integrity.

8. mRNA Purification by LiCl Precipitation

To the mRNA recovered in the previous step, RNase-free water with a 1.5× volume thereof was added and evenly mixed.

A LiCl solution with a 1.5× volume of the mRNA pre-cooled at −20° C. was added thereto and evenly mixed.

The mixture was placed at −20° C. for 2 h.

Centrifugation was carried out at 16000 g for 20 min.

The supernatant was discarded, and the pellet was washed with 70% ethanol before centrifugation at 16,000 g for 15 min.

The supernatant was obtained and dried on an ultra-clean bench for 5 min.

The purified mRNA was dissolved in an appropriate amount of RNase-free water.

The purified mRNA was diluted to 2 μg/μl with 0.1 M citric acid.

9. LNP Preparation

Aqueous phase preparation: mRNA was diluted in a citric acid buffer to a final concentration of 2 μg/μl.

The ethanol phase solution was prepared according to Table 1.

TABLE 1

| Components | Components required for a 1 mL formulation/μL | Components required for a 0.5 mL formulation/μL |
|---|---|---|
| ALC-0315 | 559.7 | 279.8 |
| ALC-0159 | 117.2 | 58.6 |
| DSPC | 260.5 | 130.2 |
| Cholesterol | 62.7 | 31.3 |

PBS was prepared as an LNP diluent.

The operation steps of the syringe pump instrument were:

(1). Charging the A phase (mRNA buffer) into a 5 mL syringe, and charging the B phase (lipid compounds dissolved in absolute ethanol) into a 5 mL syringe, both of which were fastened on the syringe pump and tightly clamped;

(2). Connecting a chip to the syringe to set the flow rate of the syringe pump;

(3). Clicking the Start button of the syringe pump to inject the materials into the chip;

(4). Observing the color of the product at the outlet of the chip, discarding the first 5 milky white droplets (about 100 μl), and then starting to collect into 60 mL of PBS;

(5). Gently mixing the collected product by inversion before storing at 4° C.;

(6). Taking 0.3 mL as a sample for encapsulation rate test;

(7). Lysis: to 0.1 mL from step (6), adding 2 μL of 10% Triton X-100 and mixing evenly, followed by incubation at room temperature for 10 min;

(8). Encapsulation rate test: diluting 64 μL of each of the samples from step (6) and step (7) by 5 times, as LNP RNA samples before and after lysis; determining the RNA concentration; calculating the encapsulation rate by dividing the concentration difference before and after lysis by the concentration after lysis;

(9) Conducting particle size and PDI tests and Zeta potential analysis on the Zetasizer nano instrument from Malvern Company by using standard testing methods, with a loading volume of 600 μl, DTS1070 as the sample cell, and a testing temperature of 25° C.

Figure 2:
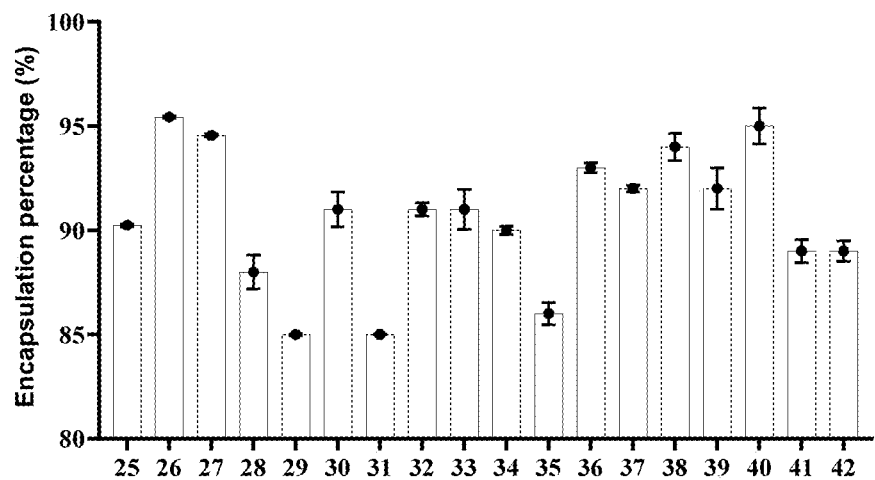
FIG. 2 shows the test results of the encapsulation percentage of an mRNA-LNP prepared in a particular example according to the invention.

The test results of particle size, PDI and encapsulation rate of the mRNA-loaded LNPs prepared in this example are shown in FIGS. 1 and 2. In FIGS. 1 and 2, the numbers on the horizontal cordinate correspond to the sequence numbers of respective mRNAs. That is, sample 25 in the Figures corresponds to the mRNA sample of SEQ ID NO: 25, sample 26 in the Figures corresponds to the mRNA sample of SEQ ID NO: 26, sample 27 in the Figures corresponds to the mRNA sample of SEQ ID NO: 27, and so on; and the sample corresponding to 42 in the figure is the mRNA sample of SEQ ID NO: 42.

10. LNP Lyophilization

Figure 3:
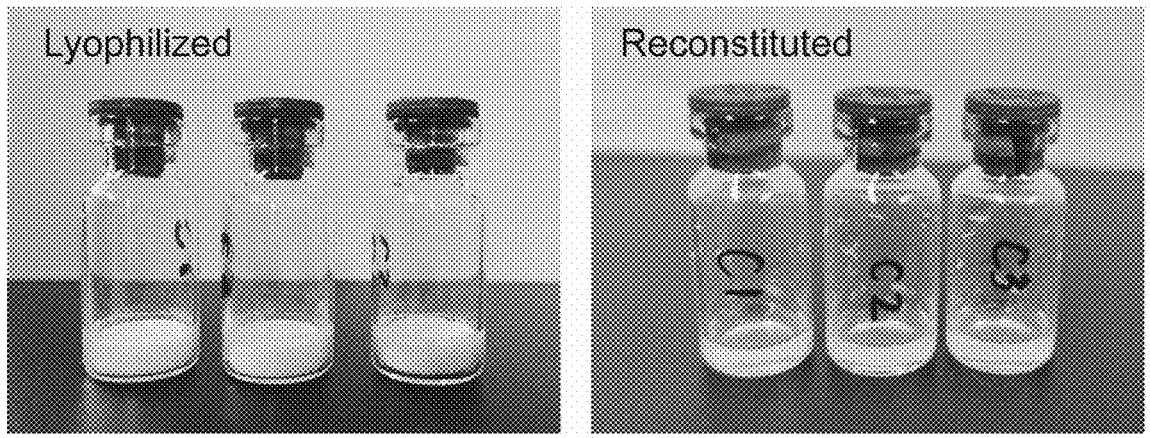
FIG. 3 shows the appearance of an mRNA lyophilized vaccine prepared in a particular example according to the invention.
Figure 4:
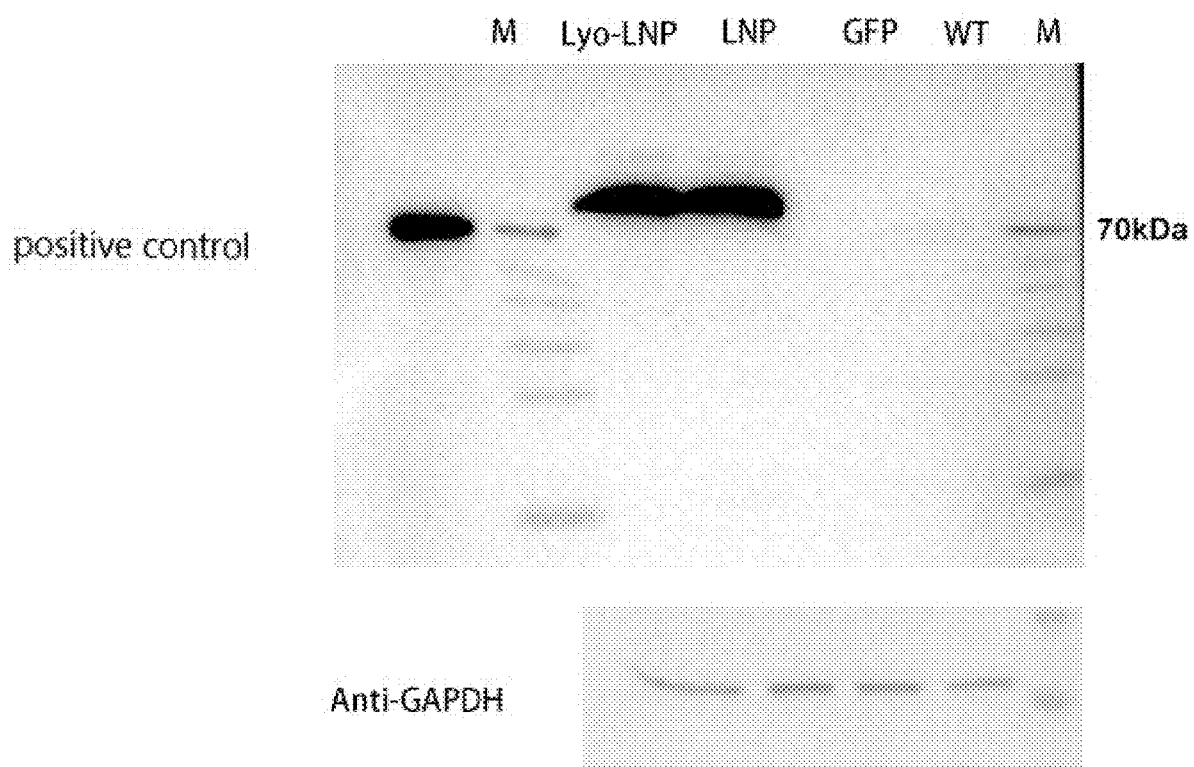
FIG. 4 illustrates the in vitro activity effects of an mRNA lyophilized vaccine prepared in a particular example according to the invention.
Figure 5:
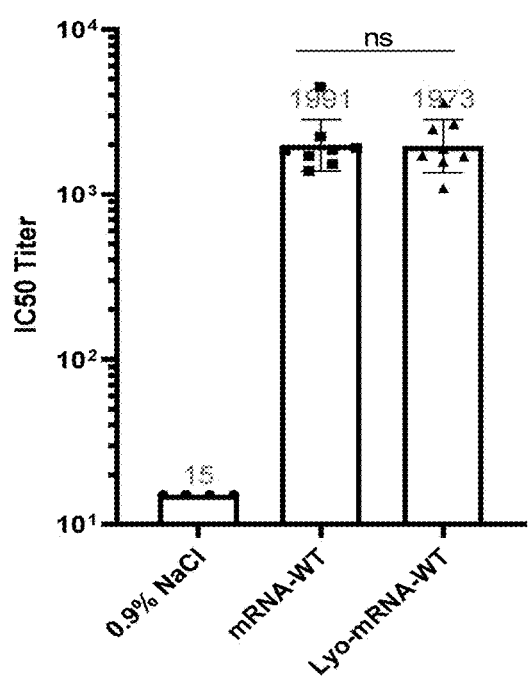
FIG. 5 illustrates the in vivo activity effects of an mRNA lyophilized vaccine prepared in a particular example according to the invention.

An cryoprotectant was added to the LNP solution and put into a lyophilizer, with a mass volume fraction (w/v %) of 15% sucrose and 2% trehalose. After pre-freezing with a cold trap (Xinzhi Scientz-10N) for 4 hours, the vacuum was turned on for vacuum suction for 48 hours, and then the samples were transferred to the upper layer of the lyophilizer for secondary drying for 16 hours. The sample temperature probe showed a temperature of about −30° C. during the drying in the cold trap, and the sample temperature probe showed a temperature of about 4° C. during the drying on the upper layer. The product (i.e., LNP lyophilized powder) was collected after drying, reconstituted with ultrapure water in a volume equal to that of the solution before lyophilization. The lyophilized powder quickly dissolved after the addition of ultrapure water in no more than 20 s during the whole process. RiboGreen™ was used to measure the encapsulation rate of the nanoparticles, and the particle size and zeta potential of the nanoparticles were measured by Omec NS-90Z Nanoparticle Size and Potential Analyzer. The mRNA lyophilized vaccine according to the present example was thus prepared. The picture of the finished product of the vaccine thus prepared and its appearance after reconstitution are shown in FIG. 3. 293T cells were culture by incubation with 2 μg of the mRNA-LNP solution, the lyophilized solution and GFP mRNA-LNP of 37 #(corresponding to the mRNA sample of SEQ ID NO: 37), respectively. After 24 hours, the cell pellet was obtained followed by cell lysis, and the soluble proteins were harvested for Western blotting to determine the protein expression efficiency. In addition, 100 μg of the mRNA-LNP powder of 37 #(corresponding to the mRNA sample of SEQ ID NO: 37) was reconstituted with 200 μl water for injection before inoculation; 6-week-old balb/c mice were inoculated twice, on day 1 and day 14, and the mouse serum was collected on day 35 to measure the anti-S protein-specific antibody titers in the serum. The results are shown in FIGS. 4 and 5. The lyophilization process essentially has no impact on the biological activity of the mRNA lipid particles.

Example 2

In this example, 100 μg mRNA-LNP powders of 25 #to 42 #(i.e., corresponding to the mRNA samples of SEQ ID NO: 25 to SEQ ID NO: 42, respectively) were each reconstituted with 200 μl water for injection before inoculation. 6-week-old balb/c mice were inoculated twice, on day 1 and day 14, and the mouse serum was collected on day 35 to measure the anti-S protein-specific antibody titers in the serum. Specifically, the following procedures were carried out:

1. Coating: the S1 protein (Yiqiao Shenzhou, 40591-MM43) was diluted with a coating buffer to a solution of 200 ng/ml and added to a microtiter plate, with a volume of 100 μl in each well, and triplicated in three wells for each dilution. After covering with a sealing film, the plate was set at 4° C. overnight.

2. Plate washing: after the 96-well plate was coated, the coating solution was poured onto an absorbent paper, and the plated was forcefully patted on the paper until there was no residue in the wells. A washing buffer was prepared, diluted 50× with deionized water, and added to the loading bottle of a plate washer. A program was set with a washing volume of 300 μl for each well, and washing was repeatedly carried out for 4 times.

3. Blocking: The washed plate was patted to dry the solution inside, and a Blocking buffer was added in a volume of 250 μl per well. Then, the plate was sealed with a sealing film, and blocking was carried out at room temperature for 2 hours.

4. Plate washing: The plate after blocking was washed as in step 2.

5. Serum incubation: Mouse serum was diluted 40×, 400×, 4000×, 40000×, 400000×, 4000000×, 40000000× with a dilution buffer, and added in a volume of 100 μl per well to the washed 96-well plate, and the plated was sealed with a sealing film and incubated at room temperature for 1.5 h.

6. Plate washing: Plate washing was carried out as in step 2, except increasing the washing number to 6 times.

7. Secondary antibody addition: HRP-labeled goat anti-mouse IgG was diluted with a dilution buffer by a dilution factor of 10000×, the diluted antibody was added to the plate in a volume of 100 μl per well, and the plated was sealed with a sealing film and incubated at room temperature in the dark 1 h.

8. Plate washing: Plate washing was carried out as in step 2. In this step, extra care was taken to completely clean the plate to be solution-free.

9. Color development: 100 μl of a TMB buffer was added, and color development was carried out in the dark for 20-30 minutes. At this time, positive samples appeared in blue.

10. Termination: 100 μl of a stop buffer was added, and the microtiter plate was read within 10 minutes, with the absorption wavelength set to 450 nm.

A standard curve was drawn based on the well absorption values of the standard, and a correlation coefficient of linear regression of greater than 0.0995 was required. The residual content of the S protein-specific antibody in the sample was calculated according to the absorbance of the product to be tested.

Figure 6:
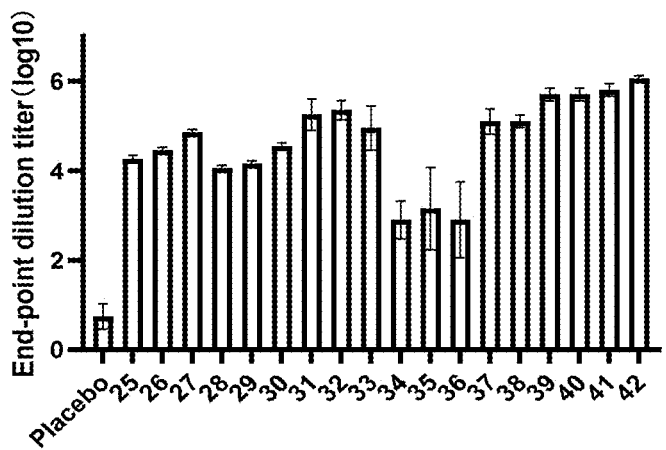
FIG. 6 shows the test results of the specific antibody titer of the mRNA vaccine according to the invention.

The results of the specific antibody titer assay are shown in FIG. 6. The results suggested that the NTD-RBD-encoding mRNA candidate vaccine had good immunogenicity and induced the production of specific antibodies against the S protein. The mice in the control group injected with saline were not able to produce a specific antibody against the S protein.

Example 3

In this example, the antibody titers in the RBD-encoding mRNA vaccine (43 #, i.e., the sample corresponding to SEQ ID NO: 43) and the NTD-RBD-encoding vaccine (37 #, i.e., the sample corresponding to SEQ ID NO: 37) were investigated through experiments.

Specifically, the following procedures were carried out:

For vaccination, 6-8 weeks old female mice were inoculated with 5 μg of the SARS-CoV-2 mRNA vaccine (dissolved in PBS, 200 μl, intramuscular injection) on day 0 (0d) and day 14 (14 d) respectively; on day 28 (28 d), the peripheral blood of the mice was sampled.

Vero E6 cells (24-well plate) were prepared, with serum inactivation by heating and serial dilutions in 3-fold. 100 l of the serum and 100 l of the virus stock solution (100 PFU) were mixed in equivalent volumes, and 100 μl of DMEM (containing 2% FBS) was mixed with an equivalent volume of 100 l of the virus solution as a negative control. Incubation was carried out at 37° C. for 1 h.

The above serum-virus mixture (200 μl in total) was transferred to the Vero E6 cells in a 24-well plate and adsorbed for 1 h. During this time, gentle mixing could be carried out 3-4 times. The adsorption solution from the previous step was then removed, and the medium was changed to a methylcellulose medium, followed by incubation for 3 days. The system was fixed with paraformaldehyde, stained with crystal violet, and the number of plaques was then counted. Serum neutralization percentage was calculated based on the negative control. The curve was fitted by using the JMP analysis software with the Probit approach, and the $PRNT_{50}$ value was calculated.

Figure 7:
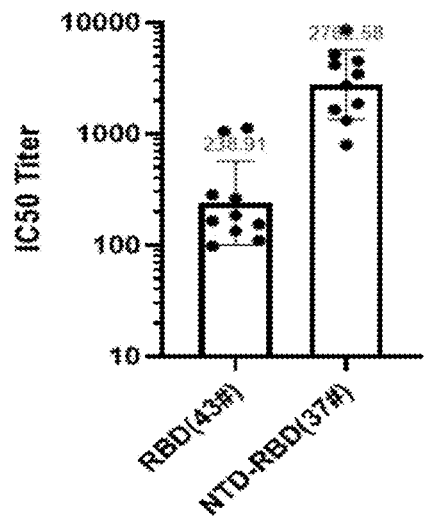
FIG. 7 shows a comparison of antigenicity between the RBD and NTD-RBD antigens.

The experimental results are shown in FIG. 7. The neutralizing antibody titer induced by NTD-RBD was higher than that of RBD, and consequently the immunogenicity of NTD-RBD was better than that of RBD.

Example 4

In this example, the cross-immune protection of the NTD-RBD mRNA vaccine against the 2019-nCoV pseudovirus was investigated through experiments. Specifically, the following procedures were carried out:

For vaccination, 6-8 weeks old female mice were inoculated with 5 μg of the SARS-CoV-2 mRNA vaccine (dissolved in PBS, 200 μl, intramuscular injection) on day 0 (0d) and day 14 (14 d) respectively; on day 28 (28 d), the peripheral blood of the mice was sampled. A micro-neutralization assay was used to test the heat-inactivated serum, to determine the level of antibody neutralization of the 2019-nCoV pseudovirus infecting ACE2-expressing monolayer cells. 4 wells were diluted in a 96-well plate, and the viral cytopathic effect (cpe) in the cells was tested on day 3 and day 4. The degree of dilution of the serum (as assayed by the 50% end-point method) at which complete suppression of cpe was achieved in the serum was calculated by the Reed Muench equation. Nonparametric two-tailed t-test (Mann-Whiteny) was used for statistical analysis.

Figure 8:
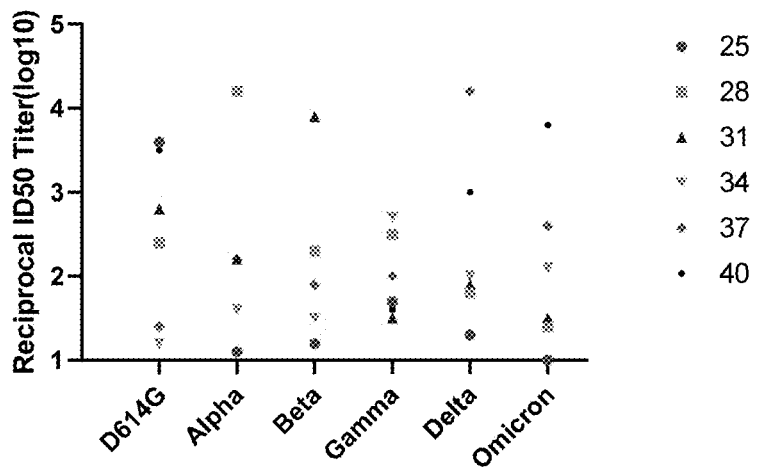
FIG. 8 shows the cross protection effect against various strains of the NTD-RBD mRNA vaccine according to the invention.

The experimental results are shown in FIG. 8 (the reference numbers in each panel of the figure were the samples corresponding to the same SEQ ID NOs., respectively). The mRNA vaccines constructed in the present invention had a cross-protection effect to various extents on the SARS-CoV-2 mutant strain.

Example 5: Induction of Strong Cellular Immunity by NTD-RBD SARS-CoV-2 Vaccines

In this example, the effect of the NTD-RBD SARS-CoV-2 vaccines in inducing cellular immunity was investigated. Specifically, the following procedures were carried out:

1. 96-Well Plate Coating

PVDF membrane in a 96-well plate was infiltrated with 70% ethanol for 30 s.

A capture antibody (diluted in PBS) was added and kept at 4° C. overnight.

The plate was emptied of the coating solution, gently patted dry on paper, and washed with PBS (use of a plate washer was not allowed).

100 ul of 2% non-fat dry milk powder (or BSA) was added for incubation at room temperature for 2 hours to block the blank wells in the plate.

The plate was washed once with PBS.

2. Cell Stimulation and Cytokine Capture

For vaccination, 6-8 weeks old female mice were inoculated with 5 μg of the SARS-CoV-2 mRNA vaccine RH109 (40 #) (dissolved in PBS, 200 μl, intramuscular injection) on day 0 (0d) and day 14 (14 d) respectively; on day 28 (28 d), the peripheral blood of the mice was sampled. PBMCs were separated from fresh blood with Ficoll and counted, and the cells were diluted with a medium and added to a 96-well plate. The general number of cells used was 1 to $2 \times 10^5$/well.

The 96-well plate was incubated overnight in a 37° C. $CO_2$ incubator. Moving or shaking the plate was not allowed.

An S protein stimulating material (pepmix) was added to the plate and incubated for 8 hours.

Incubation was carried out with PBS containing 0.1% Tween 20 for 10 minutes before the cells and unbound cytokines were removed. The plate was then washed 3 times with PBS containing 0.1% Tween 20.

3. Detection by Adding Detecting Antibody

A labeled detecting antibody (diluted in PBS containing 1% BSA) was added and incubated at room temperature for 1-2 hours.

A substrate was added for color developing (before adding the substrate, both sides of the plate membrane were washed with distilled water to avoid a background resulted from leaked solution). The formation of spots was monitored, and the reaction was terminated at an appropriate point.

The reaction was terminated by washing with distilled water.

4. Result Analysis

The 96-well plate was dried (the plate was kept in the dark at 4° C. overnight so that the edge of the spots were sharp and easier to be distinguished).

Figure 9:
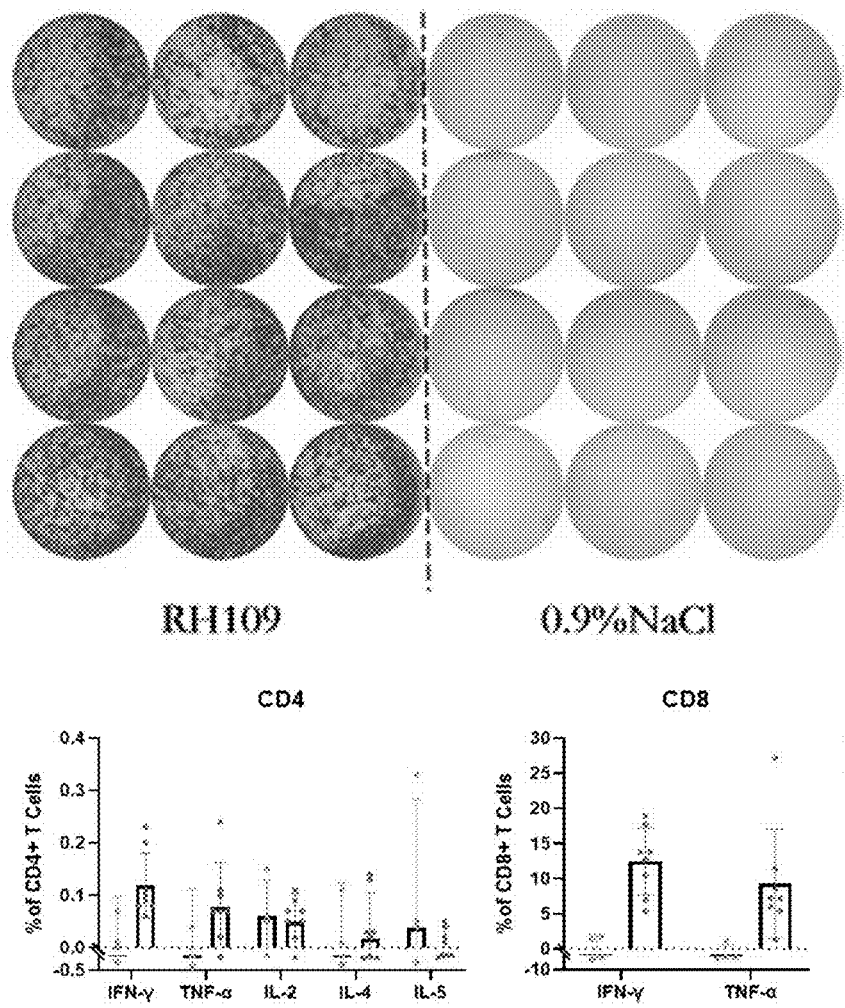
FIG. 9 illustrates the strong cellular immunization induced by the NTD-RBD vaccine according to the invention.

The results were analyzed by using a plate reader, as shown in FIG. 9. The ELISPot experiment showed that after the polypeptide stimulation, a large number of IFN-γ plaques were produced for the vaccinated mouse group up to 3000 plaques/1 million cells, while almost no plaque produced for the saline group, indicating that RH109 induced a strong cellular immune response.

Further analysis of CD4 and CD8 cells by flow cytometry intracellular staining showed that IL2$^+$/TNF-α$^+$/IFN-γ$^+$ CD4$^+$ cells and TNF-α$^+$/IFN-γ$^+$ CD8$^+$ cells were significantly increased, indicating that the RH109 vaccine activated strong Th1-type and CD8 killer T-cell immune responses.

Example 6

Figure 10:
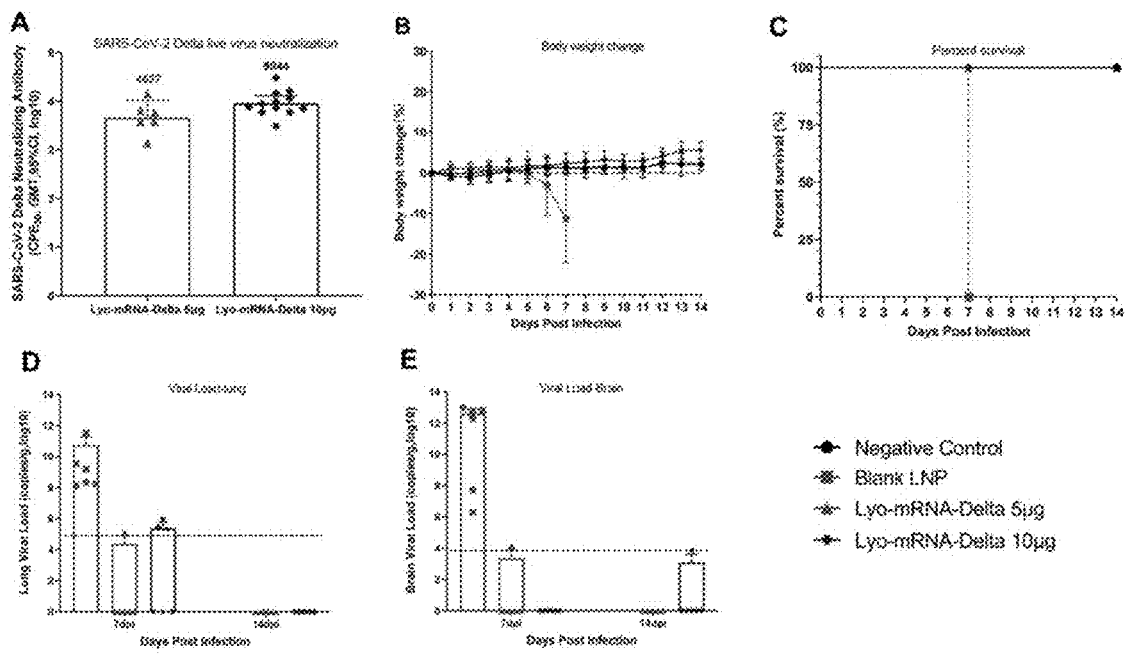
FIG. 10 shows the experimental results of in vivo challenging in ACE2 mice with the NTD-RBD vaccine according to the invention.

For vaccination, 6-8 weeks old female mice were inoculated with 5 μg of the SARS-CoV-2 mRNA vaccine (37 #) (dissolved in PBS, 200 μl, intramuscular injection) on day 0 (0d) and day 14 (14 d) respectively; ivD being the challenge period, and ivD0 was day 0 of the challenge. hACE2 transgenic mice were intranasally infected by SARS-CoV-2 (the Delta strain), and the infection dose was preliminarily 105 PFU. D42 is the duration of the challenge. After the challenge at ivD3 and ivD5, animals were euthanized in batches. Lungs (right lung) and other tissues and organs were harvested from the euthanized animals, RNA was extracted, and the viral load or live virus titer was determined by Q-PCR method. During the procedure, observation was made twice a day, and the body weight was measured once a week. The viral load and survival profile are shown in FIG. 10. It can be seen from FIG. 10 that the viral load in the lungs of the vaccinated mice was significantly lower than those of the control group after the true virus challenge experiment. The mice in the adjuvant control group all reached the criterion for euthanasia on day 7 after the challenge. Compared with the adjuvant control group, all the mice in the low-dose vaccine group and the high-dose vaccine group survived, indicating that the vaccine had a significant protective effect on the mice infected with the SARS-CoV-2 Delta strain.

Example 7

Figure 11:
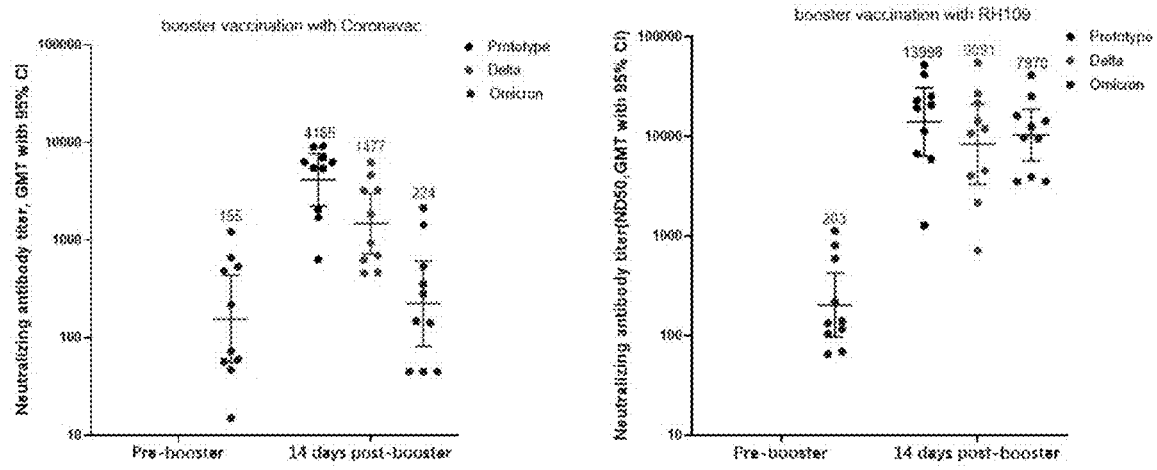
FIG. 11 shows the experimental results of the NTD-RBD vaccine according to the invention as a booster dose.
Figure 12:
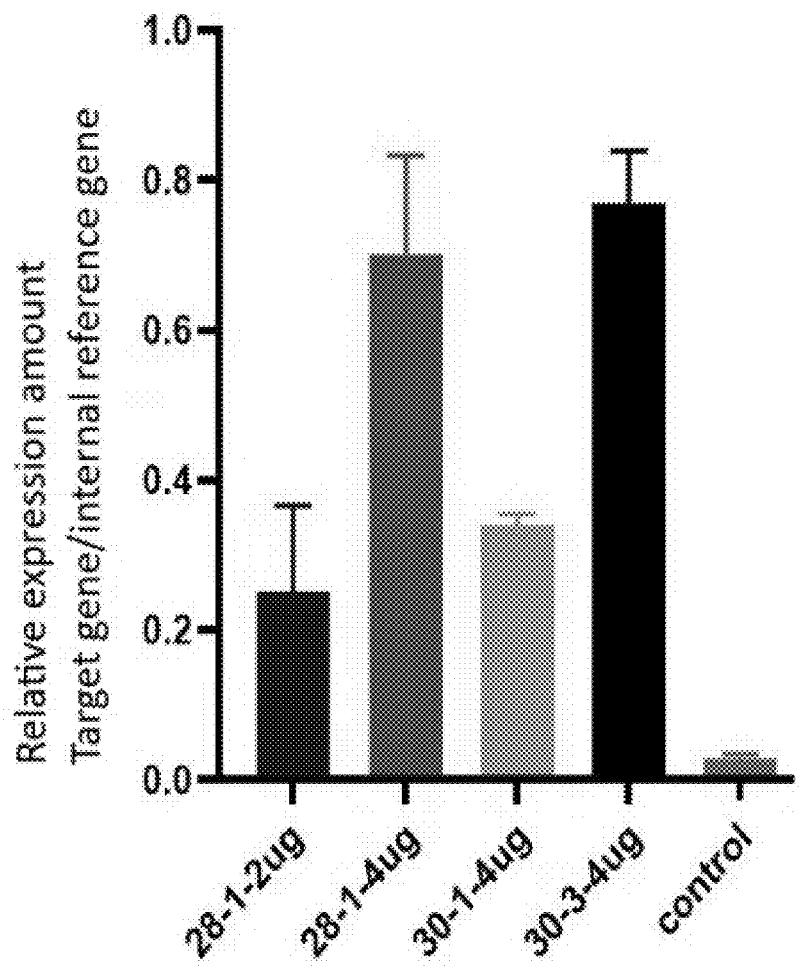
FIG. 12 shows the experimental results of the relative expression amount of the protein expression induced by the mRNA according to certain particular examples according to the invention.

For vaccination, 6-8 weeks old female mice were inoculated with two doses of the SINOVAC inactivated vaccine on day 0 (0d) and day 14 (14 d), and 5 μg of the SARS-CoV-2 mRNA vaccine RH109 (dissolved in PBS, 200 μl, intramuscular injection) on day 42 (42 d). On day 56 (56 d), the peripheral blood of the mice was sampled. A microneutralization assay was used to test the heat-inactivated serum, to determine the level of antibody neutralization of the SARS-CoV-2 pseudovirus infecting ACE2-expressing monolayer cells. 4 wells were diluted in a 96-well plate, and the viral cytopathic effect (cpe) in the cells was tested on day 3 and day 4. The degree of dilution of the serum (as assayed by the 50% end-point method) at which complete suppression of cpe was achieved in the serum was calculated by the Reed Muench equation. Nonparametric two-tailed t-test (Mann-Whiteny) was used for statistical analysis. As shown in FIG. 11, the RH109-immunized serum produced a high level of neutralizing antibodies to Omicron, Delta, and the prime strain, with a geometric average titer of 7970, 9091, and 13998, respectively. Among them, the tier was increased 39 times than that after the second dose against Omicron. Further, the titer was 35, 6.2, and 3.4 times against Omicron, Delta, and the prime strain respectively, as compared to the case where the SINOVAC inactivated vaccine was used as the third dose for boosting, indicating that RH109 was very suitable as a booster dose in addition to a first dose of an inactivated vaccine. Furthermore, various mRNAs according to the invention at different doses in inducing protein expression were also compared in the present invention through experiment; in this experiment, 293T cells were incubated with 2 μg or 4 μg of an mRNA-LNP solution of SEQ ID NO: 28, SEQ ID NO: 54, and SEQ ID NO: 55 respectively, the cell pellet was collected after 24 hours and then lysed, and the obtained bands of the target protein were assayed in parallel by grayscale analysis for the relative amount of intracellular protein expression within 24 hours. The results are shown in FIG. 12 (in this figure, reference number 28-1 corresponds to SEQ ID NO: 4L, 30-1 corresponds to SEQ ID NO: 54, and 30-3 corresponds to SEQ ID NO: 55). The mRNA of the present invention showed excellent efficiency in protein expression.

It should be noted that those described above are merely preferred examples of the present invention, and are not intended to limit the present invention. Those skilled in the art would understand that various modifications and changes are available to the present invention. Any changes, equivalent substitution, modification and the like made within the spirit and principle of the present invention are intended to be included within the scope of the present invention.

The invention claimed is:

1. An mRNA molecule encoding an amino acid sequence as shown in SEQ ID NO: 21.

2. The mRNA molecule according to claim 1, wherein the coding sequence of the mRNA is as shown in SEQ ID NO: 40, SEQ ID NO: 41, or SEQ ID NO: 42.

3. The mRNA molecule according to claim 1, wherein the mRNA has been subjected to 1-methylpseudouridine modification.

4. The mRNA molecule according to claim 1, further comprising a 5'-UTR sequence and/or a 3'-UTR sequence.

5. The mRNA molecule according to claim 4, wherein a Kozak sequence is or is not included in the 5'-UTR sequence.

6. The mRNA molecule according to claim 4, wherein the 5'-UTR has a sequence represented by SEQ ID NO: 51.

7. The mRNA molecule according to claim 4, wherein the 3'-UTR sequence has a sequence represented by SEQ ID NO: 52.

8. The mRNA molecule according to claim 4, wherein the mRNA has been subjected to a 3' tailing modification and/or at least one 5' capping modification.

9. The mRNA molecule according to claim 8, wherein the 3' tailing modification includes a poly-A tail, and the poly-A tail is a polyadenosinic acid with or without a linker inserted therein;

the cap structure in the at least one 5' capping modification is selected from Cap0, Cap1, ARCA, inosine, N1-methyl-guanosine, 2'-flurorine-guanosine, 7-deaza-guanosine, 8-oxy-guanosine, 2-amino-guanosine, LNA-guanosine, or 2-azido-guanosine.

10. The mRNA molecule according to claim 1, which is an isolated mRNA.

11. The mRNA molecule according to claim 10, the mRNA molecule is purified.

12. A SARS-CoV-2 mRNA vaccine comprising the mRNA molecule according to claim 1, wherein the vaccine is in a dosage form of lipid nanoparticles.

13. The SARS-CoV-2 mRNA vaccine according to claim 12, wherein the lipid nanoparticle comprises the mRNA and a lipid, and the lipid includes:

a) one or more of a positively charged lipid and/or ionizable lipid;

b) a neutral auxiliary lipid;

c) cholesterol; and d) a PEGylated lipid.

14. The SARS-CoV-2 mRNA vaccine according to claim 13, wherein the molar ratio of the nitrogen in the positively charged lipid and/or ionizable lipid to phosphorus in the mRNA is 5:1 to 20:1.

15. The SARS-CoV-2 mRNA vaccine according to claim 13, wherein the ionizable lipid includes, but is not limited to, one or more of (dilinoleyl)methyl 4-(N,N-dimethylamino) butanoate, SM-102, and ((4-hydroxybutyl)azanediyl)bis (hexane-6,1-diyl)bis(2-hexyldecanoate);

the positively charged lipid includes, but is not limited to, one or more of DOTMA and DOTAP;

the neutral auxiliary lipid includes, but is not limited to, one or more of DSPC, DOPE, and DSPE; and the PEGylated lipid includes, but is not limited to, one or more of methoxypoly(ethylene glycol) ditetradecylacetamide and DMG-PEG.

16. The SARS-CoV-2 mRNA vaccine according to claim 12, wherein the dosage form of the vaccine is a lyophilized form or a frozen form.

17. A method for preparing a SARS-CoV-2 mRNA vaccine, comprising the steps of:

synthesizing a DNA fragment encoding an NTD-RBD natural domain peptide, cloning it to a plasmid as a template, and transcribing it to prepare the target mRNA molecule;

wherein the target mRNA molecule is the mRNA molecule according to claim 1.

18. The method according to claim 17, further comprising:

dissolving the prepared mRNA molecule in an aqueous phase consisting of a citric acid buffer solution, and mixing it with lipid components dissolved in an ethanol phase by using an impact jet flow method or a microfluidic method or the like, to prepare lipid nanoparticles carrying the mRNA.

19. The method according to claim 18, further comprising a process of making the prepared lipid nanoparticles into a frozen formulation or a lyophilized formulation.

20. The method according to claim 19, wherein the process of making the lipid nanoparticles into a lyophilized formulation comprises:

a) preparing a buffer solution containing the lipid nanoparticles and a cryoprotectant;

b) lowering the temperature for pre-freezing; and c) raising the temperature under a vacuum condition to dry the system to a moisture content of 3% or less, so as to prepare a dried formulation of the lipid nanoparticles.

* * * * *

SEQUENCE LISTING

```
<160> NUMBER OF SEQ ID NOS: 55

<210> SEQ ID NO 1
<211> LENGTH: 541
<212> TYPE: PRT
<213> ORGANISM: Artificial Sequence
<220> FEATURE:
<223> OTHER INFORMATION: Antigen

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45
```

```
His Ser Thr Gln Asp Leu Phe Leu Pro Phe Phe Ser Asn Val Thr Trp
    50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
                85                  90                  95
Lys Ser Asn Ile Ile Arg Gly Trp Ile Phe Gly Thr Thr Leu Asp Ser
            100                 105                 110
Lys Thr Gln Ser Leu Leu Ile Val Asn Asn Ala Thr Asn Val Val Ile
        115                 120                 125
Lys Val Cys Glu Phe Gln Phe Cys Asn Asp Pro Phe Leu Gly Val Tyr
    130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                165                 170                 175
Met Asp Leu Glu Gly Lys Gln Gly Asn Phe Lys Asn Leu Arg Glu Phe
            180                 185                 190
Val Phe Lys Asn Ile Asp Gly Tyr Phe Lys Ile Tyr Ser Lys His Thr
        195                 200                 205
Pro Ile Asn Leu Val Arg Asp Leu Pro Gln Gly Phe Ser Ala Leu Glu
    210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
        275                 280                 285
Val Asp Cys Ala Leu Asp Pro Leu Ser Glu Thr Lys Cys Thr Leu Lys
    290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
        355                 360                 365
Tyr Asn Ser Ala Ser Phe Ser Thr Phe Lys Cys Tyr Gly Val Ser Pro
    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
        435                 440                 445
Tyr Asn Tyr Leu Tyr Arg Leu Phe Arg Lys Ser Asn Leu Lys Pro Phe
    450                 455                 460
```

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe
    530                 535                 540

```
<210> SEQ ID NO 2
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 2
```

| | | | | | |
|---|---|---|---|---|---|
| atgttcgtgt | tcctggtgct | gctgcccctg | gtgagcagcc | agtgcgtgaa | cctgaccacc | 60 |
| aggacccagc | tgccccccgc | ctacaccaac | agcttcacca | ggggcgtgta | ctaccccgac | 120 |
| aaggtgttca | ggagcagcgt | gctgcacagc | acccaggacc | tgttcctgcc | cttcttcagc | 180 |
| aacgtgacct | ggttccacgc | catccacgtg | agcggcacca | acggcaccaa | gaggttcgac | 240 |
| aaccccgtgc | tgcccttcaa | cgacggcgtg | tacttcgcca | gcaccgagaa | gagcaacatc | 300 |
| atcaggggct | ggatcttcgg | caccaccctg | gacagcaaga | cccagagcct | gctgatcgtg | 360 |
| aacaacgcca | ccaacgtggt | gatcaaggtg | tgcgagttcc | agttctgcaa | cgacccottc | 420 |
| ctgggcgtgt | actaccacaa | gaacaacaag | agctggatgg | agagcgagtt | cagggtgtac | 480 |
| agcagcgcca | acaactgcac | cttcgagtac | gtgagccagc | ccttcctgat | ggacctggag | 540 |
| ggcaagcagg | gcaacttcaa | gaacctgagg | gagttcgtgt | tcaagaacat | cgacggctac | 600 |
| ttcaagatct | acagcaagca | cacccccatc | aacctggtga | gggacctgcc | ccagggcttc | 660 |
| agcgccctgg | agcccctggt | ggacctgccc | atcggcatca | acatcaccag | gttccagacc | 720 |
| ctgctggccc | tgcacaggag | ctacctgacc | cccggcgaca | gcagcagcgg | ctggaccgcc | 780 |
| ggcgccgccg | cctactacgt | gggctacctg | cagcccagga | ccttcctgct | gaagtacaac | 840 |
| gagaacggca | ccatcaccga | cgccgtggac | tgcgccctgg | accccctgag | cgagaccaag | 900 |
| tgcaccctga | gagcttcac | cgtggagaag | ggcatctacc | agaccagcaa | cttcagggtg | 960 |
| cagcccaccg | agagcatcgt | gaggttcccc | aacatcacca | acctgtgccc | cttcggcgag | 1020 |
| gtgttcaacg | ccaccaggtt | cgccagcgtg | tacgcctgga | acaggaagag | gatcagcaac | 1080 |
| tgcgtggccg | actacagcgt | gctgtacaac | agcgccagct | tcagcacctt | caagtgctac | 1140 |
| ggcgtgagcc | ccaccaagct | gaacgacctg | tgcttcacca | acgtgtacgc | cgacagcttc | 1200 |
| gtgatcaggg | gcgacgaggt | gaggcagatc | gcccccggcc | agaccggcaa | gatcgccgac | 1260 |
| tacaactaca | agctgcccga | cgacttcacc | ggctgcgtga | tcgcctggaa | cagcaacaac | 1320 |
| ctggacagca | aggtgggcgg | caactacaac | tacctgtaca | ggctgttcag | gaagagcaac | 1380 |
| ctgaagcoct | tcgagaggga | catcagcacc | gagatctacc | aggccggcag | cacccoctgc | 1440 |
| aacggcgtgg | agggcttcaa | ctgctacttc | cccctgcaga | gctacggctt | ccagcccacc | 1500 |
| aacggcgtgg | gctaccagcc | ctacagggtg | gtggtgctga | gcttcgagct | gctgcacgcc | 1560 |
| cccgccaccg | tgtgcggccc | caagaagagc | accaacctgg | tgaagaacaa | gtgcgtgaac | 1620 |

| | |
|---|---:|
| ttc | 1623 |

<210> SEQ ID NO 3
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 3

| | |
|---|---:|
| atgttcgtgt tcctggtgct gctgcctctg gtgagcagcc agtgcgtgaa cctgaccacc | 60 |
| agaacccagc tgcctcctgc ctacaccaac agcttcacca gaggcgtgta ctaccctgac | 120 |
| aaggtgttca gaagcagcgt gctgcacagc acccaggacc tgttcctgcc tttcttcagc | 180 |
| aacgtgacct ggttccacgc catccacgtg agcggcacca acggcaccaa agattcgac | 240 |
| aaccctgtgc tgccttttcaa cgacggcgtg tacttcgcca gcaccgagaa gagcaacatc | 300 |
| atcagaggct ggatcttcgg caccaccctg gacagcaaga cccagagcct gctgatcgtg | 360 |
| aacaacgcca ccaacgtggt gatcaaggtg tgcgagttcc agttctgcaa cgacccttc | 420 |
| ctgggcgtgt actaccacaa gaacaacaag agctggatgg agagcgagtt cagagtgtac | 480 |
| agcagcgcca acaactgcac cttcgagtac gtgagccagc cttttcctgat ggacctggag | 540 |
| ggcaagcagg gcaacttcaa gaacctgaga gagttcgtgt tcaagaacat cgacggctac | 600 |
| ttcaagatct acagcaagca cacccctatc aacctggtga gacctgcc tcagggcttc | 660 |
| agcgccctgg agcctctggt ggacctgcct atcggcatca acatcaccag attccagacc | 720 |
| ctgctggccc tgcacagaag ctacctgacc cctggcgaca gcagcagcgg ctggaccgcc | 780 |
| ggcgccgccg cctactacgt gggctacctg cagcctagaa ccttcctgct gaagtacaac | 840 |
| gagaacggca ccatcaccga cgccgtggac tgcgccctgg accctctgag cgagaccaag | 900 |
| tgcaccctga agagcttcac cgtggagaag ggcatctacc agaccagcaa cttcagagtg | 960 |
| cagcctaccg agagcatcgt gagattccct aacatcacca cctgtgccc tttcggcgag | 1020 |
| gtgttcaacg ccaccagatt cgccagcgtg tacgcctgga cagaaagag aatcagcaac | 1080 |
| tgcgtggccg actacagcgt gctgtacaac agcgccagct tcagcacctt caagtgctac | 1140 |
| ggcgtgagcc ctaccaagct gaacgacctg tgcttcacca acgtgtacgc cgacagcttc | 1200 |
| gtgatcagag cgacgaggt gagacagatc gcccctggcc agaccggcaa gatcgccgac | 1260 |
| tacaactaca agctgcctga cgacttcacc ggctgcgtga tcgcctggaa cagcaacaac | 1320 |
| ctggacagca aggtgggcgg caactacaac tacctgtaca gactgttcag aaagagcaac | 1380 |
| ctgaagcctt tcgagagaga catcagcacc gagatctacc aggccggcag cacccttgc | 1440 |
| aacggcgtgg agggcttcaa ctgctacttc cctctgcaga gctacggctt ccagcctacc | 1500 |
| aacggcgtgg gctaccagcc ttacagagtg gtggtgctga gcttcgagct gctgcacgcc | 1560 |
| cctgccaccg tgtgcggccc taagaagagc accaacctgg tgaagaacaa gtgcgtgaac | 1620 |
| ttc | 1623 |

<210> SEQ ID NO 4
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 4

| | |
|---|---:|
| atgttcgtgt tcctggtgct gctgcccctg gtgagcagcc agtgcgtgaa cctgaccacc | 60 | aggacccagc tgccccccgc ctacaccaac agcttcacca ggggcgtgta ctaccccgac    120 aaggtgttca ggagcagcgt gctgcacagc acccaggacc tgttcctgcc cttcttcagc    180 aacgtgacct ggttccacgc catccacgtg agcggcacca acggcaccaa gaggttcgac    240 aaccccgtgc tgcccttcaa cgacggcgtg tacttcgcca gcaccgagaa gagcaacatc    300 atcagggget ggatcttcgg caccaccctg acagcaaga cccagagcct gctgatcgtg    360 aacaacgcca ccaacgtggt gatcaaggtg tgcgagttcc agttctgcaa cgaccccttc    420 ctgggcgtgt actaccacaa gaacaacaag agctggatgg agagcgagtt cagggtgtac    480 agcagcgcca caactgcac cttcgagtac gtgagccagc ccttcctgat ggacctggag    540 ggcaagcagg gcaacttcaa gaacctgagg gagttcgtgt tcaagaacat cgacggctac    600 ttcaagatct acagcaagca cacccccatc aacctggtga gggacctgcc ccagggcttc    660 agcgccctgg agcccctggt ggacctgccc atcggcatca acatcaccag gttccagacc    720 ctgctggccc tgcacaggag ctacctgacc cccggcgaca gcagcagcgg ctggaccgcc    780 ggcgccgccg cctactacgt gggctacctg cagcccagga ccttcctgct gaagtacaac    840 gagaacggca ccatcaccga cgccgtggac tgcgccctgg acccctgag cgagaccaag    900 tgcaccctga gagcttcac cgtggagaag ggcatctacc agaccagcaa cttcagggtg    960 cagcccaccg agagcatcgt gaggttcccc aacatcacca acctgtgccc cttcggcgag    1020 gtgttcaacg ccaccaggtt cgccagcgtg tacgcctgga caggaagag gatcagcaac    1080 tgcgtggccg actacagcgt gctgtacaac agcgccagct tcagcacctt caagtgctac    1140 ggcgtgagcc ccaccaagct gaacgacctg tgcttcacca acgtgtacgc cgacagcttc    1200 gtgatcaggg gcgacgaggt gaggcagatc gcccccggcc agaccggcaa gatcgccgac    1260 tacaactaca agctgcccga cgacttcacc ggctgcgtga tcgcctggaa cagcaacaac    1320 ctggacagca aggtgggcgg caactacaac tacctgtaca ggctgttcag gaagagcaac    1380 ctgaagccct tcgagaggga catcagcacc gagatctacc aggccggcag cacccctgc    1440 aacggcgtgg agggcttcaa ctgctacttc cccctgcaga gctacggctt ccagcccacc    1500 aacggcgtgg gctaccagcc ctacagggtg gtggtgctga cttcgagct gctgcacgcc    1560 cccgccaccg tgtgcggccc caagaagagc accaacctgg tgaagaacaa gtgcgtgaac    1620 ttc    1623

<210> SEQ ID NO 5
<211> LENGTH: 538
<212> TYPE: PRT
<213> ORGANISM: Artificial Sequence
<220> FEATURE:
<223> OTHER INFORMATION: Antigen

<400> SEQUENCE: 5

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

-continued

```
Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Gly Val Tyr His Lys
    130                 135                 140

Asn Asn Lys Ser Trp Met Glu Ser Glu Phe Arg Val Tyr Ser Ser Ala
145                 150                 155                 160

Asn Asn Cys Thr Phe Glu Tyr Val Ser Gln Pro Phe Leu Met Asp Leu
                165                 170                 175

Glu Gly Lys Gln Gly Asn Phe Lys Asn Leu Arg Glu Phe Val Phe Lys
            180                 185                 190

Asn Ile Asp Gly Tyr Phe Lys Ile Tyr Ser Lys His Thr Pro Ile Asn
        195                 200                 205

Leu Val Arg Asp Leu Pro Gln Gly Phe Ser Ala Leu Glu Pro Leu Val
    210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Lys Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Glu Gly Phe Asn Cys Tyr Phe Pro Leu Gln Ser Tyr Gly Phe Gln Pro
                485                 490                 495
```

Thr Tyr Gly Val Gly Tyr Gln Pro Tyr Arg Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe
        530                 535

<210> SEQ ID NO 6
<211> LENGTH: 1614
<212> TYPE: DNA
<213> ORGANISM: Artificial Sequence
<220> FEATURE:
<223> OTHER INFORMATION: For the preparation of mRNA vaccines

<400> SEQUENCE: 6

```
atgttcgtgt tcctggtgct gctgcccctg gtgagcagcc agtgcgtgaa cctgaccacc      60
agaacccagc tgccccccgc ctacaccaac agcttcacca gaggcgtgta ctaccccgac     120
aaggtgttca agagcagcgt gctgcacagc acccaggacc tgttcctgcc cttcttcagc     180
aacgtgacct ggttccacgc catcagcggc accaacggca ccaagagatt cgacaacccc     240
gtgctgccct tcaacgacgg cgtgtacttc gccagcaccg agaagagcaa catcatcaga     300
ggctggatct tcggcaccac cctggacagc aagacccaga gcctgctgat cgtgaacaac     360
gccaccaacg tggtgatcaa ggtgtgcgag ttccagttct gcaacgaccc cttcctgggc     420
gtgtaccaca agaacaacaa gagctggatg gagagcgagt tcagagtgta cagcagcgcc     480
aacaactgca ccttcgagta cgtgagccag cccttcctga tggacctgga gggcaagcag     540
ggcaacttca agaacctgag agagttcgtg ttcaagaaca tcgacggcta cttcaagatc     600
tacagcaagc acacccccat caacctggtg agagacctgc cccagggctt cagcgccctg     660
gagcccctgg tggacctgcc catcggcatc aacatcacca gattccagac cctgctggcc     720
ctgcacagaa gctacctgac ccccggcgac agcagcagcg gctggaccgc cggcgccgcc     780
gcctactacg tgggctacct gcagcccaga accttcctgc tgaagtacaa cgagaacggc     840
accatcaccg acgccgtgga ctgcgccctg gacccccttga cgagaccaa gtgcaccctg     900
aagagcttca ccgtggagaa gggcatctac cagaccagca acttcagagt gcagcccacc     960
gagagcatcg tgagattccc caacatcacc aacctgtgcc ccttcggcga ggtgttcaac    1020
gccaccagat cgccagcgt gtacgcctgg aacagaaaga gaatcagcaa ctgcgtggcc    1080
gactacagcg tgctgtacaa cagcgccagc ttcagcacct tcaagtgcta cggcgtgagc    1140
cccaccaagc tgaacgacct gtgcttcacc aacgtgtacg ccgacagctt cgtgatcaga    1200
ggcgacgagg tgagacagat cgccccccggc cagaccggca agatcgccga ctacaactac    1260
aagctgcccg acgacttcac cggctgcgtg atcgcctgga acagcaacaa cctggacagc    1320
aaggtgggcg gcaactacaa ctacctgtac agactgttca aaagagcaa cctgaagccc    1380
ttcgagagag acatcagcac cgagatctac caggccggca gcaccccctg caacggcgtg    1440
gagggcttca actgctactt ccccctgcag agctacggct tccagcccac ctacggcgtg    1500
ggctaccagc cctacagagt ggtggtgctg agcttcgagc tgctgcacgc ccccgccacc    1560
gtgtgcggcc ccaagaagag caccaacctg gtgaagaaca gtgcgtgaa cttc          1614
```

<210> SEQ ID NO 7
<211> LENGTH: 1614
<212> TYPE: DNA
<213> ORGANISM: Artificial Sequence
<220> FEATURE:

<223> OTHER INFORMATION: For the preparation of mRNA vaccines

<400> SEQUENCE: 7

| | |
|---|---|
| atgttcgtgt tcctggtgct gctgcctctg gtgagcagcc agtgcgtgaa cctgaccacc | 60 |
| agaacccagc tgcctcctgc ctacaccaac agcttcacca gaggcgtgta ctaccctgac | 120 |
| aaggtgttca gaagcagcgt gctgcacagc acccaggacc tgttcctgcc tttcttcagc | 180 |
| aacgtgacct ggttccacgc catcagcggc accaacggca ccaagagatt cgacaaccct | 240 |
| gtgctgcctt tcaacgacgg cgtgtacttc gccagcaccg agaagagcaa catcatcaga | 300 |
| ggctggatct tcggcaccac cctggacagc aagacccaga gcctgctgat cgtgaacaac | 360 |
| gccaccaacg tggtgatcaa ggtgtgcgag ttccagttct gcaacgaccc tttcctgggc | 420 |
| gtgtaccaca gaacaacaa gagctggatg gagagcgagt tcagagtgta cagcagcgcc | 480 |
| aacaactgca ccttcgagta cgtgagccag cctttcctga tggacctgga gggcaagcag | 540 |
| ggcaacttca agaacctgag agagttcgtg ttcaagaaca tcgacggcta cttcaagatc | 600 |
| tacagcaagc acacccctat caacctggtg agagacctgc ctcagggctt cagcgccctg | 660 |
| gagcctctgg tggacctgcc tatcggcatc aacatcacca gattccagac cctgctggcc | 720 |
| ctgcacagaa gctacctgac ccctggcgac agcagcagcg gctggaccgc cggcgccgcc | 780 |
| gcctactacg tgggctacct gcagcctaga accttcctgc tgaagtacaa cgagaacggc | 840 |
| accatcaccg acgccgtgga ctgcgccctg gaccctctga gcgagaccaa gtgcaccctg | 900 |
| aagagcttca ccgtggagaa gggcatctac cagaccagca acttcagagt gcagcctacc | 960 |
| gagagcatcg tgagattccc taacatcacc aacctgtgcc ctttcggcga ggtgttcaac | 1020 |
| gccaccagat cgccagcgt gtacgcctgg aacagaaaga gaatcagcaa ctgcgtggcc | 1080 |
| gactacagcg tgctgtacaa cagcgccagc ttcagcacct tcaagtgcta cggcgtgagc | 1140 |
| cctaccaagc tgaacgacct gtgcttcacc aacgtgtacg ccgacagctt cgtgatcaga | 1200 |
| ggcgacgagg tgagacagat cgcccctggc cagaccggca agatcgccga ctacaactac | 1260 |
| aagctgcctg acgacttcac cggctgcgtg atcgcctgga acagcaacaa cctggacagc | 1320 |
| aaggtgggcg gcaactacaa ctacctgtac agactgttca gaaagagcaa cctgaagcct | 1380 |
| ttcgagagag acatcagcac cgagatctac caggccggca gcacccctg caacggcgtg | 1440 |
| gagggcttca actgctactt ccctctgcag agctacggct tccagcctac ctacggcgtg | 1500 |
| ggctaccagc cttacagagt ggtggtgctg agcttcgagc tgctgcacgc ccctgccacc | 1560 |
| gtgtgcggcc ctaagaagag caccaacctg gtgaagaaca gtgcgtgaa cttc | 1614 |

<210> SEQ ID NO 8
<211> LENGTH: 1614
<212> TYPE: DNA
<213> ORGANISM: Artificial Sequence
<220> FEATURE:
<223> OTHER INFORMATION: For the preparation of mRNA vaccines

<400> SEQUENCE: 8

| | |
|---|---|
| atgttcgtgt tcctggtgct gctgcccctg gtgagcagcc agtgcgtgaa cctgaccacc | 60 |
| aggacccagc tgccccccgc ctacaccaac agcttcacca gggcgtgta ctaccccgac | 120 |
| aaggtgttca ggagcagcgt gctgcacagc acccaggacc tgttcctgcc cttcttcagc | 180 |
| aacgtgacct ggttccacgc catcagcggc accaacggca ccaagaggtt cgacaacccc | 240 |
| gtgctgccct tcaacgacgg cgtgtacttc gccagcaccg agaagagcaa catcatcagg | 300 |
| ggctggatct tcggcaccac cctggacagc aagacccaga gcctgctgat cgtgaacaac | 360 |

```
gccaccaacg tggtgatcaa ggtgtgcgag ttccagttct gcaacgaccc cttcctgggc    420
gtgtaccaca agaacaacaa gagctggatg gagagcgagt tcagggtgta cagcagcgcc    480
aacaactgca ccttcgagta cgtgagccag cccttcctga tggacctgga gggcaagcag    540
ggcaacttca agaacctgag ggagttcgtg ttcaagaaca tcgacggcta cttcaagatc    600
tacagcaagc acaccccat caacctggtg agggacctgc cccagggctt cagcgccctg    660
gagcccctgg tggacctgcc catcggcatc aacatcacca ggttccagac cctgctggcc    720
ctgcacagga gctacctgac ccccggcgac agcagcagcg gctggaccgc ggcgccgcc    780 gcctactacg tgggctacct gcagcccagg accttcctgc tgaagtacaa cgagaacggc    840
accatcaccg acgccgtgga ctgcgccctg gaccccctga gcgagaccaa gtgcacctg    900 aagagcttca ccgtggagaa gggcatctac cagaccagca acttcagggt gcagcccacc    960
gagagcatcg tgaggttccc caacatcacc aacctgtgcc ccttcggcga ggtgttcaac   1020
gccaccaggt tcgccagcgt gtacgcctgg aacaggaaga ggatcagcaa ctgcgtggcc   1080
gactacagcg tgctgtacaa cagcgccagc ttcagcacct tcaagtgcta cggcgtgagc   1140
cccaccaagc tgaacgacct gtgcttcacc aacgtgtacg ccgacagctt cgtgatcagg   1200
ggcgacgagg tgaggcagat cgcccccggc cagaccggca agatcgccga ctacaactac   1260
aagctgcccg acgacttcac cggctgcgtg atcgcctgga acagcaacaa cctggacagc   1320
aaggtgggcg gcaactacaa ctacctgtac aggctgttca ggaagagcaa cctgaagccc   1380
ttcgagaggg acatcagcac cgagatctac caggccggca gcaccccctg caacggcgtg   1440
gagggcttca actgctactt ccccctgcag agctacggct ccagcccac ctacggcgtg   1500 ggctaccagc cctacagggt ggtggtgctg agcttcgagc tgctgcacgc ccccgccacc   1560
gtgtgcggcc ccaagaagag caccaacctg gtgaagaaca gtgcgtgaa cttc         1614
```

<210> SEQ ID NO 9
<211> LENGTH: 539
<212> TYPE: PRT
<213> ORGANISM: Artificial Sequence
<220> FEATURE:
<223> OTHER INFORMATION: Antigen

<400> SEQUENCE: 9

```
Met Phe Val Phe Leu Val Leu Leu Pro Leu Val Ser Ser Gln Cys Val
1               5                  10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Ala
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
        130                 135                 140
```

-continued

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
    195                 200                 205

Pro Ile Asn Leu Val Arg Gly Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu His Arg Ser Tyr Leu Thr Pro Gly Asp Ser Ser Ser Gly Trp
                245                 250                 255

Thr Ala Gly Ala Ala Ala Tyr Tyr Val Gly Tyr Leu Gln Pro Arg Thr
            260                 265                 270

Phe Leu Leu Lys Tyr Asn Glu Asn Gly Thr Ile Thr Asp Ala Val Asp
        275                 280                 285

Cys Ala Leu Asp Pro Leu Ser Glu Thr Lys Cys Thr Leu Lys Ser Phe
290                 295                 300

Thr Val Glu Lys Gly Ile Tyr Gln Thr Ser Asn Phe Arg Val Gln Pro
305                 310                 315                 320

Thr Glu Ser Ile Val Arg Phe Pro Asn Ile Thr Asn Leu Cys Pro Phe
                325                 330                 335

Gly Glu Val Phe Asn Ala Thr Arg Phe Ala Ser Val Tyr Ala Trp Asn
            340                 345                 350

Arg Lys Arg Ile Ser Asn Cys Val Ala Asp Tyr Ser Val Leu Tyr Asn
        355                 360                 365

Ser Ala Ser Phe Ser Thr Phe Lys Cys Tyr Gly Val Ser Pro Thr Lys
370                 375                 380

Leu Asn Asp Leu Cys Phe Thr Asn Val Tyr Ala Asp Ser Phe Val Ile
385                 390                 395                 400

Arg Gly Asp Glu Val Arg Gln Ile Ala Pro Gly Gln Thr Gly Asn Ile
                405                 410                 415

Ala Asp Tyr Asn Tyr Lys Leu Pro Asp Asp Phe Thr Gly Cys Val Ile
            420                 425                 430

Ala Trp Asn Ser Asn Asn Leu Asp Ser Lys Val Gly Gly Asn Tyr Asn
        435                 440                 445

Tyr Leu Tyr Arg Leu Phe Arg Lys Ser Asn Leu Lys Pro Phe Glu Arg
450                 455                 460

Asp Ile Ser Thr Glu Ile Tyr Gln Ala Gly Ser Thr Pro Cys Asn Gly
465                 470                 475                 480

Val Lys Gly Phe Asn Cys Tyr Phe Pro Leu Gln Ser Tyr Gly Phe Gln
                485                 490                 495

Pro Thr Tyr Gly Val Gly Tyr Gln Pro Tyr Arg Val Val Val Leu Ser
            500                 505                 510

Phe Glu Leu Leu His Ala Pro Ala Thr Val Cys Gly Pro Lys Lys Ser
        515                 520                 525

Thr Asn Leu Val Lys Asn Lys Cys Val Asn Phe
530                 535

<210> SEQ ID NO 10
<211> LENGTH: 1617
```

```
<212> TYPE: DNA
<213> ORGANISM: Artificial Sequence
<220> FEATURE:
<223> OTHER INFORMATION: For the preparation of mRNA vaccines

<400> SEQUENCE: 10
atgttcgtgt tcctggtgct gctgcccctg gtgagcagcc agtgcgtgaa cctgaccacc      60
aggacccagc tgccccccgc ctacaccaac agcttcacca ggggcgtgta ctaccccgac     120
aaggtgttca ggagcagcgt gctgcacagc acccaggacc tgttcctgcc cttcttcagc     180
aacgtgacct ggttccacgc catccacgtg agcggcacca acggcaccaa gaggttcgcc     240
aaccccgtgc tgcccttcaa cgacggcgtg tacttcgcca gcaccgagaa gagcaacatc     300
atcaggggct ggatcttcgg caccaccctg gacagcaaga cccagagcct gctgatcgtg     360
aacaacgcca ccaacgtggt gatcaaggtg tgcgagttcc agttctgcaa cgaccccttc     420
ctgggcgtgt actaccacaa gaacaacaag agctggatgg agagcgagtt cagggtgtac     480
agcagcgcca acaactgcac cttcgagtac gtgagccagc ccttcctgat ggacctggag     540
ggcaagcagg gcaacttcaa gaacctgagg gagttcgtgt tcaagaacat cgacggctac     600
ttcaagatct acagcaagca cacccccatc aacctggtga ggggcctgcc ccagggcttc     660
agcgccctgg agcccctggt ggacctgccc atcggcatca acatcaccag gttccagacc     720
ctgctgcaca ggagctacct gacccccggc gacagcagca gcggctggac cgccggcgcc     780
gccgcctact acgtgggcta cctgcagccc aggaccttcc tgctgaagta caacgagaac     840
ggcaccatca ccgacgccgt ggactgcgcc ctggaccccc tgagcgagac caagtgcacc     900
ctgaagagct tcaccgtgga aagggcatc taccagacca gcaacttcag ggtgcagccc     960
accgagagca tcgtgaggtt ccccaacatc accaacctgt gccccttcgg cgaggtgttc    1020
aacgccacca ggttcgccag cgtgtacgcc tggaacagga gaggatcag caactgcgtg    1080 gccgactaca gcgtgctgta caacagcgcc agcttcagca ccttcaagtg ctacggcgtg    1140
agccccacca agctgaacga cctgtgcttc accaacgtgt acgccgacag cttcgtgatc    1200
aggggcgacg aggtgaggca gatcgccccc ggccagaccg gcaacatcgc cgactacaac    1260
tacaagctgc ccgacgactt caccggctgc gtgatcgcct ggaacagcaa caacctggac    1320
agcaaggtgg gcggcaacta caactacctg tacaggctgt tcaggaagag caacctgaag    1380
cccttcgaga gggacatcag caccgagatc taccaggccg gcagcacccc ctgcaacggc    1440
gtgaagggct tcaactgcta cttccccctg cagagctacg gcttccagcc cacctacggc    1500
gtgggctacc agccctacag ggtggtggtg ctgagcttcg agctgctgca cgcccccgcc    1560
accgtgtgcg gccccaagaa gagcaccaac ctggtgaaga caagtgcgt gaacttc       1617

<210> SEQ ID NO 11
<211> LENGTH: 1617
<212> TYPE: DNA
<213> ORGANISM: Artificial Sequence
<220> FEATURE:
<223> OTHER INFORMATION: For the preparation of mRNA vaccines

<400> SEQUENCE: 11
atgttcgtgt tcctggtgct gctgcctctg gtgagcagcc agtgcgtgaa cctgaccacc      60
aggacccagc tgcctcctgc ctacaccaac agcttcacca ggggcgtgta ctaccctgac     120
aaggtgttca ggagcagcgt gctgcacagc acccaggacc tgttcctgcc ctttcttcagc    180 aacgtgacct ggttccacgc catccacgtg agcggcacca acggcaccaa gaggttcgcc     240
```

| | |
|---|---|
| aaccctgtgc tgcctttcaa cgacggcgtg tacttcgcca gcaccgagaa gagcaacatc | 300 |
| atcaggggct ggatcttcgg caccaccctg acagcaaga cccagagcct gctgatcgtg | 360 |
| aacaacgcca ccaacgtggt gatcaaggtg tgcgagttcc agttctgcaa cgacccttc | 420 |
| ctgggcgtgt actaccacaa gaacaacaag agctggatgg agagcgagtt cagggtgtac | 480 |
| agcagcgcca caactgcac cttcgagtac gtgagccagc ctttcctgat ggacctggag | 540 |
| ggcaagcagg gcaacttcaa gaacctgagg gagttcgtgt tcaagaacat cgacggctac | 600 |
| ttcaagatct acagcaagca cacccctatc aacctggtga ggggcctgcc tcagggcttc | 660 |
| agcgccctgg agcctctggt ggacctgcct atcggcatca acatcaccag gttccagacc | 720 |
| ctgctgcaca ggagctacct gaccctggc acagcagca gcggctggac cgccggcgcc | 780 |
| gccgcctact acgtgggcta cctgcagcct aggaccttcc tgctgaagta caacgagaac | 840 |
| ggcaccatca ccgacgccgt ggactgcgcc ctggaccctc tgagcgagac caagtgcacc | 900 |
| ctgaagagct tcaccgtgga aagggcatc taccagacca gcaacttcag ggtgcagcct | 960 |
| accgagagca tcgtgaggtt ccctaacatc accaacctgt gccctttcgg cgaggtgttc | 1020 |
| aacgccacca ggttcgccag cgtgtacgcc tggaacagga gaggatcag caactgcgtg | 1080 |
| gccgactaca gcgtgctgta caacagcgcc agcttcagca ccttcaagtg ctacggcgtg | 1140 |
| agccctacca gctgaacga cctgtgcttc accaacgtgt acgccgacag cttcgtgatc | 1200 |
| aggggcgacg aggtgaggca gatcgcccct ggccagaccg caacatcgc cgactacaac | 1260 |
| tacaagctgc ctgacgactt caccggctgc gtgatcgcct ggaacagcaa caacctggac | 1320 |
| agcaaggtgg gcggcaacta caactacctg tacaggctgt tcaggaagag caacctgaag | 1380 |
| cctttcgaga gggacatcag caccgagatc taccaggccg gcagcacccc ttgcaacggc | 1440 |
| gtgaagggct tcaactgcta cttccctctg cagagctacg gcttccagcc tacctacggc | 1500 |
| gtgggctacc agccttacag ggtggtggtg ctgagcttcg agctgctgca cgcccctgcc | 1560 |
| accgtgtgcg gccctaagaa gagcaccaac ctggtgaaga caagtgcgt gaacttc | 1617 |

<210> SEQ ID NO 12
<211> LENGTH: 1617
<212> TYPE: DNA
<213> ORGANISM: Artificial Sequence
<220> FEATURE:
<223> OTHER INFORMATION: For the preparation of mRNA vaccines

<400> SEQUENCE: 12

| | |
|---|---|
| atgttcgtgt tcctggtgct gctgcccctg gtgagcagcc agtgcgtgaa cctgaccacc | 60 |
| aggacccagc tgccccccgc ctacaccaac agcttcacca ggggcgtgta ctaccccgac | 120 |
| aaggtgttca ggagcagcgt gctgcacagc acccaggacc tgttcctgcc cttcttcagc | 180 |
| aacgtgacct ggttccacgc catccacgtg agcggcacca acggcaccaa gaggttcgcc | 240 |
| aaccccgtgc tgcccttcaa cgacggcgtg tacttcgcca gcaccgagaa gagcaacatc | 300 |
| atcaggggct ggatcttcgg caccaccctg acagcaaga cccagagcct gctgatcgtg | 360 |
| aacaacgcca ccaacgtggt gatcaaggtg tgcgagttcc agttctgcaa cgacccttc | 420 |
| ctgggcgtgt actaccacaa gaacaacaag agctggatgg agagcgagtt cagggtgtac | 480 |
| agcagcgcca caactgcac cttcgagtac gtgagccagc ctttcctgat ggacctggag | 540 |
| ggcaagcagg gcaacttcaa gaacctgagg gagttcgtgt tcaagaacat cgacggctac | 600 |
| ttcaagatct acagcaagca cacccctatc aacctggtga ggggcctgcc ccagggcttc | 660 |
| agcgccctgg agcccctggt ggacctgccc atcggcatca acatcaccag gttccagacc | 720 |

```
ctgctgcaca ggagctacct gaccccggc gacagcagca gcggctggac cgccggcgcc    780
gccgcctact acgtgggcta cctgcagccc aggaccttcc tgctgaagta caacgagaac    840
ggcaccatca ccgacgccgt ggactgcgcc ctggaccccc tgagcgagac caagtgcacc    900
ctgaagagct tcaccgtgga agggcatc taccagacca gcaacttcag ggtgcagccc    960
accgagagca tcgtgaggtt ccccaacatc accaacctgt gccccttcgg cgaggtgttc   1020
aacgccacca ggttcgccag cgtgtacgcc tggaacagga gaggatcag caactgcgtg   1080
gccgactaca gcgtgctgta caacagcgcc agcttcagca ccttcaagtg ctacggcgtg   1140
agccccacca agctgaacga cctgtgcttc accaacgtgt acgccgacag cttcgtgatc   1200
aggggcgacg aggtgaggca gatcgccccc ggccagaccg gcaacatcgc cgactacaac   1260
tacaagctgc ccgacgactt caccggctgc gtgatcgcct ggaacagcaa caacctggac   1320
agcaaggtgg gcggcaacta caactacctg tacaggctgt tcaggaagag caacctgaag   1380
cccttcgaga gggacatcag caccgagatc taccaggccg gcagcacccc ctgcaacggc   1440
gtgaagggct tcaactgcta cttcccctg cagagctacg gcttccagcc cacctacggc   1500
gtgggctacc agccctacag ggtggtggtg ctgagcttcg agctgctgca cgcccccgcc   1560
accgtgtgcg gccccaagaa gagcaccaac ctggtgaaga caagtgcgt gaacttc      1617
```

<210> SEQ ID NO 13
<211> LENGTH: 541
<212> TYPE: PRT
<213> ORGANISM: Artificial Sequence
<220> FEATURE:
<223> OTHER INFORMATION: Antigen

<400> SEQUENCE: 13

```
Met Phe Val Phe Leu Val Leu Leu Pro Leu Val Ser Ser Gln Cys Val
1               5                   10                  15

Asn Phe Thr Asn Arg Thr Gln Leu Pro Ser Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Tyr Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Ser Glu Phe
            180                 185                 190

Val Phe Lys Asn Ile Asp Gly Tyr Phe Lys Ile Tyr Ser Lys His Thr
        195                 200                 205
```

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Thr Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe
530                 535                 540

<210> SEQ ID NO 14
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 14
atgttcgtgt tcctggtgct gctgcccctg gtgagcagcc agtgcgtgaa cttcaccaac     60
agaacccagc tgcccagcgc ctacaccaac agcttcacca gaggcgtgta ctaccccgac    120
aaggtgttca gaagcagcgt gctgcacagc acccaggacc tgttcctgcc cttcttcagc    180

```
aacgtgacct ggttccacgc catccacgtg agcggcacca acggcaccaa gagattcgac    240
aaccccgtgc tgcccttcaa cgacggcgtg tacttcgcca gcaccgagaa gagcaacatc    300
atcagaggct ggatcttcgg caccaccctg acagcaagaa cccagagcct gctgatcgtg    360
aacaacgcca ccaacgtggt gatcaaggtg tgcgagttcc agttctgcaa ctacccttc     420 ctgggcgtgt actaccacaa gaacaacaag agctggatgg agagcgagtt cagagtgtac    480
agcagcgcca caactgcac cttcgagtac gtgagccagc ccttcctgat ggacctggag     540
ggcaagcagg gcaacttcaa gaacctgagc gagttcgtgt tcaagaacat cgacggctac    600
ttcaagatct acagcaagca cacccccatc aacctggtga gagacctgcc ccagggcttc    660
agcgccctgg agccctggt ggacctgccc atcggcatca acatcaccag attccagacc     720
ctgctggccc tgcacagaag ctacctgacc cccggcgaca gcagcagcgg ctggaccgcc    780
ggcgccgccg cctactacgt gggctacctg cagcccagaa ccttcctgct gaagtacaac    840
gagaacggca ccatcaccga cgccgtggac tgcgccctgg accccctgag cgagaccaag    900
tgcaccctga gagcttcac cgtggagaag gcatctacc agaccagcaa cttcagagtg      960
cagcccaccg agagcatcgt gagattcccc aacatcacca acctgtgccc cttcggcgag   1020
gtgttcaacg ccaccagatt cgccagcgtg tacgcctgga acagaaagag aatcagcaac   1080
tgcgtggccg actacagcgt gctgtacaac agcgccagct tcagcacctt caagtgctac   1140
ggcgtgagcc ccaccaagct gaacgacctg tgcttcacca acgtgtacgc cgacagcttc   1200
gtgatcagag cgacgaggt gagacagatc gcccccggcc agaccggcac catcgccgac   1260
tacaactaca agctgcccga cgacttcacc ggctgcgtga tcgcctggaa cagcaacaac   1320
ctggacagca aggtgggcgg caactacaac tacctgtaca gactgttcag aaagagcaac   1380
ctgaagccct tcgagagaga catcagcacc gagatctacc aggccggcag caccccctgc   1440
aacggcgtga agggcttcaa ctgctacttc ccctgcaga gctacggctt ccagcccacc   1500
tacggcgtgg gctaccagcc ctacagagtg gtggtgctga gcttcgagct gctgcacgcc   1560
cccgccaccg tgtgcggccc caagaagagc accaacctgg tgaagaacaa gtgcgtgaac   1620
ttc                                                                 1623
```

<210> SEQ ID NO 15
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 15

```
atgttcgtgt tcctggtgct gctgcctctg gtgagcagcc agtgcgtgaa cttcaccaac     60
agaacccagc tgcctagcgc ctacaccaac agcttcacca gaggcgtgta ctaccctgac    120
aaggtgttca gaagcagcgt gctgcacagc acccaggacc tgttcctgcc tttcttcagc    180
aacgtgacct ggttccacgc catccacgtg agcggcacca acggcaccaa gagattcgac    240
aaccctgtgc tgccttttcaa cgacggcgtg tacttcgcca gcaccgagaa gagcaacatc    300
atcagaggct ggatcttcgg caccaccctg acagcaagaa cccagagcct gctgatcgtg    360
aacaacgcca ccaacgtggt gatcaaggtg tgcgagttcc agttctgcaa ctacccttc     420 ctgggcgtgt actaccacaa gaacaacaag agctggatgg agagcgagtt cagagtgtac    480
agcagcgcca caactgcac cttcgagtac gtgagccagc ctttcctgat ggacctggag     540
```

```
ggcaagcagg gcaacttcaa gaacctgagc gagttcgtgt tcaagaacat cgacggctac    600
ttcaagatct acagcaagca cccccctatc aacctggtga gagacctgcc tcagggcttc    660
agcgccctgg agcctctggt ggacctgcct atcggcatca acatcaccag attccagacc    720
ctgctggccc tgcacagaag ctacctgacc cctggcgaca gcagcagcgg ctggaccgcc    780
ggcgccgccg cctactacgt gggctacctg cagcctagaa ccttcctgct gaagtacaac    840
gagaacggca ccatcaccga cgccgtggac tgcgccctgg accctctgag cgagaccaag    900
tgcaccctga agagcttcac cgtggagaag ggcatctacc agaccagcaa cttcagagtg    960
cagcctaccg agagcatcgt gagattccct aacatcacca acctgtgccc tttcggcgag   1020
gtgttcaacg ccaccagatt cgccagcgtg tacgcctgga acagaaagag aatcagcaac   1080
tgcgtggccg actacagcgt gctgtacaac agcgccagct tcagcacctt caagtgctac   1140
ggcgtgagcc ctaccaagct gaacgacctg tgcttcacca acgtgtacgc cgacagcttc   1200
gtgatcagag cgacgaggt gagacagatc gcccctggcc agaccggcac catcgccgac   1260
tacaactaca agctgcctga cgacttcacc ggctgcgtga tcgcctggaa cagcaacaac   1320
ctggacagca aggtgggcgg caactacaac tacctgtaca gactgttcag aaagagcaac   1380
ctgaagcctt tcgagagaga catcagcacc gagatctacc aggccggcag cacccccttgc   1440 aacggcgtga agggcttcaa ctgctacttc cctctgcaga gctacggctt ccagcctacc   1500
tacggcgtgg gctaccagcc ttacagagtg gtggtgctga gcttcgagct gctgcacgcc   1560
cctgccaccg tgtgcggccc taagaagagc accaacctgg tgaagaacaa gtgcgtgaac   1620
ttc                                                                  1623
```

<210> SEQ ID NO 16
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 16

```
atgttcgtgt tcctggtgct gctgcccctg gtgagcagcc agtgcgtgaa cttcaccaac     60
aggacccagc tgcccagcgc ctacaccaac agcttcacca ggggcgtgta ctaccccgac    120
aaggtgttca ggagcagcgt gctgcacagc acccaggacc tgttcctgcc cttcttcagc    180
aacgtgacct ggttccacgc catccacgtg agcggcacca acggcaccaa gaggttcgac    240
aaccccgtgc tgcccttcaa cgacggcgtg tacttcgcca gcaccgagaa gagcaacatc    300
atcaggggct ggatcttcgg caccaccctg gacagcaaga cccagagcct gctgatcgtg    360
aacaacgcca ccaacgtggt gatcaaggtg tgcgagttcc agttctgcaa ctaccccttc    420
ctgggcgtgt actaccacaa gaacaacaag agctggatgg agagcgagtt cagggtgtac    480
agcagcgcca acaactgcac cttcgagtac gtgagccagc ccttcctgat ggacctggag    540
ggcaagcagg gcaacttcaa gaacctgagc gagttcgtgt tcaagaacat cgacggctac    600
ttcaagatct acagcaagca ccccccatc aacctggtga gggacctgcc ccagggcttc    660
agcgccctgg agccctggt ggacctgccc atcggcatca acatcaccag gttccagacc    720
ctgctggccc tgcacaggag ctacctgacc cccggcgaca gcagcagcgg ctggaccgcc    780
ggcgccgccg cctactacgt gggctacctg cagcccagga ccttcctgct gaagtacaac    840
gagaacggca ccatcaccga cgccgtggac tgcgccctgg acccctgag cgagaccaag    900 tgcaccctga agagcttcac cgtggagaag ggcatctacc agaccagcaa cttcagggtg    960
```

```
cagcccaccg agagcatcgt gaggttcccc aacatcacca acctgtgccc cttcggcgag   1020
gtgttcaacg ccaccaggtt cgccagcgtg tacgcctgga caggaagag gatcagcaac    1080 tgcgtggccg actacagcgt gctgtacaac agcgccagct tcagcacctt caagtgctac   1140
ggcgtgagcc ccaccaagct gaacgacctg tgcttcacca acgtgtacgc cgacagcttc   1200
gtgatcaggg gcgacgaggt gaggcagatc gcccccggcc agaccggcac catcgccgac   1260
tacaactaca agctgcccga cgacttcacc ggctgcgtga tcgcctggaa cagcaacaac   1320
ctggacagca aggtgggcgg caactacaac tacctgtaca ggctgttcag gaagagcaac   1380
ctgaagccct tcgagaggga catcagcacc gagatctacc aggccggcag cacccccctgc  1440 aacggcgtga agggcttcaa ctgctacttc cccctgcaga gctacggctt ccagcccacc   1500 tacgcgtgg gctaccagcc ctacagggtg gtggtgctga gcttcgagct gctgcacgcc    1560
cccgccaccg tgtgcggccc caagaagagc accaacctgg tgaagaacaa gtgcgtgaac   1620
ttc                                                                 1623
```

<210> SEQ ID NO 17
<211> LENGTH: 541
<212> TYPE: PRT
<213> ORGANISM: Artificial Sequence
<220> FEATURE:
<223> OTHER INFORMATION: Antigen

<400> SEQUENCE: 17

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

Leu Leu Ala Leu His Arg Ser Tyr Leu Thr Pro Gly Asp Ser Ser
                245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Arg Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe
    530                 535                 540

<210> SEQ ID NO 18
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 18
atgttcgtgt tcctggtgct gctgcccctg gtgagcagcc agtgcgtgaa cctgaccacc    60
agaacccagc tgccccccgc ctacaccaac agcttcacca gaggcgtgta ctaccccgac   120
aaggtgttca agagcagcgt gctgcacagc acccaggacc tgttcctgcc cttcttcagc   180
aacgtgacct ggttccacgc catccacgtg agcggcacca acggcaccaa gagattcgac   240
aaccccgtgc tgcccttcaa cgacggcgtg tacttcgcca gcaccgagaa gagcaacatc   300
atcagaggct ggatcttcgg caccaccctg gacagcaaga cccagagcct gctgatcgtg   360

```
aacaacgcca ccaacgtggt gatcaaggtg tgcgagttcc agttctgcaa cgacccttc      420 ctgggcgtgt actaccacaa gaacaacaag agctggatgg agagcgagtt cagagtgtac     480
agcagcgcca acaactgcac cttcgagtac gtgagccagc ccttcctgat ggacctggag     540
ggcaagcagg gcaacttcaa gaacctgaga gagttcgtgt tcaagaacat cgacggctac     600
ttcaagatct acagcaagca cacccccatc aacctggtga gagacctgcc ccagggcttc     660
agcgccctgg agcccctggt ggacctgccc atcggcatca acatcaccag attccagacc     720
ctgctggccc tgcacagaag ctacctgacc cccggcgaca gcagcagcgg ctggaccgcc     780
ggcgccgccc cctactacgt gggctacctg cagcccagaa ccttcctgct gaagtacaac     840
gagaacggca ccatcaccga cgccgtggac tgcgccctgg acccctgag cgagaccaag      900 tgcacccctg agagcttcac cgtggagaag ggcatctacc agaccagcaa cttcagagtg     960
cagcccaccg agagcatcgt gagattcccc aacatcacca cctgtgccc cttcggcgag     1020 gtgttcaacg ccaccagatt cgccagcgtg tacgcctgga cagaaagag aatcagcaac     1080 tgcgtggccg actacagcgt gctgtacaac agcgccagct cagcaccttc aagtgctac      1140 ggcgtgagcc ccaccaagct gaacgacctg tgcttcacca cgtgtacgc cgacagcttc      1200 gtgatcagag gcgacgaggt gagacagatc gcccccggcc agaccggcaa gatcgccgac     1260
tacaactaca gctgcccga cgacttcacc ggctgcgtga tcgcctggaa cagcaacaac      1320
ctggacagca aggtgggcgg caactacaac tacagataca gactgttcag aaagagcaac     1380
ctgaagccct tcgagagaga catcagcacc gagatctacc aggccggcag caccccctgc     1440
aacggcgtgg agggcttcaa ctgctacttc ccctgcaga gctacggctt ccagcccacc     1500
aacggcgtgg gctaccagcc ctacagagtg gtggtgctga gcttcgagct gctgcacgcc     1560
cccgccaccg tgtgcggccc caagaagagc accaacctgg tgaagaacaa gtgcgtgaac     1620
ttc                                                                    1623

<210> SEQ ID NO 19
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 19
atgttcgtgt tcctggtgct gctgcctctg gtgagcagcc agtgcgtgaa cctgaccacc      60
agaacccagc tgcctcctgc ctacaccaac agcttcacca gaggcgtgta ctaccctgac     120
aaggtgttca gaagcagcgt gctgcacagc acccaggacc tgttcctgcc tttcttcagc     180
aacgtgacct ggttccacgc catccacgtg agcggcacca cggcaccaa gagattcgac     240 aaccctgtgc tgccttttcaa cgacggcgtg tacttcgcca gcaccgagaa gagcaacatc     300
atcagaggct ggatcttcgg caccaccctg gacagcaaga cccagagcct gctgatcgtg     360
aacaacgcca ccaacgtggt gatcaaggtg tgcgagttcc agttctgcaa cgacccttc      420 ctgggcgtgt actaccacaa gaacaacaag agctggatgg agagcgagtt cagagtgtac     480
agcagcgcca caactgcac cttcgagtac gtgagccagc cttcctgat ggacctggag       540 ggcaagcagg gcaacttcaa gaacctgaga gagttcgtgt tcaagaacat cgacggctac     600
ttcaagatct acagcaagca cacccctatc aacctggtga gagacctgcc tcagggcttc     660
agcgccctgg agcctctggt ggacctgcct atcggcatca acatcaccag attccagacc     720
```

```
ctgctggccc tgcacagaag ctacctgacc cctggcgaca gcagcagcgg ctggaccgcc      780
ggcgccgccg cctactacgt gggctacctg cagcctagaa ccttcctgct gaagtacaac      840
gagaacggca ccatcaccga cgccgtggac tgcgccctgg accctctgag cgagaccaag      900
tgcaccctga gagcttcac cgtggagaag ggcatctacc agaccagcaa cttcagagtg       960
cagcctaccg agagcatcgt gagattccct aacatcacca acctgtgccc tttcggcgag     1020
gtgttcaacg ccaccagatt cgccagcgtg tacgcctgga acagaaagag aatcagcaac     1080
tgcgtggccg actacagcgt gctgtacaac agcgccagct tcagcacctt caagtgctac     1140
ggcgtgagcc ctaccaagct gaacgacctg tgcttcacca cgtgtacgc cgacagcttc      1200
gtgatcagag cgacgaggt gagacagatc gcccctggcc agaccggcaa gatcgccgac      1260
tacaactaca gctgcctga cgacttcacc ggctgcgtga tcgcctggaa cagcaacaac      1320
ctggacagca aggtgggcgg caactacaac tacagataca gactgttcag aaagagcaac     1380
ctgaagcctt tcgagagaga catcagcacc gagatctacc aggccggcag cacccccttgc    1440
aacggcgtgg agggcttcaa ctgctacttc cctctgcaga gctacggctt ccagcctacc     1500
aacggcgtgg gctaccagcc ttacagagtg tggtgctga gcttcgagct gctgcacgcc      1560
cctgccaccg tgtgcggccc taagaagagc accaacctgg tgaagaacaa gtgcgtgaac    1620
ttc                                                                   1623

<210> SEQ ID NO 20
<211> LENGTH: 1623
<212> TYPE: DNA
<213> ORGANISM: Artificial Sequence
<220> FEATURE:
<223> OTHER INFORMATION: For the preparation of mRNA vaccines

<400> SEQUENCE: 20
atgttcgtgt tcctggtgct gctgcccctg gtgagcagcc agtgcgtgaa cctgaccacc       60
aggacccagc tgccccccgc ctacaccaac agcttcacca ggggcgtgta ctaccccgac      120
aaggtgttca ggagcagcgt gctgcacagc acccaggacc tgttcctgcc cttcttcagc      180
aacgtgacct ggttccacgc catccacgtg agcggcacca cggcaccaa gaggttcgac       240
aaccccgtgc tgcccttcaa cgacggcgtg tacttcgcca gcaccgagaa gagcaacatc     300
atcaggggct ggatcttcgg caccaccctg gacagcaaga cccagagcct gctgatcgtg     360
aacaacgcca ccaacgtggt gatcaaggtg tgcgagttcc agttctgcaa cgacccctc      420
ctgggcgtgt actaccacaa gaacaacaag agctggatgg agagcgagtt cagggtgtac     480
agcagcgcca acaactgcac cttcgagtac gtgagccagc ccttcctgat ggacctggag     540
ggcaagcagg gcaacttcaa gaacctgagg gagttcgtgt tcaagaacat cgacggctac     600
ttcaagatct acagcaagca ccccccatc aacctggtga gggacctgcc ccagggcttc     660
agcgccctgg agccctggt ggacctgccc atcggcatca acatcaccag gttccagacc     720
ctgctggccc tgcacaggag ctacctgacc cccggcgaca gcagcagcgg ctggaccgcc     780
ggcgccgccg cctactacgt gggctacctg cagcccagga ccttcctgct gaagtacaac    840
gagaacggca ccatcaccga cgccgtggac tgcgccctgg accccctgag cgagaccaag    900
tgcaccctga gagcttcac cgtggagaag ggcatctacc agaccagcaa cttcagggtg      960
cagcccaccg agagcatcgt gaggttcccc aacatcacca acctgtgccc cttcggcgag   1020
gtgttcaacg ccaccaggtt cgccagcgtg tacgcctgga caggaagag gatcagcaac    1080
tgcgtggccg actacagcgt gctgtacaac agcgccagct tcagcacctt caagtgctac    1140
```

```
ggcgtgagcc ccaccaagct gaacgacctg tgcttcacca acgtgtacgc cgacagcttc    1200
gtgatcaggg gcgacgaggt gaggcagatc gcccccggcc agaccggcaa gatcgccgac    1260
tacaactaca agctgcccga cgacttcacc ggctgcgtga tcgcctggaa cagcaacaac    1320
ctggacagca aggtgggcgg caactacaac tacaggtaca ggctgttcag gaagagcaac    1380
ctgaagccct tcgagaggga catcagcacc gagatctacc aggccggcag caccccctgc    1440
aacggcgtgg agggcttcaa ctgctacttc cccctgcaga gctacggctt ccagcccacc    1500
aacggcgtgg gctaccagcc ctacagggtg gtggtgctga cttcgagct gctgcacgcc    1560 cccgccaccg tgtgcggccc caagaagagc accaacctgg tgaagaacaa gtgcgtgaac    1620
ttc                                                                  1623
```

<210> SEQ ID NO 21
<211> LENGTH: 538
<212> TYPE: PRT
<213> ORGANISM: Artificial Sequence
<220> FEATURE:
<223> OTHER INFORMATION: Antigen

<400> SEQUENCE: 21

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Val Ile Ser Gly Thr Asn Gly Thr Lys Arg Phe Asp Asn Pro
65                  70                  75                  80

Val Leu Pro Phe Asn Asp Gly Val Tyr Phe Ala Ser Ile Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Asp His Lys Asn Asn
    130                 135                 140

Lys Ser Trp Met Glu Ser Glu Phe Arg Val Tyr Ser Ser Ala Asn Asn
145                 150                 155                 160

Cys Thr Phe Glu Tyr Val Ser Gln Pro Phe Leu Met Asp Leu Glu Gly
                165                 170                 175

Lys Gln Gly Asn Phe Lys Asn Leu Arg Glu Phe Val Phe Lys Asn Ile
            180                 185                 190

Asp Gly Tyr Phe Lys Ile Tyr Ser Lys His Thr Pro Ile Ile Val Arg
        195                 200                 205

Glu Pro Glu Asp Leu Pro Gln Gly Phe Ser Ala Leu Glu Pro Leu Val
    210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270
```

```
Leu Leu Lys Tyr Asn Glu Asn Gly Thr Ile Thr Asp Ala Val Asp Cys
            275                 280                 285

Ala Leu Asp Pro Leu Ser Glu Thr Lys Cys Thr Leu Lys Ser Phe Thr
        290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Asp
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Leu
        355                 360                 365

Ala Pro Phe Phe Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Asn Ile Ala
                405                 410                 415

Asp Tyr Asn Tyr Lys Leu Pro Asp Asp Phe Thr Gly Cys Val Ile Ala
            420                 425                 430

Trp Asn Ser Asn Lys Leu Asp Ser Lys Val Ser Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Asn Lys Pro Cys Asn Gly Val
465                 470                 475                 480

Ala Gly Phe Asn Cys Tyr Phe Pro Leu Arg Ser Tyr Ser Phe Arg Pro
                485                 490                 495

Thr Tyr Gly Val Gly His Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe
    530                 535

<210> SEQ ID NO 22
<211> LENGTH: 1620
<212> TYPE: DNA
<213> ORGANISM: Artificial Sequence
<220> FEATURE:
<223> OTHER INFORMATION: For the preparation of mRNA vaccines

<400> SEQUENCE: 22
atgtttgtgt tcctggtgct gctgcccctg gtgagcagcc agtgcgtgaa cctgaccacc        60
agaacacagc tgcctcccgc ctacaccaac tccttcaccc gcggcgtgta ctaccctgat       120
aaggtgttca ggagctccgt gctgcacagc acccaggacc tgttcctgcc tttcttctct       180
aacgtgacct ggttccacgt gattagcggc acaaacggca ccaagcggtt cgataacccc       240
gtgctgccct tcaacgacgg cgtgtacttc gcctccatcg aaaaaagcaa cattatcaga       300
ggctggatct tcggcaccac cctggattcc aagacccagt ccctgctgat cgtgaacaac       360
gccaccaacg tcgtgatcaa ggtgtgtgag ttccagttct gtaatgaccc cttcctggac       420
cacaagaaca caagagctg atggagagc gagttcaggg tgtacagctc cgccaacaac       480
tgcacattcg agtacgtgag ccagcccttc ctgatggacc tggagggcaa gcagggcaac       540
```

```
ttcaagaatc tgagagagtt cgtgttcaag aacatcgatg gatacttcaa gatctacagc    600
aagcacaccc ctatcatcgt gagggagcct gaggacctgc cccagggctt cagcgccctg    660
gagcccctcg tggacctgcc tatcggcatc aacatcacaa ggttccagac cctgctggcc    720
ctgcacaggt cctacctgac accaggcgac agcagcagcg gctggacagc cggcgccgcc    780
gcctactatg tgggctacct gcagcccaga acattcctgc tgaagtataa cgagaatggc    840
accatcacag acgccgtgga ctgtgccctg atcccctga gcgagaccaa gtgcactctg    900 aagtcctta cagtggagaa gggaatctac cagacaagca atttcagggt gcagcctaca    960
gagagcattg tgagattccc taacatcacc aacctgtgcc cctttgacga agtgtttaac    1020
gctacacggt ttgcatcagt gtatgcctgg aacaggaaga gaatcagtaa ctgtgtggcc    1080
gactactctg tgctgtataa cctggctccc ttctttactt tcaaatgcta cggggtgagc    1140
cctactaagc tgaatgacct gtgtttcaca aacgtgtatg ccgatagctt tgtgatcagg    1200
ggcgacgaag tgacagat cgctccaggc cagacaggat atattgccga ttacaactat    1260
aaactgcccg atgacttcac aggatgcgtg attgcctgga atagcaataa gctggattct    1320
aaagtgagcg gcaattacaa ttacctgtat aggctgttca gaaagagcaa cctgaagcct    1380
ttcgagagag acatctccac tgaaatctat caggccggca ataagccctg caacggcgtg    1440
gctggcttta ttgttacttt cccctgaga tcctatagct ttcgcccac ctatggcgtg    1500 ggacaccagc cttacagagt ggtggtgctg tccttcgagc tgctgcacgc ccctgccaca    1560
gtgtgcggcc caaagaagtc caccaatctg gtgaagaata gtgcgtgaa cttctgataa    1620
```

```
<210> SEQ ID NO 23
<211> LENGTH: 1614
<212> TYPE: DNA
<213> ORGANISM: Artificial Sequence
<220> FEATURE:
<223> OTHER INFORMATION: For the preparation of mRNA vaccines

<400> SEQUENCE: 23
```

```
atgttcgtgt tcctggtgct gctgcctctg gtgagcagcc agtgcgtgaa cctgaccacc     60
aggacccagc tgcctcctgc ctacaccaac agcttcacca ggggcgtgta ctaccctgac    120
aaggtgttca ggagcagcgt gctgcacagc acccaggacc tgttcctgcc tttcttcagc    180
aacgtgacct ggttccacgt gatcagcggc accaacggca caagaggtt cgacaaccct    240 gtgctgcctt tcaacgacgg cgtgtacttc gccagcatcg agaagagcaa catcatcagg    300
ggctggatct tcggcaccac cctggacagc aagacccaga gcctgctgat cgtgaacaac    360
gccaccaacg tggtgatcaa ggtgtgcgag ttccagttct gcaacgaccc tttcctggac    420
cacaagaaca caagagctg gatggagagc gagttcaggg tgtacagcag cgccaacaac    480
tgcaccttcg agtacgtgag ccagccttc ctgatggacc tggagggcaa gcagggcaac    540
ttcaagaacc tgagggagtt cgtgttcaag aacatcgacg ctacttcaa gatctacagc    600 aagcacaccc ctatcctggt gagggagcct gaggacctgc ctcagggctt cagcgccctg    660
gagcctctgg tggacctgcc tatcggcatc aacatcacca ggttccagac cctgctggcc    720
ctgcacagga gctacctgac ccctggcgac agcagcagcg gctggaccgc cggcgccgcc    780
gcctactacg tgggctacct gcagcctagg accttcctgc tgaagtacaa cgagaacggc    840
accatcaccg acgccgtgga ctgcgccctg gaccctctga gcgagaccaa gtgcaccctg    900
aagagcttca ccgtggagaa gggcatctac cagaccagca acttcagggt gcagcctacc    960
```

```
gagagcatcg tgaggttccc taacatcacc aacctgtgcc ctttcgacga ggtgttcaac    1020
gccaccaggt tcgccagcgt gtacgcctgg aacaggaaga ggatcagcaa ctgcgtggcc    1080
gactacagcg tgctgtacaa cctggcccct tcttcacct tcaagtgcta cggcgtgagc    1140
cctaccaagc tgaacgacct gtgcttcacc aacgtgtacg ccgacagctt cgtgatcagg    1200
ggcgacgagg tgaggcagat cgcccctggc cagaccggca acatcgccga ctacaactac    1260
aagctgcctg acgacttcac cggctgcgtg atcgcctgga acagcaacaa gctggacagc    1320
aaggtgagcg gcaactacaa ctacctgtac aggctgttca ggaagagcaa cctgaagcct    1380
ttcgagaggg acatcagcac cgagatctac caggccggca acaagccttg caacggcgtg    1440
gccggcttca actgctactt ccctctgagg agctacagct caggcctac ctacggcgtg    1500 ggccaccagc ttacaggggt ggtggtgctg agcttcgagc tgctgcacgc ccctgccacc    1560
gtgtgcggcc ctaagaagag caccaacctg gtgaagaaca gtgcgtgaa cttc          1614
```

<210> SEQ ID NO 24
<211> LENGTH: 1614
<212> TYPE: DNA
<213> ORGANISM: Artificial Sequence
<220> FEATURE:
<223> OTHER INFORMATION: For the preparation of mRNA vaccines

<400> SEQUENCE: 24

```
atgttcgtgt tcctggtgct gctgcccctg gtgagcagcc agtgcgtgaa cctgaccacc      60
aggacccagc tgccccccgc ctacaccaac agcttcacca ggggcgtgta ctaccccgac     120
aaggtgttca ggagcagcgt gctgcacagc acccaggacc tgttcctgcc cttcttcagc     180
aacgtgacct ggttccacgt gatcagcggc accaacggca ccaagaggtt cgacaacccc     240
gtgctgccct tcaacgacgg cgtgtacttc gccagcatcg agaagagcaa catcatcagg     300
ggctggatct tcggcaccac cctggacagc aagacccaga gcctgctgat cgtgaacaac     360
gccaccaacg tggtgatcaa ggtgtgcgag ttccagttct gcaacgaccc cttcctggac     420
cacaagaaca caagagctg gatggagagc gagttcaggg tgtacagcag cgccaacaac     480 tgcacctcg agtacgtgag ccagcccttc ctgatggacc tggagggcaa gcagggcaac     540
ttcaagaacc tgagggagtt cgtgttcaag aacatcgacg gctacttcaa gatctacagc     600
aagcacaccc ccatcctggt gagggagccc gaggacctgc cccagggctt cagcgccctg     660
gagcccctgg tggacctgcc catcggcatc aacatcacca ggttccagac cctgctggcc     720
ctgcacagga gctacctgac ccccggcgac agcagcagcg gctggaccgc cggcgccgcc     780
gcctactacg tgggctacct gcagcccagg accttcctgc tgaagtacaa cgagaacggc     840
accatcaccg acgccgtgga ctgcgccctg gaccccctga gcgagaccaa gtgcaccctg     900
aagagcttca ccgtggagaa gggcatctac cagaccagca acttcagggt gcagcccacc     960
gagagcatcg tgaggttccc caacatcacc aacctgtgcc ccttcgacga ggtgttcaac    1020
gccaccaggt tcgccagcgt gtacgcctgg aacaggaaga ggatcagcaa ctgcgtggcc    1080
gactacagcg tgctgtacaa cctggccccc ttcttcacct tcaagtgcta cggcgtgagc    1140
cccaccaagc tgaacgacct gtgcttcacc aacgtgtacg ccgacagctt cgtgatcagg    1200
ggcgacgagg tgaggcagat cgcccccggc cagaccggca acatcgccga ctacaactac    1260
aagctgcccg acgacttcac cggctgcgtg atcgcctgga acagcaacaa gctggacagc    1320
aaggtgagcg gcaactacaa ctacctgtac aggctgttca ggaagagcaa cctgaagcct    1380
ttcgagaggg acatcagcac cgagatctac caggccggca acaagcccctg caacggcgtg    1440
```

```
gccggcttca actgctactt ccccctgagg agctacagct tcaggcccac ctacggcgtg      1500
ggccaccagc cctacagggt ggtggtgctg agcttcgagc tgctgcacgc ccccgccacc      1560
gtgtgcggcc caagaagag caccaacctg gtgaagaaca agtgcgtgaa cttc            1614

<210> SEQ ID NO 25
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 25
auguucgugu uccuggugcu gcugcccug ugagcagcc agugcgugaa ccugaccacc         60
aggacccagc ugcccccgc cuacaccaac agcuucacca ggggcgugua cuaccccgac       120
aagguguuca ggagcagcgu gcugcacagc acccaggacc uguccugcc cuucuucagc       180 aacgugaccu gguccacgc cauccacgug agcggcacca acggcaccaa gagguucgac       240
aaccccgugc ugcccuucaa cgacggcgug uacuucgcca gcaccgagaa gagcaacauc      300
aucaggggcu ggaucuucgg caccacccug gacagcaaga cccagagccu gcugaucgug      360
aacaacgcca ccaacguggu gaucaaggug ugcgaguucc aguucugcaa cgacccuuuc      420
cugggcguga cuaccacaa gaacaacaag agcuggaugg agagcgaguu caggguguac      480
agcagcgcca acaacugcac cuucgaguac gugagccagc cuuccugau ggaccuggag      540 ggcaagcagg gcaacuucaa gaaccugagg gaguucgugu ucaagaacau cgacggcuac      600
uucaagaucu acagcaagca cacccccauc aaccuggga gggaccugcc cagggcuuc       660 agcgcccugg agcccuuggu ggaccugccc aucggcauca acauccag guucagacc       720 cugcuggccc ugcacaggag cuaccugacc cccggcgaca gcagcagcgg cuggaccgcc      780
ggcgccgccg ccuacuacgu gggcuaccug cagcccagga ccuuccugcu gaaguacaac      840
gagaacggca ccaucaccga cgccguggac ugcgcccugg accccugag cgagaccaag      900 ugcacccuga gagcuucac cguggagaag ggcaucuacc agaccagcaa cuucagggug      960
cagcccaccg agagcaucgu gagguucccc aacaucacca accugugccc cuucggcgag      1020
guguucaacg ccaccagguu cgccagcgug uacgccugga caggaagag gaucagcaac      1080 ugcguggcca cuacagcgu gcuguacaac agcgccagcu ucagcaccuu caagugcuac      1140
ggcgugagcc ccaccaagcu gaacgaccug ugcuucacca cguguacgc cgacagcuuc      1200 gugaucaggg gcgacgaggu gaggcagauc gcccccggcc agaccggcaa gaucgccgac      1260
uacaacuaca agcugcccga cgacuucacc ggcugcguga ucgccuggaa cagcaacaac      1320
cuggacagca aggugggcgg caacuacaac uaccuguaca ggcuguucag gaagagcaac      1380
cugaagcccu ucgagaggga caucagcacc gagaucuacc aggccggcag caccccugc      1440 aacggcgugg agggcuucaa cugcuacuuc cccucugcaga gcuacggcuu ccagcccacc      1500
aacggcgugg gcuaccagcc cuacagggug guggugcuga gcuucgagcu gcugcacgcc      1560
cccgccaccg ugugcggccc caagaagagc accaaccugg ugaagaacaa gugcgugaac      1620
uuc                                                                    1623

<210> SEQ ID NO 26
<211> LENGTH: 1623
<212> TYPE: RNA
<213> ORGANISM: Artificial Sequence
<220> FEATURE:
```

<223> OTHER INFORMATION: mRNAvaccines

<400> SEQUENCE: 26

| | |
|---|---|
| auguucgugu uccuggugcu gcugccucug gugagcagcc agugcgugaa ccugaccacc | 60 |
| agaacccagc ugccuccugc cuacaccaac agcuucacca gaggcgugua cuacccugac | 120 |
| aagguguuca gaagcagcgu gcugcacagc acccaggacc uguuccugcc uuucuucagc | 180 |
| aacgugaccu gguccacgc cauccacgug agcggcacca acggcaccaa agagauucgac | 240 |
| aacccugugc ugccuuucaa cgacggcgug uacuucgcca gcaccgagaa gagcaacauc | 300 |
| aucagaggcu ggaucuucgg caccacccug acagcaaga cccagagccu gcugaucgug | 360 |
| aacaacgcca ccaacguggu gaucaaggug ugcgaguucc aguucugcaa cgacccuuuc | 420 |
| cugggcgugu acuaccacaa gaacaacaag agcuggaugg agagcgaguu cagaguguac | 480 |
| agcagcgcca acaacugcac cuucgaguac gugagccagc uuuccugau ggaccuggag | 540 |
| ggcaagcagg gcaacuucaa gaaccugaga gaguucugu ucaagaacau cgacggcuac | 600 |
| uucaagaucu acagcaagca caccccuauc aaccgguga gagaccugcc ucagggcuuc | 660 |
| agcgcccugg agccucuggu ggaccugccu aucggcauca acaucaccag auuccagacc | 720 |
| cugcuggccc ugcacagaag cuaccugacc ccuggcgaca gcagcggc cuggaccgcc | 780 |
| ggcgccgccg ccuacuacgu gggcuaccug cagccuagaa ccuuccugcu gaaguacaac | 840 |
| gagaacggcc caucaccga cgccguggac ugcgcccugg acccucugag cgagaccaag | 900 |
| ugcaccuga agagcuucac cguggagaag ggcaucuacc agaccagcaa cuucagagug | 960 |
| cagccuaccg agagcaucgu gagauucccu aacaucacca accugugccc uuucggcgag | 1020 |
| guguucaacg ccaccagauu cgccagcgug uacgccugga cagaaagag aaucagcaac | 1080 |
| ugcguggcca cuacagcgu gcuguacaac agcgccagcu ucagcaccuu caagugcuac | 1140 |
| ggcgugagcc cuaccaagcu gaacgaccug ugcuucacca cguguacgc cgacagcuuc | 1200 |
| gugaucagag cgacgaggu gagacagauc gccccuggcc agaccggcaa gaucgccgac | 1260 |
| uacaacuaca agcugccuga cgacuucacc ggcugcguga ucgccuggaa cagcaacaac | 1320 |
| cuggacagca ggugggcgg caacuacaac uaccuguaca gacuguucag aaagagcaac | 1380 |
| cugaagccuu ucgagagaga caucagcacc gagaucuacc aggccggcag cacccccuugc | 1440 |
| aacggcgugg agggcuucaa cugcuacuuc ccucugcaga gcuacggcuu ccagccuacc | 1500 |
| aacggcgugg gcuaccagcc uuacagagug gugugcuga gcuucagcu gcugcacgcc | 1560 |
| ccugccaccg ugugcggccc uaagaagagc accaaccugg ugaagaacaa gugcgugaac | 1620 |
| uuc | 1623 |

<210> SEQ ID NO 27
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 27

| | |
|---|---|
| auguucgugu uccuggugcu gcugccccug gugagcagcc agugcgugaa ccugaccacc | 60 |
| aggacccagc ugcccccgc cuacaccaac agcuucacca ggggcgugua cuaccccgac | 120 |
| aagguguuca ggagcagcgu gcugcacagc acccaggacc uguuccugcc cuucuucagc | 180 |
| aacgugaccu gguccacgc cauccacgug agcggcacca acggcaccaa gagguucgac | 240 |
| aaccccgugc ugcccuucaa cgacggcgug uacuucgcca gcaccgagaa gagcaacauc | 300 |

```
aucaggggcu ggaucuucgg caccacccug gacagcaaga cccagagccu gcugaucgug      360
aacaacgcca ccaacguggu gaucaaggug ugcgaguucc aguucugcaa cgacccccuuc     420 cugggcgugu acuaccacaa gaacaacaag agcuggaugg agagcgaguu caggguguac     480
agcagcgcca caacugcac cuucgaguac gugagccagc ccuuccugau ggaccuggag      540
ggcaagcagg gcaacuucaa gaaccugagg gaguucgugu ucaagaacau cgacggcuac     600
uucaagaucu acagcaagca caccccccauc aaccuggugu gggaccugcc ccagggcuuc    660
agcgcccugg agcccuggu ggaccugccc aucggcauca acaucaccag guuccagacc     720
cugcuggccc ugcacaggag cuaccugacc cccggcgaca gcagcagcgg cuggaccgcc    780
ggcgccgccg ccuacuacgu gggcuaccug cagcccagga ccuuccugcu gaaguacaac    840
gagaacggca ccaucaccga cgccguggac ugcgcccugg accccugag cgagaccaag    900 ugcacccuga gagcuucac cguggagaag ggcaucuacc agaccagcaa cuucaggug      960 cagcccaccg agagcaucgu gagguuccccc aacaucacca accugugccc cuucggcgag  1020
guguucaacg ccaccaggu ucgccagcgu gacgccugga caggaagag gaucagcaac    1080 ugcguggccg acuacagcgu gcuguacaac agcgccagcu ucagcaccuu caagugcuac   1140
ggcgugagcc ccaccaagcu gaacgaccug ugcuucacca cguguacgc cgacagcuuc    1200 ugaucaggg gcgacgaggu gaggcagauc gccccccggcc agaccggcaa gaucgccgac  1260
uacaacuaca agcugcccga cgacuucacc ggcugcguga ucgccuggaa cagcaacaac  1320
cuggacagca agguggcgg caacuacaac uaccuguaca ggcuguucag gaagagcaac    1380
cugaagcccu ucgagaggga caucagcacc gagaucuacc aggccggcag cacccccugc   1440
aacggcgugg agggcuucaa cugcuacuuc ccccugcaga gcuacggcuu ccagcccacc    1500 aacgcgugg gcuaccagcc cuacagggug guggugcuga gcuucgagcu gcugcacgcc    1560
cccgccaccg ugugcggccc caagaagagc accaaccugg ugaagaacaa gugcgugaac  1620
uuc                                                                 1623
```

<210> SEQ ID NO 28
<211> LENGTH: 1614
<212> TYPE: RNA
<213> ORGANISM: Artificial Sequence
<220> FEATURE:
<223> OTHER INFORMATION: mRNAvaccines
<400> SEQUENCE: 28

```
auguucgugu uccuggugcu gcugcccug gugagcagcc agugcgugaa ccugaccacc       60
agaacccagc ugccccccgc cuacaccaac agcuucacca gaggcgugua cuaccccgac    120 aagguuca gaagcagcgu gcugcacagc acccaggacc uguccugcc cuucuucagc      180 aacgugaccu gguuccacgc caucagcggc accaacggca ccaagagauu cgacaacccc    240
gugcugcccu ucaacgacgg cguguacuuc gccagcaccg agaagagcaa caucaucaga    300 ggcugggaucu ucggcaccac ccuggacagc aagacccaga gccugcugau cgugaacaac  360
gccaccaacg uggugaucaa ggugugcgag uuccaguucu gcaacgaccc cuuccugggc    420
guguaccaca gaacaacaa gagcuggaug gagagcgagu ucagagugua cagcagcgcc    480
aacaacugca ccuucgagua cgugagccag cccuuccuga uggaccugga gggcaagcag    540
ggcaacuuca agaaccugag agaguucgug uucaagaaca ucgacggcua cuucaagauc    600
uacagcaagc acaccccccau caaccuggug agagaccugc ccagggcuu cagcgcccug   660
```

-continued

```
gagcccugg uggaccugcc caucggcauc aacaucacca gauuccagac ccugcuggcc    720
cugcacagaa gcuaccugac ccccggcgac agcagcagcg gcuggaccgc cggcgccgcc    780
gccuacuacg ugggcuaccu gcagcccaga accuuccugc ugaaguacaa cgagaacggc    840
accaucaccg acgccgugga cugcgcccug gaccccguga gcgagaccaa gugcacccug    900
aagagcuuca ccguggagaa gggcaucuac cagaccagca acuucagagu gcagcccacc    960
gagagcaucg ugagauuccc caacaucacc aaccugugcc ccuucggcga ggucuucaac   1020
gccaccagau cgccagcgu uacgccugg aacagaaaga gaaucagcaa cugcguggcc   1080
gacuacagcg ugcuguacaa cagcgccagc uucagcaccu ucaagugcua cggcgugagc   1140
cccaccaagc ugaacgaccu ugcuucacc aacguguacg ccgacagcuu cgugaucaga   1200
ggcgacgagg ugagacagau cgccccggc cagaccggca agaucgccga cuacaacuac   1260
aagcugcccg acgacuuucac cggcugcgug aucgccugga cagcaacaa ccuggacagc   1320
aaggugggcg gcaacuacaa cuaccuguac agacuguuca aaagagcaa ccugaagccc   1380
uucgagagag acaucagcac cgagaucuac caggccggca gcacccccug caacggcgug   1440
gagggcuuca acugcuacuu ccccccugcag agcuacggcu ccagcccac cuacggcgug   1500
ggcuaccagc ccuacagagu gguggugcug agcuucgagc ugcugcacgc ccccgccacc   1560
gugugcggcc ccaagaagag caccaaccug gugaagaaca gugcgugaa cuuc         1614
```

<210> SEQ ID NO 29
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 29

```
auguucgugu uccggugcu gcugccucug gugagcagcc agugcgugaa ccugaccacc     60
agaacccagc ugcccuccug cuacaccaac agcuucacca gagcgugua cuacccugac    120
aaggguuuca gaagcagcgu gcugcacagc acccaggacc uguuccugcc uuucuucagc    180
aacgugaccu gguccacgc caucagcggc accaacggca ccaagagauu cgacaacccu    240
gugcugccuu ucaacgacgg cguguacuuc gccagcaccg agaagagcaa caucaucaga    300
ggcuggaucu ucggcaccac ccuggacagc aagacccaga gccugcugau cgugaacaac    360
gccaccaacg uggugaucaa ggugugcgag uuccaguucu gcaacgaccc uuuccugggc    420
guguaccaca agaacaacaa gagcuggaug gagagcgagu ucagagugua cagcagcgcc    480
aacaacugca ccuucgagua cgugagccag ccuuuccuga uggaccugga gggcaagcag    540
ggcaacuuca gaaccugag agaguucgug uucaagaaca ucgacggcua cuucaagauc    600
uacagcaagc acacccccuau caaccuggug agagaccugc cucagggcuu cagcgcccug    660
gagcccucugg uggaccugcc uaucggcauc aacaucacca gauuccagac ccugcuggcc    720
cugcacagaa gcuaccugac ccccggcgac agcagcagcg gcuggaccgc cggcgccgcc    780
gccuacuacg ugggcuaccu gcagccuaga accuuccugc ugaaguacaa cgagaacggc    840
accaucaccg acgccgugga cugcgcccug gaccccucga gcgagaccaa gugcacccug    900
aagagcuuca ccguggagaa gggcaucuac cagaccagca acuucagagu gcagccuacc    960
gagagcaucg ugagauuccc uaacaucacc aaccugugcc cuucggcga ggucuucaac   1020
gccaccagau cgccagcgu uacgccugg aacagaaaga gaaucagcaa cugcguggcc   1080
gacuacagcg ugcuguacaa cagcgccagc uucagcaccu ucaagugcua cggcgugagc   1140
```

| | |
|---|---|
| ccuaccaagc ugaacgaccu gugcuucacc aacguguacg ccgacagcuu cgugaucaga | 1200 |
| ggcgacgagg ugagacagau cgccccuggc cagaccggca agaucgccga cuacaacuac | 1260 |
| aagcugccug acgacuucac cggcugcgug aucgccugga acagcaacaa ccuggacagc | 1320 |
| aagguggggcg gcaacuacaa cuaccuguac agacuguuca gaaagagcaa ccugaagccu | 1380 |
| uucgagagag acaucagcac cgagaucuac caggccggca gcacccccuug caacggcgug | 1440 |
| gagggcuuca acugcuacuu cccucugcag agcuacggcu ccagccuac cuacggcgug | 1500 |
| ggcuaccagc cuuacagagu ggugguggcug agcuucgagc ugcugcacgc cccugccacc | 1560 |
| gugugcggcc cuaagaagag caccaaccug gugaagaaca gugcgugaa cuuc | 1614 |

<210> SEQ ID NO 30
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 30

| | |
|---|---|
| auguucgugu uccuggugcu gcugcccccug gugagcagcc agugcgugaa ccugaccacc | 60 |
| aggacccagc ugccccccgc cuacaccaac agcuucacca ggggcguguau cuaccccgac | 120 |
| aagguguuca ggagcagcgu gcugcacagc acccaggacc uguuccugcc cuucuucagc | 180 |
| aacgugaccu gguuccacgc caucagcggc accaacggca ccaagagguu cgacaaccc | 240 |
| gugcugcccu ucaacgacgg cguguacuuc gccagcaccg agaagagcaa caucaucagg | 300 |
| ggcuggaucu ucggcaccac ccuggacagc aagcccaga gccugcugau cgugaacaac | 360 |
| gccaccaacg uggugaucaa ggugugcgag uuccaguucu gcaacgaccc cuuccugggc | 420 |
| guguaccaca gaacaacaa gagcuggaug gagagcgagu cagggugua cagcagcgcc | 480 |
| aacaacugca ccuucgagua cgugagccag cccuuccuga uggaccugga gggcaagcag | 540 |
| ggcaacuuca gaaccugag ggaguucgug uucaagaaca ucgacggcua cuucaagauc | 600 |
| uacagcaagc acaccccau caaccuggug agggaccugc ccagggcuu cagcgcccug | 660 |
| gagcccccugg uggaccugcc caucggcauc aacaucacca gguucagac ccugcuggcc | 720 |
| cugcacagga gcuaccugac ccccggcgac agcagcagcg gcuggaccgc ggcgccgcc | 780 |
| gccuacuacg uggggcuaccu gcagcccagg accuccugc ugaaguacaa cgagaacggc | 840 |
| accaucaccg acgccgugga cugcgcccug gacccccuga gcgagaccaa gugcacccug | 900 |
| aagagcuuca ccguggagaa gggcaucuac cagaccagca cuucagggu gcagccccacc | 960 |
| gagagcaucg ugagguuccc caacaucacc aaccugugcc ccuucggcga ggugcgguucaac | 1020 |
| gccaccaggu cgccagcgu guacgccugg aacaggaaga ggaucagcaa cugcguggcc | 1080 |
| gacuacagcg ugcuguacaa cagcgccagc uucagcaccu ucaagugcua cggcgugagc | 1140 |
| cccaccaagc ugaacgaccu gugcuucacc aacguguacg ccgacagcuu cgugaucagg | 1200 |
| ggcgacgagg ugaggcagau cgccccuggc cagaccggca agaucgccga cuacaacuac | 1260 |
| aagcugcccg acgacuucac cggcugcgug aucgccugga acagcaacaa ccuggacagc | 1320 |
| aagguggggcg gcaacuacaa cuaccuguac aggcuguuca ggaagagcaa ccugaagccc | 1380 |
| uucgagaggg acaucagcac cgagaucuac caggccggca gcacccccuug caacggcgug | 1440 |
| gagggcuuca acugcuacuu cccccugcag agcuacggcu ccagcccac cuacggcgug | 1500 |
| ggcuaccagc cuuacagggu ggugguggcug agcuucgagc ugcugcacgc cccgccacc | 1560 | gugugcggcc ccaagaagag caccaaccug gugaagaaca agugcgugaa cuuc    1614

<210> SEQ ID NO 31
<211> LENGTH: 1617
<212> TYPE: RNA
<213> ORGANISM: Artificial Sequence
<220> FEATURE:
<223> OTHER INFORMATION: mRNAvaccines

<400> SEQUENCE: 31
auguucgugu uccuggugcu gcugccccug gugagcagcc agugcgugaa ccugaccacc    60
aggacccagc ugcccccgc cuacaccaac agcuucacca ggggcgugua cuacccgac    120
aagguguuca ggagcagcgu gcugcacagc acccaggacc uguccugcc cuucuucagc    180
aacgugaccu gguccacgc cauccacgug agcggcacca acggcaccaa gagguucgcc    240
aaccccgugc ugcccuucaa cgacggcgug uacuucgcca gcaccgagaa gagcaacauc    300
aucaggggcu ggaucuucgg caccacccug acagcaaga cccagagccu gcugaucgug    360
aacaacgcca ccaacguggu gaucaaggug ugcgaguucc aguucugcaa cgaccccuuc    420
cugggcgugu acuaccacaa gaacaacaag agcuggaugg agagcgaguu caggguguac    480
agcagcgcca caacugcac cuucgaguac gugagccagc ccuuccugau ggaccuggag    540
ggcaagcagg gcaacuucaa gaaccugagg gaguucgugu ucaagaacau cgacggcuac    600
uucaagaucu acagcaagca caccccauc aaccgguga ggggccugcc caggggcuuc    660
agcgcccugg agccccuggu ggaccugccc aucggcauca acauccag guccagacc    720
cugcugcaca ggagcuaccu gaccccggc gacagcagca cggcuggac cgccggcgcc    780
gccgccuacu acguggcua ccugcagccc aggaccuucc ugcugaagua caacgagaac    840
ggcaccauca ccgacgccgu ggacugcgcc cuggaccccc ugagcgagac caagugcacc    900
cugaagagcu ucaccgugga aagggcauc uaccagacca gcaacuucag ggugcagccc    960
accgagagca ucgugagguu ccccaacauc accaaccgu gccccuucgg cgagguguuc    1020
aacgccacca gguucgccag cgucuacgcc uggaacagga gaggaucag caacugcgug    1080
gccgacuaca gcgugcugua caacagcgcc agcuucagca ccucaagug cuacggcgug    1140
agccccacca gcugaacga ccgugcuuc accaacgugu acgccgacag cuucgugauc    1200
aggggcgacg aggugagca gaucgccccc ggccagaccg gcaacaucgc cgacuacaac    1260
uacaagcugc ccgacgacuu caccggcugc gugaucgccu ggaacagcaa caaccuggac    1320
agcaaggugg gcggcaacua caacuaccug uacaggcugu caggaagag caaccugaag    1380
cccuucgaga gggacaucag caccgagauc uaccaggccg gcagcacccc cugcaacggc    1440
gugaagggcu ucaacugcua cuuccccug cagagcuacg gcuucagcc caccuacggc    1500
gugggcuacc agcccuacag ggugguggug cugagcuucg agcugcugca cgcccccgcc    1560
accgugugcg gccccaagaa gagccaccaac cuggugaaga caagugcgu gaacuuc    1617

<210> SEQ ID NO 32
<211> LENGTH: 1617
<212> TYPE: RNA
<213> ORGANISM: Artificial Sequence
<220> FEATURE:
<223> OTHER INFORMATION: mRNAvaccines

<400> SEQUENCE: 32
auguucgugu uccuggugcu gcugcccucug gugagcagcc agugcgugaa ccugaccacc    60
aggacccagc ugccuccugc cuacaccaac agcuucacca ggggcgugua cuacccugac    120

| | |
|---|---|
| aagguguuca ggagcagcgu gcugcacagc acccaggacc uguuccugcc uuucuucagc | 180 |
| aacgugaccu gguuccacgc cauccacgug agcggcacca acggcaccaa gagguucgcc | 240 |
| aacccugugc ugccuuucaa cgacggcgug uacuucgcca gcaccgagaa gagcaacauc | 300 |
| aucaggggcu ggaucuucgg caccacccug gacagcaaga cccagagccu gcugaucgug | 360 |
| aacaacgcca ccaacguggu gaucaaggug ugcgaguucc aguucugcaa cgacccuuuc | 420 |
| cugggcgugu acuaccacaa gaacaacaag agcuggaugg agagcgaguu caggguguac | 480 |
| agcagcgcca acaacugcac cuucgaguac gugagccagc cuuccugau ggaccuggag | 540 |
| ggcaagcagg gcaacuucaa gaaccugagg aguucgugu caagaacau cgacggcuac | 600 |
| uucaagaucu acagcaagca cacccccuauc aaccggguga ggggccugcc ucagggcuuc | 660 |
| agcgcccugg agccucuggu ggaccugccu aucggcauca acaucaccag guuccagacc | 720 |
| cugcugcaca ggagcuaccu gaccccuggc gacagcagca gcggcuggac cgccggcgcc | 780 |
| gccgccuacu acgugggcua ccugcagccu aggaccuucc ugcugaagua caacgagaac | 840 |
| ggcaccauca ccgacgccgu ggacugcgcc cuggacccuc ugagcgagac caagugcacc | 900 |
| cugaagagcu ucaccgugga aagggcauc uaccagacca gcaacuucag ggugcagccu | 960 |
| accgagagca ucgugagguu cccuaacauc accaaccugu gcccuuucgg cgaggguuc | 1020 |
| aacgccacca gguucgccag cguguacgcc uggaacagga gaggaucag caacugcgug | 1080 |
| gccgacuaca gcgugcugua caacagcgcc agcuucagca ccuucaagug cuacggcgug | 1140 |
| agcccuacca gcugaacga ccugugcuuc accaacgugu acgccgacag cuucgugauc | 1200 |
| aggggcgacg aggugaggca gaucgccccu ggccagaccg gcaacaucgc cgacuacaac | 1260 |
| uacaagcugc cugacgacuu caccggcugc gugaucgccu ggaacagcaa caaccuggac | 1320 |
| agcaaggugg gcggcaacua caacuaccug uacaggcugu caggaagag caaccugaag | 1380 |
| ccuuucgaga gggacaucag caccgagauc uaccaggccg gcagcacccc uugcaacggc | 1440 |
| gugaagggcu ucaacugcua cuucccucug cagagcuacg gcuuccagcc uaccuacggc | 1500 |
| gugggcuacc agccuuacag ggugguggug cugagcuucg agcugcugca cgccccugcc | 1560 |
| accgugugcg gcccuaagaa gagcaccaac cuggugaaga caagugcgu gaacuuc | 1617 |

<210> SEQ ID NO 33
<211> LENGTH: 1617
<212> TYPE: RNA
<213> ORGANISM: Artificial Sequence
<220> FEATURE:
<223> OTHER INFORMATION: mRNAvaccines

<400> SEQUENCE: 33

| | |
|---|---|
| auguucgugu uccuggugcu gcugcccucug gugagcagcc agugcgugaa ccugaccacc | 60 |
| aggacccagc ugccccccgc cuacaccaac agcuucacca ggggcgugua cuaccccgac | 120 |
| aagguguuca ggagcagcgu gcugcacagc acccaggacc uguuccugcc cuucuucagc | 180 |
| aacgugaccu gguuccacgc cauccacgug agcggcacca acggcaccaa gagguucgcc | 240 |
| aaccccgugc ugcccuucaa cgacggcgug uacuucgcca gcaccgagaa gagcaacauc | 300 |
| aucaggggcu ggaucuucgg caccacccug gacagcaaga cccagagccu gcugaucgug | 360 |
| aacaacgcca ccaacguggu gaucaaggug ugcgaguucc aguucugcaa cgacccuuuc | 420 |
| cugggcgugu acuaccacaa gaacaacaag agcuggaugg agagcgaguu caggguguac | 480 |
| agcagcgcca acaacugcac cuucgaguac gugagccagc cuuccugau ggaccuggag | 540 |

-continued

| | |
|---|---|
| ggcaagcagg gcaacuucaa gaaccugagg gaguucgugu ucaagaacau cgacggcuac | 600 |
| uucaagaucu acagcaagca cacccccauc aaccugguga ggggccugcc ccagggcuuc | 660 |
| agcgcccugg agcccuggu ggaccugccc aucggcauca acaucaccag guuccagacc | 720 |
| cugcugcaca ggagcuaccu gacccccggc gacagcagca cggcuggac cgccggcgcc | 780 |
| gccgccuacu acgugggcua ccugcagccc aggaccuucc ugcugaagua caacgagaac | 840 |
| ggcaccauca ccgacgccgu ggacugcgcc cuggaccccc ugagcgagac caagugcacc | 900 |
| cugaagagcu caccgugga aagggcauc uaccagacca gcaacuucag ggugcagccc | 960 |
| accgagagca ucgugaggu ccccaacauc accaaccugu gccccuucgg cgagguguuc | 1020 |
| aacgccacca gguucgccag cguguacgcc uggaacagga gaggaucag caacugcgug | 1080 |
| gccgacuaca gcgugcugua acagcgccc agcuucagca ccuucaagug cuacggcgug | 1140 |
| agccccacca agcugaacga ccugugcuuc accaacgugu acgccgacag cuucgugauc | 1200 |
| aggggcgacg aggugaggca gaucgccccc ggccagaccg gcaacaucgc cgacuacaac | 1260 |
| uacaagcugc ccgacgacuu caccggcugc gugaucgccu ggaacagcaa caaccuggac | 1320 |
| agcaaggugg cggcaacua caacuaccug uacaggcugu ucaggaagag caaccugaag | 1380 |
| cccuucgaga gggacaucag caccgagauc uaccaggccg gcagccccc cugcaacggc | 1440 |
| gugaagggcu ucaacugcua cuucccccug cagagcuacg gcuuccagcc caccuacggc | 1500 |
| gugggcuacc agcccuacag gguggugug cugagcuucg agcugcugca cgcccccgcc | 1560 |
| accgugugcg gccccaagaa gagcaccaac cuggugaaga acaagugcgu gaacuuc | 1617 |

<210> SEQ ID NO 34
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 34

| | |
|---|---|
| auguucgugu uccuggugcu gcugcccug ugagcagcc agugcgugaa cuucaccaac | 60 |
| agaacccagc ugcccagcgc cuacaccaac agcuucacca gaggcgugua cuaccccgac | 120 |
| aagguguuca agagcagcgu gcugcacagc acccaggacc uguuccugcc cuucuucagc | 180 |
| aacgugaccu gguucacgc cauccacgug agcggcacca cggcaccaa gagauucgac | 240 |
| aaccccgugc ugcccuucaa cgacggcgug uacuucgcca gcaccgagaa gagcaacauc | 300 |
| aucagaggcu ggaucuucgg caccacccug acagcaaga cccagagccu gcugaucgug | 360 |
| aacaacgcca ccaacguggu gaucaaggug ugcgaguucc aguucugcaa cuaccccuuc | 420 |
| cugggcgugu acuaccacaa gaacaacaag agcuggaugg agagcgaguu cagaguguac | 480 |
| agcagcgcca acaacugcac cuucgaguac gugagccagc cuuccugau ggaccuggag | 540 |
| ggcaagcagg gcaacuucaa gaaccugagc gaguucgugu ucaagaacau cgacggcuac | 600 |
| uucaagaucu acagcaagca cacccccauc aaccuggugga gagaccugcc ccagggcuuc | 660 |
| agcgcccugg agcccuggu ggaccugccc aucggcauca acaucaccag auuccagacc | 720 |
| cugcuggccc ugcacagaag cuaccugacc cccggcgaca gcagcggc cuggaccgcc | 780 |
| ggcgccgccg ccuacuacgu gggcuaccug agcccagaa ccuccugcu gaaguacaac | 840 |
| gagaacggca ccauccga cgccguggac ugcgcccugg accccugag cgagaccaag | 900 |
| ugcacccuga agagcuucac cguggagaag ggcaucuacc agaccagcaa cuucagagug | 960 |
| cagcccaccg agagcaucgu gagauucccc aacaucacca accugugccc cuucggcgag | 1020 |

| | |
|---|---|
| guguucaacg ccaccagauu cgccagcgug uacgccugga acagaaagag aaucagcaac | 1080 |
| ugcguggccg acuacagcgu gcuguacaac agcgccagcu ucagcaccuu caagugcuac | 1140 |
| ggcgugagcc ccaccaagcu gaacgaccug ugcuucacca acguguacgc cgacagcuuc | 1200 |
| gugaucagag cgacgaggu gagacagauc gcccccggcc agaccggcac caucgccgac | 1260 |
| uacaacuaca agcugcccga cgacuucacc ggcugcguga ucgccuggaa cagcaacaac | 1320 |
| cuggacagca aggugggcgg caacuacaac uaccuguaca cacuguucag aaagagcaac | 1380 |
| cugaagcccu ucgagagaga caucagcacc gagaucuacc aggccggcag cacccccugc | 1440 |
| aacggcguga agggcuucaa cugcuacuuc ccccugcaga gcuacggcuu ccagcccacc | 1500 |
| uacggcgugg gcuaccagcc cuacagagug gugugcuga gcuucgagcu gcugcacgcc | 1560 |
| cccgccaccg ugugcggccc caagaagagc accaaccugg ugaagaacaa gugcgugaac | 1620 |
| uuc | 1623 |

<210> SEQ ID NO 35
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 35

| | |
|---|---|
| auguucgugu uccuggugcu gcugccucug gugagcagcc agugcgugaa cuucaccaac | 60 |
| agaacccagc ugccuagcgc cuacaccaac agcuucacca gaggcgugua cuacccugac | 120 |
| aagguguuca agcagcgu gcugcacagc acccaggacc uguuccugcc uuucuucagc | 180 |
| aacgugaccu gguccacgc cauccacgug agcggcacca acggcaccaa gagauucgac | 240 |
| aacccugugc ugccuuucaa cgacggcgug uacuucgcca gcaccgagaa gagcaacauc | 300 |
| aucagaggcu ggaucuucgg cacccacccug gacagcaaga cccagagccu gcugaucgug | 360 |
| aacaacgcca ccaacguggu gaucaaggug ugcgaguucc aguucugcaa cuaccuuuc | 420 |
| cugggcgugu acuaccacaa gaacaacaag agcuggaugg agagcgaguu cagaguguac | 480 |
| agcagcgcca acaacugcac cuucgaguac gugagccagc uuucugau ggaccuggag | 540 |
| ggcaagcagg gcaacuucaa gaaccugagc gaguucgugu ucaagaacau cgacggcuac | 600 |
| uucaagaucu acagcaagca cacccccuauc aaccugguga gagaccugcc ucagggcuuc | 660 |
| agcgcccugg agccucuggu ggaccugccu aucggcauca acaucaccag auuccagacc | 720 |
| cugcuggccc ugcacagaag cuaccugacc ccuggcgaca gcagcggg cuggaccgcc | 780 |
| ggcgccgccg ccuacuacgu gggcuaccug cagccuagaa ccuuccugcu gaaguacaac | 840 |
| gagaacggca ccaucaccga cgccguggac ugcgcccugg acccucugag cgagaccaag | 900 |
| ugcacccuga agagcuucac cguggagaag ggcaucuacc agaccagcaa cuucagagug | 960 |
| cagccuaccg agagcaucgu gagauucccu aacaucacca accugugccc uuucggcgag | 1020 |
| guguucaacg ccaccagauu cgccagcgug uacgccugga acagaaagag aaucagcaac | 1080 |
| ugcguggccg acuacagcgu gcuguacaac agcgccagcu ucagcaccuu caagugcuac | 1140 |
| ggcgugagcc cuaccaagcu gaacgaccug ugcuucacca acguguacgc cgacagcuuc | 1200 |
| gugaucagag cgacgaggu gagacagauc gcccccggcc agaccggcac caucgccgac | 1260 |
| uacaacuaca agcugcccga cgacuucacc ggcugcguga ucgccuggaa cagcaacaac | 1320 |
| cuggacagca aggugggcgg caacuacaac uaccuguaca cacuguucag aaagagcaac | 1380 |

```
cugaagccuu ucgagagaga caucagcacc gagaucuacc aggccggcag caccccuugc      1440
aacggcguga agggcuucaa cugcuacuuc ccucugcaga gcuacggcuu ccagccuacc      1500
uacggcgugg cuaccagcc uuacagagug gugguucuga gcuucgagcu gcugcacgcc       1560
ccugccaccg ugugcggccc uaagaagagc accaaccugg ugaagaacaa gugcgugaac      1620
uuc                                                                    1623

<210> SEQ ID NO 36
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 36
auguucgugu uccuggugcu gcugccccug gugagcagcc agugcgugaa cuucaccaac        60
aggacccagc ugcccagcgc cuacaccaac agcuucacca ggggcgugua cuaccccgac       120
aaggcguuca ggagcagcgu gcugcacagc acccaggacc uguuccugcc cuucuucagc       180
aacgugaccu gguuccacgc cauccacgug agcggcacca acggcaccaa gagguucgac       240
aaccccgugc ugcccuucaa cgacggcgug uacuucgcca gcaccgagaa gagcaacauc       300
aucaggggcu ggaucuucgg caccacccug acagcaagaa cccagagccu gcugaucgug       360
aacaacgcca ccaacguggu gaucaaggug ugcgaguucc aguucugcaa cuaccccuuc       420
cugggcgugu acuaccacaa gaacaacaag agcuggaugg agagcgaguu caggguguac       480
agcagcgcca caacugcac cuucgaguac gugagccagc ccuuccugau ggaccuggag       540
ggcaagcagg gcaacuucaa gaaccugagc gaguucgugu caagaacau cgacggcuac       600 uucaagaucu acagcaagca cacccccauc aaccggguga gggaccugcc cagggcuuc        660 agcgcccugg agcccugggu ggaccugccc aucggcauca acauuccag guuccagacc       720 cugcuggccc ugcacaggag cuaccugacc cccggcgaca gcagcagcgg cuggaccgcc       780
ggcgccgccg ccuacuacgu gggcuaccug cagcccagga ccuuccugcu gaaguacaac       840
gagaacggca ccaucaccga cgccguggac ugcgcccugg accccugag cgagaccaag       900 ugcacccuga agagcuucac cguggagaag ggcaucuacc agaccagcaa cuucaggaug       960
cagcccaccg agagcaucgu gagguucccc aacaucacca accugugccc cuucggcgag      1020
guguucaacg ccaccagguu cgccagcgug uacgccugga caggaagag gaucagcaac      1080 ugcguggccg acuacagcgu gcuguacaac agcgccagcu ucagcaccuu caagugcuac      1140
ggcgugagcc ccaccaagcu gaacgaccug ugcuucacca cguguacgc cgacagcuuc      1200 gugaucaggg gcgacgaggu gaggcagauc gcccccggcc agaccggcac caucgccgac      1260
uacaacuaca agcugcccga cgacuucacc ggcugcguga ucgccuggaa cagcaacaac      1320
cuggacagca ggugggcgg caacuacaac uaccuguaca ggcuguucag gaagagcaac      1380
cugaagcccu ucgagaggga caucagcacc gagaucuacc aggccggcag caccccccgc      1440
aacggcguga agggcuucaa cugcuacuuc ccccugcaga gcuacggcuu ccagcccacc      1500
uacggcgugg cuaccagcc cuacagggug gugguucuga gcuucgagcu gcugcacgcc       1560
cccgccaccg ugugcggccc caagaagagc accaaccugg ugaagaacaa gugcgugaac      1620
uuc                                                                    1623

<210> SEQ ID NO 37
<211> LENGTH: 1623
```

```
<212> TYPE: RNA
<213> ORGANISM: Artificial Sequence
<220> FEATURE:
<223> OTHER INFORMATION: mRNAvaccines

<400> SEQUENCE: 37
auguucgugu uccuggugcu gcugccccug gugagcagcc agugcgugaa ccugaccacc      60
agaacccagc ugcccccgc cuacaccaac agcuucacca gaggcguagua cuaccccgac     120
aagguguuca gaagcagcgu gcugcacagc acccaggacc uguuccugcc cuucuucagc     180
aacgugaccu gguccacgc cauccacgug agcggcacca acggcaccaa gagauucgac      240
aaccccgugc ugcccuucaa cgacggcgug uacuucgcca gcaccgagaa gagcaacauc      300
aucagaggcu ggaucuucgg caccacccug acagcaaga cccagagccu gcugaucgug       360
aacaacgcca ccaacguggu gaucaaggug ugcgaguucc aguucugcaa cgacccccuc      420
cugggcgugu acuaccacaa gaacaacaag agcuggaugg agagcgaguu cagaguguac      480
agcagcgcca acaacugcac cuucgaguac gugagccagc ccuuccugau ggaccuggag      540
ggcaagcagg gcaacuucaa gaaccugaga gaguucgugu ucaagaacau cgacggcuac      600
uucaagaucu acagcaagca cacccccauc aaccugguga gagaccugcc cagggcuuc      660
agcgcccugg agcccuggu ggaccugccc aucggcauca acaucaccag auuccagacc       720
cugcuggccc ugcacagaag cuaccugacc cccggcgaca gcagcagcgg cuggaccgcc      780
ggcgccgccg ccuacuacgu gggcuaccug cagcccagaa ccuuccugcu gaaguacaac      840
gagaacggca ccaucaccga cgccguggac ugcgcccugg accccugag cgagaccaag       900
ugcacccuga gagcuucac cguggagaag ggcaucuacc agaccagcaa cuucagagug       960
cagcccaccg agagcaucgu gagauucccc aacaucacca accugugccc cuucggcgag     1020
guguucaacg ccaccagauu cgccagcgug uacgccugga acagaaagag aaucagcaac     1080
ugcguggccg acuacagcgu gcuguacaac agcgccagcu ucagcaccuu caagugcuac     1140
ggcgugagcc ccaccaagcu gaacgaccug ugcuucacca cguguacgc cgacagcuuc     1200
gugaucagag cgacgaggu gagacagauc gcccccggcc agaccggcaa gaucgccgac     1260
uacaacuaca agcugcccga cgacuucacc ggcugcguga ucgccuggaa cagcaacaac     1320
cuggacagca agguggcgg caacuacaac uacagauaca gacuguucag aaagagcaac     1380
cugaagcccu ucgagagaga caucagcacc gagaucuacc aggccggcag cacccccugc     1440
aacggcgugg agggcuucaa cugcuacuuc ccccugcaga gcuacggcuu ccagcccacc     1500
aacggcgugg gcuaccagcc cuacagagug guggugcuga gcuucgagcu gcugcacgcc     1560
cccgccaccg ugugcggccc caagaagagc accaaccugg ugaagaacaa gugcgugaac     1620
uuc                                                                   1623

<210> SEQ ID NO 38
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 38
auguucgugu uccuggugcu gcugccucug gugagcagcc agugcgugaa ccugaccacc      60
agaacccagc ugccuccugc cuacaccaac agcuucacca gaggcguagua cuaccccgac    120
aagguguuca gaagcagcgu gcugcacagc acccaggacc uguuccugcc uuucuucagc     180
```

| | |
|---|---|
| aacgugaccu gguuccacgc cauccacgug agcggcacca acggcaccaa gagauucgac | 240 |
| aacccugugc ugccuuucaa cgacggcgug uacuucgcca gcaccgagaa gagcaacauc | 300 |
| aucagaggcu ggaucuucgg caccacccug acagcaaga cccagagccu gcugaucgug | 360 |
| aacaacgcca ccaacguggu gaucaaggug ugcgaguucc aguucugcaa cgacccuuc | 420 |
| cugggcgugu acuaccacaa gaacaacaag agcuggaugg agagcgaguu cagaguguac | 480 |
| agcagcgcca acaacugcac cuucgaguac gugagccagc cuuccugau ggaccuggag | 540 |
| ggcaagcagg gcaacuucaa gaaccugaga gaguucgugu caagaacau cgacggcuac | 600 |
| uucaagaucu acagcaagca cacccccuauc aaccugguga gagaccugcc ucagggcuuc | 660 |
| agcgcccugg agccucuggu ggaccugccu aucggcauca acaucaccag auuccagacc | 720 |
| cugcuggccc ugcacagaag cuaccugacc ccuggcgaca gcagcagcgg cuggaccgcc | 780 |
| ggcgccgccg ccuacuacgu gggcuaccug cagccuagaa ccuuccugcu gaaguacaac | 840 |
| gagaacggca ccaucaccga cgccguggac ugcgcccugg acccucugag cgagaccaag | 900 |
| ugcacccuga agagcuucac cguggagaag ggcaucuacc agaccagcaa cuucagagug | 960 |
| cagccuaccg agagcaucgu gagauccccu aacaucacca accugugccc uucggcgag | 1020 |
| guguucaacg ccaccagauu cgccagcgug uacgccugga acagaaagag aaucagcaac | 1080 |
| ugcguggccg acuacagcgu gcuguacaac agcgccagcu ucagcacccu caagugcuac | 1140 |
| ggcgugagcc cuaccaagcu gaacgaccug ugcuucacca cguguacgc cgacagcuuc | 1200 |
| gugaucagag cgacgaggu gagacagauc gcccccuggcc agaccggcaa gaucgccgac | 1260 |
| uacaacuaca agcugccuga cgacuucacc ggcugcguga ucgccuggaa cagcaacaac | 1320 |
| cuggacagca aggugggcgg caacuacaac uacagauaca gacuguucag aaagagcaac | 1380 |
| cugaagccuu ucgagagaga caucagcacc gagaucuacc aggccggcag caccccuugc | 1440 |
| aacggcgugg agggcuucaa cugcuacuuc ccucugcaga gcuacggcuu ccagccuacc | 1500 |
| aacggcgugg gcuaccagcc uuacagagug guggugcuga gcuucgagcu gcugcacgcc | 1560 |
| ccugccaccg ugugcggccc uaagaagagc accaaccugg ugaagaacaa gugcgugaac | 1620 |
| uuc | 1623 |

<210> SEQ ID NO 39
<211> LENGTH: 1623
<212> TYPE: RNA
<213> ORGANISM: Artificial Sequence
<220> FEATURE:
<223> OTHER INFORMATION: mRNAvaccines

<400> SEQUENCE: 39

| | |
|---|---|
| auguucgugu uccuggugcu gcugcccucug gugagcagcc agugcgugaa ccugaccacc | 60 |
| aggacccagc ugccccccgc cuacaccaac agcuucacca ggggcgugua cuaccccgac | 120 |
| aagguguuca ggagcagcgu gcugcacagc acccaggacc uguuccugcc cuucuucagc | 180 |
| aacgugaccu gguccacgc cauccacgug agcggcacca acggcaccaa gagguucgac | 240 |
| aaccccgugc ugcccuucaa cgacggcgug uacuucgcca gcaccgagaa gagcaacauc | 300 |
| aucagggggcu ggaucuucgg caccacccug acagcaaga cccagagccu gcugaucgug | 360 |
| aacaacgcca ccaacguggu gaucaaggug ugcgaguucc aguucugcaa cgacccuuc | 420 |
| cugggcgugu acuaccacaa gaacaacaag agcuggaugg agagcgaguu cagggguguac | 480 |
| agcagcgcca acaacugcac cuucgaguac gugagccagc cuuccugau ggaccuggag | 540 |
| ggcaagcagg gcaacuucaa gaaccugagg gaguucgugu caagaacau cgacggcuac | 600 |

| | |
|---|---|
| uucaagaucu acagcaagca caccccccauc aaccugguga gggaccugcc ccagggcuuc | 660 |
| agcgcccugg agccccuggu ggaccugccc aucggcauca acaucaccag guuccagacc | 720 |
| cugcuggccc ugcacaggag cuaccugacc cccggcgaca gcagcagcgg cuggaccgcc | 780 |
| ggcgccgccg ccuacuacgu gggcuaccug cagcccagga ccuuccugcu gaaguacaac | 840 |
| gagaacggca ccaucaccga cgccguggac ugcgcccugg accccugag cgagaccaag | 900 |
| ugcacccuga gagcuucac cguggagaag ggcaucuacc agaccagcaa cuucaggug | 960 |
| cagcccaccg agagcaucgu gagguucccc aacaucacca accugugccc cuucggcgag | 1020 |
| guguucaacg ccaccagguu cgccagcgug uacgccugga caggaagag gaucagcaac | 1080 |
| ugcguggccg acuacagcgu gcuguacaac agcgccagcu ucagcaccuu caagugcuac | 1140 |
| ggcgugagcc ccaccaagcu gaacgaccug ugcuucacca cguguacgc cgacagcuuc | 1200 |
| gugaucaggg gcgacgaggu gaggcagauc gcccccggcc agaccggcaa gaucgccgac | 1260 |
| uacaacuaca gcugcccga cgacuucacc ggcugcguga ucgccuggaa cagcaacaac | 1320 |
| cuggacagca aggugggcgg caacuacaac uacagguaca ggcuguucag gaagagcaac | 1380 |
| cugaagcccu ucgagaggga caucagcacc gagaucuacc aggccggcag cacccccugc | 1440 |
| aacggcgugg agggcuucaa cugcuacuuc ccccugcaga gcuacggcuu ccagcccacc | 1500 |
| aacggcgugg gcuaccagcc cuacagggug guggugcuga gcuucgagcu gcugcacgcc | 1560 |
| cccgccaccg ugugcggccc caagaagagc accaaccugg ugaagaacaa gugcgugaac | 1620 |
| uuc | 1623 |

<210> SEQ ID NO 40
<211> LENGTH: 1620
<212> TYPE: RNA
<213> ORGANISM: Artificial Sequence
<220> FEATURE:
<223> OTHER INFORMATION: mRNAvaccines

<400> SEQUENCE: 40

| | |
|---|---|
| auguuugugu uccuggugcu gcugccccug gugagcagcc agugcgugaa ccugaccacc | 60 |
| agaacacagc ugccucccgc cuacaccaac uccuucaccc gcggcgugua cuacccugau | 120 |
| aagguguuca ggagcuccgu gcugcacagc acccaggacc uguuccugcc uuucuucucu | 180 |
| aacgugaccu gguuccacgu gauuagcggc acaaacggca ccaagcgguu cgauaacccc | 240 |
| gugcugcccu ucaacgacgg cguguacuuc gccuccaucg aaaaagcaa cauuaucaga | 300 |
| ggcuggaucu ucggcaccac ccuggauucc aagacccagu cccugcugau cgugaacaac | 360 |
| gccaccaacg ucgugaucaa ggugugugag uuccaguucu guaaugaccc cuuccuggac | 420 |
| cacaagaaca caagagcug gauggagagc gaguucaggg uguacagcuc cgccaacaac | 480 |
| ugcacauucg aguacgugag ccagcccuuc cugauggacc uggagggcaa cagggcaac | 540 |
| uucaagaauc ugagagaguu cguguucaag aacaucgaug auacuucaa gaucuacagc | 600 |
| aagcacaccc cuaucaucgu gaggagccu gaggaccugc ccagggcuu cagcgcccug | 660 |
| gagcccucg uggaccugcc uaucggcauc aacaucacaa gguuccagac ccugcuggcc | 720 |
| cugcacaggu ccuaccugac accaggcgac agcagcagcg gcuggacagc cggcgccgcc | 780 |
| gccuacuaug uggggcuaccu gcagcccaga acauuccugc ugaaguauaa cgagaauggc | 840 |
| accaucacag acgccgugga cugugcccug gaucccuga gcgagaccaa gugcacucug | 900 |
| aaguccuuua cagguggagaa gggaaucuac cagacaagca auuucagggu gcagccuaca | 960 |

| | | | | |
|---|---|---|---|---|
| gagagcauug | ugagauuccc | uaacaucacc | aaccugugcc | ccuuugacga aguguuuaac | 1020 |
| gcuacacggu | uugcaucagu | guaugccugg | aacaggaaga | gaaucaguaa cuguguggcc | 1080 |
| gacuacucug | ugcuguauaa | ccuggcuccc | uucuuuacuu | ucaaaugcua cggggugagc | 1140 |
| ccuacuaagc | ugaaugaccu | guguuucaca | aacguguaug | ccgauagcuu ugugaucagg | 1200 |
| ggcgacgaag | ugagacagau | cgcuccaggc | cagacaggca | auauugccga uuacaacuau | 1260 |
| aaacugcccg | augacuucac | aggaugcgug | auugccugga | uagcaauaa gcuggauucu | 1320 |
| aaagugagcg | gcaauuacaa | uuaccuguau | aggcuguuca | gaaagagcaa ccugaagccu | 1380 |
| uucgagagag | acauccccac | ugaaaucuau | caggccggca | auaagcccug caacggcgug | 1440 |
| gcuggcuuua | auuguuacuu | uccccugaga | uccuauagcu | uucgccccac cuauggcgug | 1500 |
| ggacaccagc | cuuacagagu | gguggugcug | uccuucgagc | ugcugcacgc cccugccaca | 1560 |
| gugugcggcc | caaagaaguc | caccaaucug | gugaagaaua | agugcgugaa cuucugauaa | 1620 |

<210> SEQ ID NO 41
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 41

| | | | | |
|---|---|---|---|---|
| auguucgugu | uccuggugcu | gcugcccug | gugagcagcc | agugcgugaa ccugaccacc | 60 |
| aggacccagc | ugcccccgc | cuacaccaac | agcuucacca | ggggcgugua cuaccccgac | 120 |
| aagguguuca | ggagcagcgu | gcugcacagc | acccaggacc | uguucugcc cuucuucagc | 180 |
| aacgugaccu | gguccacgu | gaucagcggc | accaacggca | ccaagagguu cgacaacccc | 240 |
| gugcugcccu | caacgacgg | cguguacuuc | gccagcaucg | agaagagcaa caucaucagg | 300 |
| ggcuggaucu | ucggcaccac | ccuggacagc | aagacccaga | gccugcugau cgugaacaac | 360 |
| gccaccaacg | uggugaucaa | ggugugcgag | uuccaguucu | gcaacgaccc cuuccuggac | 420 |
| cacaagaaca | caagagcug | gauggagagc | gaguucaggg | uguacagcag cgccaacaac | 480 |
| ugcaccuucg | aguacgugag | ccagcccuuc | cugauggacc | uggagggcaa gcagggcaac | 540 |
| uucaagaacc | ugagggaguu | cguguucaag | aacaucgacg | gcuacuucaa gaucuacagc | 600 |
| aagcacaccc | ccauccuggu | gagggagccc | gaggaccugc | ccagggcuu cagcgcccug | 660 |
| gagcccuggu | ggaccugcc | caucggcauc | aacaucacca | gguuccagac ccugcuggcc | 720 |
| cugcacagga | gcuaccugac | ccccggcgac | agcagcagcg | gcuggaccgc cggcgccgcc | 780 |
| gccuacuacg | ugggcuaccu | gcagcccagg | accuuccugc | ugaaguacaa cgagaacggc | 840 |
| accaucaccg | acgccgugga | cugcgcccug | gacccccuga | gcgagaccaa gugcaccccug | 900 |
| aagagcuuca | ccguggagaa | gggcaucuac | cagaccagca | acuucagggu gcagcccacc | 960 |
| gagagcaucg | ugagguuccc | caacaucacc | aaccugugcc | ccuucgacga gguguucaac | 1020 |
| gccaccaggu | ucgccagcgu | guacgccugg | aacaggaaga | ggaucagcaa cugcguggcc | 1080 |
| gacuacagcg | ugcuguacaa | ccuggccccc | uucuucaccu | ucaagugcua cggcgugagc | 1140 |
| cccaccaagc | ugaacgaccu | gugcuucacc | aacguguacg | ccgacagcuu cgugaucagg | 1200 |
| ggcgacgagg | ugaggcagau | cgccccccggc | cagaccggca | acaucgccga cuacaacuac | 1260 |
| aagcugcccg | acgacuucac | cggcugcgug | aucgccugga | acagcaacaa gcuggacagc | 1320 |
| aaggugagcg | gcaacuacaa | cuaccuguac | aggcuguuca | ggaagagcaa ccugaagccc | 1380 |
| uucgagaggg | acaucagcac | cgagaucuac | caggccggca | acaagcccug caacggcgug | 1440 |

| | |
|---|---|
| gccggcuuca acugcuacuu cccccugagg agcuacagcu ucaggcccac cuacggcgug | 1500 |
| ggccaccagc ccuacagggu ggugguscug agcuucgagc ugcugcacgc cccgccacc | 1560 |
| gugugcggcc caagaagag caccaaccug gugaagaaca agugcgugaa cuuc | 1614 |

<210> SEQ ID NO 42
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 42

| | |
|---|---|
| auguucgugu uccuggugcu gcugcccug gugagcagcc agugcgugaa ccugaccacc | 60 |
| aggacccagc ugcccccgc cuacaccaac agcuucacca ggggcguga cuaccccgac | 120 |
| aagguguuca ggagcagcgu gcugcacagc acccaggacc uguccugcc cuucuucagc | 180 |
| aacgugaccu gguccacgu gaucagcggc accaacggca ccaagagguu cgacaacccc | 240 |
| gugcugcccu ucaacgacgg cguguacuuc gccagcaucg agaagagcaa caucaucagg | 300 |
| ggcuggaucu ucggcaccac ccuggacagc aagacccaga gccugcugau cgugaacaac | 360 |
| gccaccaacg uggugaucaa ggugugcgag uuccaguucu gcaacgaccc cuuccuggac | 420 |
| cacaagaaca caagagcug gauggagagc gaguucaggg uguacagcag cgccaacaac | 480 |
| ugcaccuucg aguacgugag ccagcccuuc cugauggacc uggagggcaa gcagggcaac | 540 |
| uucaagaacc ugagggaguu cgucuucaag aacaucgacg gcuacuucaa gaucuacagc | 600 |
| aagcacaccc ccauccuggu gagggagccc gaggaccugc cccagggcuu cagcgcccug | 660 |
| gagcccuggu ggaccugcc caucggcauc aacaucacca gguucagac ccugcuggcc | 720 |
| cugcacagga gcuaccugac ccccggcgac agcagcagcg gcuggaccgc cggcgccgcc | 780 |
| gccuacuacg ugggcuaccu gcagcccagg accuuccugc ugaaguacaa cgagaacggc | 840 |
| accaucaccg acgccgugga cugcgcccug gaccccuga gcgagaccaa ugcacccug | 900 |
| aagagcuuca ccguggagaa gggcaucuac cagaccagca cuucagggu gcagcccacc | 960 |
| gagagcaucg ugaggnuccc caacaucacc aaccugugcc ccuucgacga ggugnucaac | 1020 |
| gccaccaggu ugccagcgu guacgccugg aacaggaaga ggaucagcaa cugcguggcc | 1080 |
| gacuacagcg ugcuguacaa ccuggccccc uucuucaccu ucaagugcua cggcgugagc | 1140 |
| cccaccaagc ugaacgaccu gugcuucacc aacguguacg ccgacagcuu cgugaucagg | 1200 |
| ggcgacgagg ugaggcagau cgcccccggc cagaccggca caucgccga cuacaacuac | 1260 |
| aagcugcccg acgacuucac cggcugcgug aucgccugga acagcaacaa gcuggacagc | 1320 |
| aaggugagcg gcaacuacaa cuaccuguac aggcuguuca ggaagagcaa ccugaagccc | 1380 |
| uucgagaggg acaucagcac cgagaucuac caggccggca caagcccug caacggcgug | 1440 |
| gccggcuuca acugcuacuu cccccugagg agcuacagcu ucaggcccac cuacggcgug | 1500 |
| ggccaccagc ccuacagggu ggugsucug agcuucgagc ugcugcacgc cccgccacc | 1560 |
| gugugcggcc ccaagaagag caccaaccug gugaagaaca agugcgugaa cuuc | 1614 |

<210> SEQ ID NO 43
<211> LENGTH: 672
<212> TYPE: RNA
<213> ORGANISM: Artificial Sequence
<220> FEATURE:
<223> OTHER INFORMATION: mRNAvaccines

<400> SEQUENCE: 43

```
augagggugc agcccaccga gagcaucgug agguucccca acaucaccaa ccugugcccc    60
uucggcgagg uguucaacgc caccagguuc gccagcgugu acgccuggaa caggaagagg   120
aucagcaacu gcguggccga cuacagcgug cuguacaaca gcgccagcuu cagcaccuuc   180
aagugcuacg gcgugagccc caccaagcug aacgaccugu gcuucaccaa cguguacgcc   240
gacagcuucg ugaucagggg cgacgaggug aggcagaucg cccccggcca gaccggcaag   300
aucgccgacu acaacuacaa gcugcccgac gacuucaccg gcugcgugau cgccuggaac   360
agcaacaacc uggacagcaa gguggcggc aacuacaacu accuguacag gcuguucagg   420
aagagcaacc ugaagcccuu cgagagggac aucagcaccg agaucuacca ggccggcagc   480
accccccugca cggcgugga gggcuucaac ugcuacuucc cccugcagag cuacggcuuc   540
cagcccacca cggcgugggc uaccagcccc uacagggugg uggcugag cuucgagcug   600
cugcacgccc ccgccaccgu gugcggcccc aagaagagca ccaaccuggu gaagaacaag   660
ugcgugaacu uc                                                      672
```

<210> SEQ ID NO 44
<211> LENGTH: 529
<212> TYPE: PRT
<213> ORGANISM: Artificial Sequence
<220> FEATURE:
<223> OTHER INFORMATION: NTD-RBD

<400> SEQUENCE: 44

```
Ser Gln Cys Val Asn Leu Thr Thr Arg Thr Gln Leu Pro Pro Ala Tyr
1               5                   10                  15
Thr Asn Ser Phe Thr Arg Gly Val T

```
                225                 230                 235                 240
Asp Ser Ser Ser Gly Trp Thr Ala Gly Ala Ala Tyr Tyr Val Gly
                    245                 250                 255

Tyr Leu Gln Pro Arg Thr Phe Leu Leu Lys Tyr Asn Glu Asn Gly Thr
                    260                 265                 270

Ile Thr Asp Ala Val Asp Cys Ala Leu Asp Pro Leu Ser Glu Thr Lys
                    275                 280                 285

Cys Thr Leu Lys Ser Phe Thr Val Glu Lys Gly Ile Tyr Gln Thr Ser
                    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                    325                 330                 335

Ser Val Tyr Ala Trp Asn Arg Lys Arg Ile Ser Asn Cys Val Ala Asp
                    340                 345                 350

Tyr Ser Val Leu Tyr Asn Ser Ala Ser Phe Ser Thr Phe Lys Cys Tyr
                    355                 360                 365

Gly Val Ser Pro Thr Lys Leu Asn Asp Leu Cys Phe Thr Asn Val Tyr
                    370                 375                 380

Ala Asp Ser Phe Val Ile Arg Gly Asp Glu Val Arg Gln Ile Ala Pro
385                 390                 395                 400

Gly Gln Thr Gly Lys Ile Ala Asp Tyr Asn Tyr Lys Leu Pro Asp Asp
                    405                 410                 415

Phe Thr Gly Cys Val Ile Ala Trp Asn Ser Asn Asn Leu Asp Ser Lys
                    420                 425                 430

Val Gly Gly Asn Tyr Asn Tyr Leu Tyr Arg Leu Phe Arg Lys Ser Asn
                    435                 440                 445

Leu Lys Pro Phe Glu Arg Asp Ile Ser Thr Glu Ile Tyr Gln Ala Gly
                    450                 455                 460

Ser Thr Pro Cys Asn Gly Val Glu Gly Phe Asn Cys Tyr Phe Pro Leu
465                 470                 475                 480

Gln Ser Tyr Gly Phe Gln Pro Thr Asn Gly Val Gly Tyr Gln Pro Tyr
                    485                 490                 495

Arg Val Val Val Leu Ser Phe Glu Leu Leu His Ala Pro Ala Thr Val
                    500                 505                 510

Cys Gly Pro Lys Lys Ser Thr Asn Leu Val Lys Asn Lys Cys Val Asn
                    515                 520                 525

Phe

<210> SEQ ID NO 45
<211> LENGTH: 526
<212> TYPE: PRT
<213> ORGANISM: Artificial Sequence
<220> FEATURE:
<223> OTHER INFORMATION: NTD-RBD

<400> SEQUENCE: 45

Ser Gln Cys Val Asn Leu Thr Arg Thr Gln Leu Pro Pro Ala Tyr
1               5

```
Phe Asp Asn Pro Val Leu Pro Phe Asn Asp Gly Val Tyr Phe Ala Ser
 65                  70                  75                  80

Thr Glu Lys Ser Asn Ile Ile Arg Gly Trp Ile Phe Gly Thr Thr Leu
             85                  90                  95

Asp Ser Lys Thr Gln Ser Leu Leu Ile Val Asn Asn Ala Thr Asn Val
            100                 105                 110

Val Ile Lys Val Cys Glu Phe Gln Phe Cys Asn Asp Pro Phe Leu Gly
            115                 120                 125

Val Tyr His Lys Asn Asn Lys Ser Trp Met Glu Ser Glu Phe Arg Val
            130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
                180                 185                 190

Thr Pro Ile Asn Leu Val Arg Asp Leu Pro Gln Gly Phe Ser Ala Leu
            195                 200                 205

Glu Pro Leu Val Asp Leu Pro Ile Gly Ile Asn Ile Thr Arg Phe Gln
210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Tyr Tyr Val Gly Tyr Leu Gln
                245                 250                 255

Pro Arg Thr Phe Leu Leu Lys Tyr Asn Glu Asn Gly Thr Ile Thr Asp
                260                 265                 270

Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
            370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
            405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
            435                 440                 445

Phe Glu Arg Asp Ile Ser Thr Glu Ile Tyr Gln Ala Gly Ser Thr Pro
            450                 455                 460

Cys Asn Gly Val Glu Gly Phe Asn Cys Tyr Phe Pro Leu Gln Ser Tyr
465                 470                 475                 480
```

```
Gly Phe Gln Pro Thr Tyr Gly Val Gly Tyr Gln Pro Tyr Arg Val Val
                    485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe
        515                 520                 525

<210> SEQ ID NO 46
<211> LENGTH: 527
<212> TYPE: PRT
<213> ORGANISM: Artificial Sequence
<220> FEATURE:
<223> OTHER INFORMATION: NTD-RBD

<400> SEQUENCE: 46

Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Ala Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
                85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Asp Pro Phe
        115                 120                 125

Leu Gly Val Tyr Tyr His Lys Asn Asn Lys Ser Trp Met Glu Ser Glu
    130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
                165                 170                 175

Leu Arg Glu Phe Val Phe Lys Asn Ile Asp Gly Tyr Phe Lys Ile Tyr
            180                 185                 190

Ser Lys His Thr Pro Ile Asn Leu Val Arg Gly Leu Pro Gln Gly Phe
        195                 200                 205

Ser Ala Leu Glu Pro Leu Val Asp Leu Pro Ile Gly Ile Asn Ile Thr
    210                 215                 220

Arg Phe Gln Thr Leu Leu His Arg Ser Tyr Leu Thr Pro Gly Asp Ser
225                 230                 235                 240

Ser Ser Gly Trp Thr Ala Gly Ala Ala Ala Tyr Tyr Val Gly Tyr Leu
                245                 250                 255

Gln Pro Arg Thr Phe Leu Leu Lys Tyr Asn Glu Asn Gly Thr Ile Thr
            260                 265                 270

Asp Ala Val Asp Cys Ala Leu Asp Pro Leu Ser Glu Thr Lys Cys Thr
        275                 280                 285

Leu Lys Ser Phe Thr Val Glu Lys Gly Ile Tyr Gln Thr Ser Asn Phe
    290                 295                 300

Arg Val Gln Pro Thr Glu Ser Ile Val Arg Phe Pro Asn Ile Thr Asn
305                 310                 315                 320
```

Leu Cys Pro Phe Gly Glu Val Phe Asn Ala Thr Arg Phe Ala Ser Val
            325                 330                 335

Tyr Ala Trp Asn Arg Lys Arg Ile Ser Asn Cys Val Ala Asp Tyr Ser
            340                 345                 350

Val Leu Tyr Asn Ser Ala Ser Phe Ser Thr Phe Lys Cys Tyr Gly Val
            355                 360                 365

Ser Pro Thr Lys Leu Asn Asp Leu Cys Phe Thr Asn Val Tyr Ala Asp
            370                 375                 380

Ser Phe Val Ile Arg Gly Asp Glu Val Arg Gln Ile Ala Pro Gly Gln
385                 390                 395                 400

Thr Gly Asn Ile Ala Asp Tyr Asn Tyr Lys Leu Pro Asp Asp Phe Thr
            405                 410                 415

Gly Cys Val Ile Ala Trp Asn Ser Asn Asn Leu Asp Ser Lys Val Gly
            420                 425                 430

Gly Asn Tyr Asn Tyr Leu Tyr Arg Leu Phe Arg Lys Ser Asn Leu Lys
            435                 440                 445

Pro Phe Glu Arg Asp Ile Ser Thr Glu Ile Tyr Gln Ala Gly Ser Thr
            450                 455                 460

Pro Cys Asn Gly Val Lys Gly Phe Asn Cys Tyr Phe Pro Leu Gln Ser
465                 470                 475                 480

Tyr Gly Phe Gln Pro Thr Tyr Gly Val Gly Tyr Gln Pro Tyr Arg Val
            485                 490                 495

Val Val Leu Ser Phe Glu Leu Leu His Ala Pro Ala Thr Val Cys Gly
            500                 505                 510

Pro Lys Lys Ser Thr Asn Leu Val Lys Asn Lys Cys Val Asn Phe
            515                 520                 525

<210> SEQ ID NO 47
<211> LENGTH: 529
<212> TYPE: PRT
<213> ORGANISM: Artificial Sequence
<220> FEATURE:
<223> OTHER INFORMATION: NTD-RBD

<400> SEQUENCE: 47

Ser Gln Cys Val Asn Phe Thr Asn Arg Thr Gln Leu Pro Ser Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
            35                  40                  45

Asn Val Thr Trp Phe His Ala Ile His Val Ser Gly Thr Asn Gly Thr
50                  55                  60

Lys Arg Phe Asp Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
            85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Tyr Pro Phe
            115                 120                 125

Leu Gly Val Tyr Tyr His Lys Asn Asn Lys Ser Trp Met Glu Ser Glu
            130                 135                 140

Phe Arg Val Tyr Ser Ser Ala Asn Asn Cys Thr Phe Glu Tyr Val Ser
145                 150                 155                 160

```
Gln Pro Phe Leu Met Asp Leu Glu Gly Lys Gln Gly Asn Phe Lys Asn
                165                 170                 175

Leu Ser Glu Phe Val Phe Lys Asn Ile Asp Gly Tyr Phe Lys Ile Tyr
            180                 185                 190

Ser Lys His Thr Pro Ile Asn Leu Val Arg Asp Leu Pro Gln Gly Phe
        195                 200                 205

Ser Ala Leu Glu Pro Leu Val Asp Leu Pro Ile Gly Ile Asn Ile Thr
    210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Tyr Tyr Val Gly
                245                 250                 255

Tyr Leu Gln Pro Arg Thr Phe Leu Leu Lys Tyr Asn Glu Asn Gly Thr
            260                 265                 270

Ile Thr Asp Ala Val Asp Cys Ala Leu Asp Pro Leu Ser Glu Thr Lys
        275                 280                 285

Cys Thr Leu Lys Ser Phe Thr Val Glu Lys Gly Ile Tyr Gln Thr Ser
    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
        355                 360                 365

Gly Val Ser Pro Thr Lys Leu Asn Asp Leu Cys Phe Thr Asn Val Tyr
    370                 375                 380

Ala Asp Ser Phe Val Ile Arg Gly Asp Glu Val Arg Gln Ile Ala Pro
385                 390                 395                 400

Gly Gln Thr Gly Thr Ile Ala Asp Tyr Asn Tyr Lys Leu Pro Asp Asp
                405                 410                 415

Phe Thr Gly Cys Val Ile Ala Trp Asn Ser Asn Asn Leu Asp Ser Lys
            420                 425                 430

Val Gly Gly Asn Tyr Asn Tyr Leu Tyr Arg Leu Phe Arg Lys Ser Asn
        435                 440                 445

Leu Lys Pro Phe Glu Arg Asp Ile Ser Thr Glu Ile Tyr Gln Ala Gly
    450                 455                 460

Ser Thr Pro Cys Asn Gly Val Lys Gly Phe Asn Cys Tyr Phe Pro Leu
465                 470                 475                 480

Gln Ser Tyr Gly Phe Gln Pro Thr Tyr Gly Val Gly Tyr Gln Pro Tyr
                485                 490                 495

Arg Val Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
        515                 520                 525

Phe

<210> SEQ ID NO 48
<211> LENGTH: 529
<212> TYPE: PRT
<213> ORGANISM: Artificial Sequence
<220> FEATURE:
<223> OTHER INFORMATION: NTD-RBD
```

```
<400> SEQUENCE: 48

Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Asp Asn Pro Val Leu Pro Phe Asn Asp Gly Val Tyr Phe
65              70                  75                  80

Ala Ser Thr Glu Lys Ser Asn Ile Ile Arg Gly Trp Ile Phe Gly Thr
            85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Asp Pro Phe
        115                 120                 125

Leu Gly Val Tyr Tyr His Lys Asn Asn Lys Ser Trp Met Glu Ser Glu
    130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
            165                 170                 175

Leu Arg Glu Phe Val Phe Lys Asn Ile Asp Gly Tyr Phe Lys Ile Tyr
            180                 185                 190

Ser Lys His Thr Pro Ile Asn Leu Val Arg Asp Leu Pro Gln Gly Phe
        195                 200                 205

Ser Ala Leu Glu Pro Leu Val Asp Leu Pro Ile Gly Ile Asn Ile Thr
    210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Tyr Tyr Val Gly
            245                 250                 255

Tyr Leu Gln Pro Arg Thr Phe Leu Leu Lys Tyr Asn Glu Asn Gly Thr
            260                 265                 270

Ile Thr Asp Ala Val Asp Cys Ala Leu Asp Pro Leu Ser Glu Thr Lys
        275                 280                 285

Cys Thr Leu Lys Ser Phe Thr Val Glu Lys Gly Ile Tyr Gln Thr Ser
    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
            325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
        355                 360                 365

Gly Val Ser Pro Thr Lys Leu Asn Asp Leu Cys Phe Thr Asn Val Tyr
    370                 375                 380

Ala Asp Ser Phe Val Ile Arg Gly Asp Glu Val Arg Gln Ile Ala Pro
385                 390                 395                 400

Gly Gln Thr Gly Lys Ile Ala Asp Tyr Asn Tyr Lys Leu Pro Asp Asp
            405                 410                 415
```

-continued

```
Phe Thr Gly Cys Val Ile Ala Trp Asn Ser Asn Asn Leu Asp Ser Lys
                420                 425                 430

Val Gly Gly Asn Tyr Asn Tyr Arg Tyr Arg Leu Phe Arg Lys Ser Asn
            435                 440                 445

Leu Lys Pro Phe Glu Arg Asp Ile Ser Thr Glu Ile Tyr Gln Ala Gly
    450                 455                 460

Ser Thr Pro Cys Asn Gly Val Glu Gly Phe Asn Cys Tyr Phe Pro Leu
465                 470                 475                 480

Gln Ser Tyr Gly Phe Gln Pro Thr Asn Gly Val Gly Tyr Gln Pro Tyr
                485                 490                 495

Arg Val Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
            515                 520                 525

Phe
```

<210> SEQ ID NO 49
<211> LENGTH: 526
<212> TYPE: PRT
<213> ORGANISM: Artificial Sequence
<220> FEATURE:
<223> OTHER INFORMATION: NTD-RBD

<400> SEQUENCE: 49

```
Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
                20                  25                  30

Ser Ser Val Leu His Ser Thr Gln Asp Leu Phe Leu Pro Phe Phe Ser
            35                  40                  45

Asn Val Thr Trp Phe His Val Ile Ser Gly Thr Asn Gly Thr Lys Arg
50                  55                  60

Phe Asp Asn Pro Val Leu Pro Phe Asn Asp Gly Val Tyr Phe Ala Ser
65                  70                  75                  80

Ile Glu Lys Ser Asn Ile Ile Arg Gly Trp Ile Phe Gly Thr Thr Leu
                85                  90                  95

Asp Ser Lys Thr Gln Ser Leu Leu Ile Val Asn Asn Ala Thr Asn Val
            100                 105                 110

Val Ile Lys Val Cys Glu Phe Gln Phe Cys Asn Asp Pro Phe Leu Asp
        115                 120                 125

His Lys Asn Asn Lys Ser Trp Met Glu Ser Glu Phe Arg Val Tyr Ser
    130                 135                 140

Ser Ala Asn Asn Cys Thr Phe Glu Tyr Val Ser Gln Pro Phe Leu Met
145                 150                 155                 160

Asp Leu Glu Gly Lys Gln Gly Asn Phe Lys Asn Leu Arg Glu Phe Val
                165                 170                 175

Phe Lys Asn Ile Asp Gly Tyr Phe Lys Ile Tyr Ser Lys His Thr Pro
            180                 185                 190

Ile Ile Val Arg Glu Pro Glu Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240
```

```
Ser Gly Trp Thr Ala Gly Ala Ala Tyr Tyr Val Gly Tyr Leu Gln
            245                 250                 255

Pro Arg Thr Phe Leu Leu Lys Tyr Asn Glu Asn Gly Thr Ile Thr Asp
        260                 265                 270

Ala Val Asp Cys Ala Leu Asp Pro Leu Ser Glu Thr Lys Cys Thr Leu
    275                 280                 285

Lys Ser Phe Thr Val Glu Lys Gly Ile Tyr Gln Thr Ser Asn Phe Arg
290                 295                 300

Val Gln Pro Thr Glu Ser Ile Val Arg Phe Pro Asn Ile Thr Asn Leu
305                 310                 315                 320

Cys Pro Phe Asp Glu Val Phe Asn Ala Thr Arg Phe Ala Ser Val Tyr
            325                 330                 335

Ala Trp Asn Arg Lys Arg Ile Ser Asn Cys Val Ala Asp Tyr Ser Val
        340                 345                 350

Leu Tyr Asn Leu Ala Pro Phe Phe Thr Phe Lys Cys Tyr Gly Val Ser
    355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Asn Ile Ala Asp Tyr Asn Tyr Lys Leu Pro Asp Asp Phe Thr Gly
            405                 410                 415

Cys Val Ile Ala Trp Asn Ser Asn Lys Leu Asp Ser Lys Val Ser Gly
        420                 425                 430

Asn Tyr Asn Tyr Leu Tyr Arg Leu Phe Arg Lys Ser Asn Leu Lys Pro
    435                 440                 445

Phe Glu Arg Asp Ile Ser Thr Glu Ile Tyr Gln Ala Gly Asn Lys Pro
450                 455                 460

Cys Asn Gly Val Ala Gly Phe Asn Cys Tyr Phe Pro Leu Arg Ser Tyr
465                 470                 475                 480

Ser Phe Arg Pro Thr Tyr Gly Val Gly His Gln Pro Tyr Arg Val Val
            485                 490                 495

Val Leu Ser Phe Glu Leu Leu His Ala Pro Ala Thr Val Cys Gly Pro
        500                 505                 510

Lys Lys Ser Thr Asn Leu Val Lys Asn Lys Cys Val Asn Phe
    515                 520                 525

<210> SEQ ID NO 50
<211> LENGTH: 14
<212> TYPE: PRT
<213> ORGANISM: Artificial Sequence
<220> FEATURE:
<223> OTHER INFORMATION: linking peptide

<400> SEQUENCE: 50

Ser Phe Thr Val Glu Lys Gly Ile Tyr Gln Thr Ser Asn Phe
1               5                   10

<210> SEQ ID NO 51
<211> LENGTH: 51
<212> TYPE: RNA
<213> ORGANISM: Artificial Sequence
<220> FEATURE:
<223> OTHER INFORMATION: 5'UTR

<400> SEQUENCE: 51
agggagauaa gagagaaaag aagaguaaga agaaauauaa gagccgccac c      51
```

<210> SEQ ID NO 52
<211> LENGTH: 93
<212> TYPE: RNA
<213> ORGANISM: Artificial Sequence
<220> FEATURE:
<223> OTHER INFORMATION: 3'UTR

<400> SEQUENCE: 52
gcugccuucu gcggggcuug ccuucuggcc augcccuucu ucucucccuu gcaccuguac    60
cucuuggucu uugaauaaag ccugaguagg aag                                 93

<210> SEQ ID NO 53
<211> LENGTH: 112
<212> TYPE: RNA
<213> ORGANISM: Artificial Sequence
<220> FEATURE:
<223> OTHER INFORMATION: Poly-A tail

<400> SEQUENCE: 53
aaaaaaaaaa aaaaaaaaaa aaaaaaaaaa agcauaugac uaaaaaaaaa aaaaaaaaaa    60
aaaaaaaaaa aaaaaaaaaa aaaaaaaaaa aaaaaaaaaa aaaaaaaaaa aa           112

<210> SEQ ID NO 54
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 54
auguucgugu uccuggugcu gcugccguua gugaguaguc agugugugaa ccugacuacu    60
cgcacgcagc ugccaccagc guacacgaac agcuucacgc ggggcgugua uuaucccgac   120
aaaguauuuc gcagcagcgu ccugcacucc acccaggacc ucuuccuccc guucuucucc   180
aaugugacgu gguuucacgu cauaucgggg acgaacggga cgaagagguu cgacaauccg   240
guccugccuu uuaacgacgg gguguauuuc gcgucaauag agaagaguaa uauuauccga   300
ggugggaucu ucgggaccac ccuggauagu aagacucagu cucuauugau cgugaauaac   360
gccaccaacg ucguuauaaa ggucugcgag uuucaguucu gcaaugaucc auucuuggau   420
cauaagaaca auaagucgug gauggagagc gaguuucgag uguacucgag ugcaaacaau   480
ugcacuuucg aguacgucuc gcagccguuc uugauggacc uggaggguaa caggggaau   540 uucaagaauc uuagagaauu cgucuuuaag aauauugacg gauacuuuaa gauuauucc   600 aagcauaccc cuauuaucgu ccgggagccg gaggaccugc cgcagggcuu cagcgcucug   660
gagccgcugg uugaccuccc gauagggauc aacaucacgc gguucagac gcuguuagcc   720 cugcacaggu ccuaccugac ucccggcgau aguaguucug gguggacugc aggcgcugcu   780
gcguacuaug ucgggacuu acagccccgc acguucuugu ugaaguacaa cgagaacggc   840
acaaucacgg acgccguuga uugugcccua gauccguuau cggagaccaa guguacucuc   900
aagucguuca ccguggagaa gggcaucuac cagacgucca acuucagggu gcagccgacu   960
gagaguauag uucgguuucc gaacauaacg aaucuaugcc cguuugcga ggguucaau   1020 gcgacgcgcu ucgccuccgu guaugcaugg aaccgaaaac gcauaagcaa uugugucgca  1080
gauuauucag uuuugacaa ucugcccccg uucuucacgu ucaaguguua cggggugagu   1140
ccgacaaagc ugaaugaucu uguuucaca aauguuuaug cggaucguu cgugauacgc   1200 ggagacgaag ugcgucagau ugcuccuggu cagacgggca auauagccga cuauaacuac   1260

| | |
|---|---|
| aagcuaccag acgacuucac ugguugugug auagcuugga auucgaacaa gcuggacagc | 1320 |
| aagguaucag guaauuacaa uuaccuguac cggcuguuca ggaagucgaa uuugaagccu | 1380 |
| uucgagcgcg acaucucgac cgagaucuac caggccggaa acaagccgug caacggagua | 1440 |
| gcaggcuuca acugcuacuu uccguugcgc agcuacaguu ccggccuac cuacgggua | 1500 |
| gggcaccagc ccuaccgcgu aguggugcuc uccuucgagc ugcuccacgc accggccacg | 1560 |
| gugugugggc cgaagaagag caccaaucug gucaagaaca agugcgugaa cuuu | 1614 |

<210> SEQ ID NO 55
<211> LENGTH: 1614
<212> TYPE: RNA
<213> ORGANISM: Artificial Sequence
<220> FEATURE:
<223> OTHER INFORMATION: mRNAvaccines

<400> SEQUENCE: 55

| | |
|---|---|
| auguucgucu uccuggugcu gcuuccgcug gucaguucac agugugugaa cuugaccacg | 60 |
| cggacgcagc uaccccccgc guauacgaac ucguuuacgc gggggguaua uuacccggau | 120 |
| aagguguuuc guaguccgu ucccacagu acucaggacc cuuccuccc guucuucucc | 180 |
| aaugugacgu gguuucacgu cauaucgggg acgaacggga cgaagagguu cgacaacccc | 240 |
| guguugcccu caacgacgg gguuuauuuc gcgucaauag agaagaguaa uauuauccga | 300 |
| ggguggaucu ucgggaccac ccuggauagu aagacucagu cucuauugau cgugaacaac | 360 |
| gccacuaaug uggugaucaa ggugugcgag uuucaguucu gcaaugaucc auucuuggau | 420 |
| cauaagaaca caagaguug gauggagagu gaauuccgug uuuacucuuc agccaacaau | 480 |
| uguaccuucg aguaugucag ucagccguuu cugauggauc uugaaggcaa gcagggcaau | 540 |
| uucaagaauu ugcgcgaguu ugucuucaag aacaucgacg gcuacuucaa gauauacucg | 600 |
| aagcacacgc cgauaauugu gcgcgagccg gaagaucuac cacagggcuu cagugcucug | 660 |
| gagcccuugg uagaucuucc gaucggcaua aauaucacgc guuccagac gcugcuggcg | 720 |
| uugcaccgga guuaccuuac uccgggcgac uccagcagcg gcuggacggc aggggcugca | 780 |
| gcguacuaug uagggguaucu gcaaccgcgc acguucuugu ugaaguacaa cgagaacggc | 840 |
| acgauuacag augccguaga uugugcgcug accccccugu cggagacuaa gugcaccuug | 900 |
| aagaguuuua cugguggagaa gggaaucuac cagacaucua acuuccgggu gcagccgaca | 960 |
| gagaguauug uacguuuccc gaacaucacg aaucuaugcc cguuugacga ggucguuuaac | 1020 |
| gccacgcggu uugcuagugu guaugcgugg aaucgcaagc gcauuagcaa cugcguggcg | 1080 |
| gauuauucag uuugguauaa ucucgcccg uucuucacgu caaguguua cggggugagu | 1140 |
| ccuacaaagc ugaaugaucu cugcuucacc aacgucuacg cggauagcuu uguuauccgc | 1200 |
| ggagacgagg ugaggcagau agcaccuggu cagacgggca auauugcuga cuacaacuau | 1260 |
| aagcucccgg augacuucac cgggugcguu auagcgugga acagcaauaa guuagauucg | 1320 |
| aaggugucgg gaaacuacaa uuaucucuau cggcuguuca ggaagucgaa cuuaaagccu | 1380 |
| uuugagcgug auauaucuac cgagauauau caggcuggga auaagccgug caacggggua | 1440 |
| gcaggcuuca acugcuacuu cccguugcgc agcuauuccu uucggcccac cuacggggua | 1500 |
| gggcaccagc ccuaccgcgu aguguacug ucguuugagc ugcugcaugc uccagcgaca | 1560 |
| guaugugggc cgaagaaguc gacgaacuug gugaagaaca agugcgucaa cuuc | 1614 |